(12) United States Patent
Gartner et al.

(10) Patent No.: US 11,072,629 B2
(45) Date of Patent: *Jul. 27, 2021

(54) REPROGRAMMING OF CELLULAR ADHESION

(71) Applicant: The Regents of the University of California, Oakland, CA (US)

(72) Inventors: Zev Jordan Gartner, Pacifica, CA (US); Nicholas Scott Selden, San Francisco, CA (US); Michael E. Todhunter, San Francisco, CA (US); Samantha Isabel Liang, San Francisco, CA (US); Robert Joseph Weber, San Francisco, CA (US); Noel Youngho Jee, San Francisco, CA (US); Jennifer S. Liu, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 303 days.

This patent is subject to a terminal disclaimer.

(21) Appl. No.: 15/482,591

(22) Filed: Apr. 7, 2017

(65) Prior Publication Data
US 2017/0305955 A1    Oct. 26, 2017

Related U.S. Application Data

(62) Division of application No. 14/349,644, filed as application No. PCT/US2012/063092 on Nov. 1, 2012, now Pat. No. 9,650,407.

(60) Provisional application No. 61/554,912, filed on Nov. 2, 2011.

(51) Int. Cl.
| C07H 21/04 | (2006.01) |
| A61K 47/26 | (2006.01) |
| A61K 47/54 | (2017.01) |

(52) U.S. Cl.
CPC ............ *C07H 21/04* (2013.01); *A61K 47/26* (2013.01); *A61K 47/542* (2017.08)

(58) Field of Classification Search
None
See application file for complete search history.

(56) References Cited

U.S. PATENT DOCUMENTS

| 5,416,203 A | 5/1995 | Letsinger et al. |
| 5,420,330 A | 5/1995 | Brush et al. |
| 5,571,677 A | 11/1996 | Gryaznov |

(Continued)

FOREIGN PATENT DOCUMENTS

| JP | 2003219881 | 8/2003 |
| WO | WO 2013/049405 | 4/2013 |

OTHER PUBLICATIONS

Machine translation of Han JP 2003-219881 downloaded Aug. 12, 2015.*

(Continued)

*Primary Examiner* — Neil P Hammell
(74) *Attorney, Agent, or Firm* — Edward J. Baba; Shweta Chandra; Bozicevic, Field & Francis LLP

(57) ABSTRACT

Disclosed are membrane-anchored polynucleotides, and compositions comprising the membrane-anchored polynucleotides. Also disclosed are the processes for the synthesis of these compounds, compositions comprising such compounds, and the use of such compounds and compositions in research and therapeutic applications.

23 Claims, 53 Drawing Sheets
Specification includes a Sequence Listing.

A

5'-C18-100mer-20bp Duplex

B

3'-C16-15bp Duplex

(56) References Cited

U.S. PATENT DOCUMENTS

| | | | |
|---|---|---|---|
| 5,763,162 | A | 6/1998 | Glazer et al. |
| 6,861,260 | B2 | 3/2005 | Sugano et al. |
| 6,890,556 | B1 | 5/2005 | Segura et al. |
| 7,615,539 | B2 | 11/2009 | Uhlmann et al. |
| 7,741,297 | B2 | 6/2010 | Jiang et al. |
| 9,650,407 | B2 * | 5/2017 | Gartner .................. A61K 47/26 |
| 2003/0078314 | A1 | 4/2003 | Johnson et al. |
| 2004/0013654 | A1 | 1/2004 | Kramer et al. |
| 2005/0164974 | A1 * | 7/2005 | Gold .................... A61K 9/1272 514/44 R |
| 2006/0099649 | A1 | 5/2006 | Goh et al. |
| 2007/0196284 | A1 | 8/2007 | Tournier et al. |
| 2007/0275047 | A1 * | 11/2007 | Pfeiffer ................ A61K 47/549 424/450 |
| 2007/0280929 | A1 | 12/2007 | Hoerr et al. |
| 2010/0048421 | A1 * | 2/2010 | Han .......................... B82B 1/00 506/15 |

OTHER PUBLICATIONS

Thompson et al., Dynamic Gene Expression Profiling Using a Microfabricated Living Cell Array; Anal. Chem, vol. 76, pp. 4098-4103, 2004 (Year: 2004).*

Simons et al., Functional rafts in cell membranes, Nature, vol. 387, pp. 569-572, 1997 (Year: 1997).* https://en.wikipedia.org/wiki/Phosphatidylcholine; Wikipedia, 'Phosphatidylcholine'; pp. 1-5, Accessed Feb. 21, 2020 (Year: 2020).*

Borisenko et al. (2009) DNA modification of live cell surface. Nucleic Acids Research, 37(4):e28, pp. 1-11 (Year: 2009).*

Chan et al. (2009) Effects of linker sequences on vesicle fusion mediated by lipid-anchored DNA oligonucleotides. PNAS, 106(4): 979-984 (Year: 2009).*

Gartner et al. (2009) Programmed assembly of 3-dimensional microtissues with defined cellular connectivity. PNAS, 106(12):4606-4610 (Year: 2009).*

Borisenko et al. (2008) "DNA modification of live cell surface" *Nucleic Acids Research* 37(4):e28 (11 pgs).

Chan et al. "Effects of linker sequences on vesicle fusion mediated by lipid-anchored DNA oligonucleotides" PNAS, 2008, vol. 106, No. 4, pp. 979-984.

Chan et al. "Lipid-anchored DNA mediates vesicle fusion as observed by lipid and content mixing" Biointerphases, 2008, vol. 3, No. 2, pp. 94305-945080.

Chung et al. "DNA-tethered Membranes Formed by Giant Vesicle Rupture" J Sruct Biol., 2009, vol. 168, No. 1, pp. 190-199.

Fahy et al. "A comprehensive classification system for lipids" J. Lipid Research, 2005, vol. 46, pp. 839-861.

Gartner et al. "Programmed assembly of 3-dimensional microtissues with defined cellular connectivity" PNAS, 2009, vol. 106, No. 12, pp. 4606-4610.

Gartner et al. "Programmed assembly of 3-dimensional microtissues with defined cellular connectivity—supporting information" PNAS, 2009, 10.1073/pnas.0900717106, 1-11.

Hsiao et al. "Direct Cell Surface Modification with DNA for the Capture of Primary Cells and the Investigation of Myotube Formation on Defined Patterns" HHMI, 2009, vol. 25, No. 12, pp. 6985-6991.

Huang (1977) "A structural model for the cholesterol-phosphatidyicholine complexes in bilayer membranes" Lipids 12(4):348-356.

Kansy et al. "Physicochemical high throughput screening: Parallel artificial membrane permeability assay in the description of passive absorption processes" J. Med. Chem., 1998, vol. 41, No. 7, pp. 1007-1010.

Liu et al. "Membrane Anchored Immunostimulatory Oligonucleotides for In Vivo Cell Modification and Localized Immunotherapy" Andew. Chem. Int., 2011, vol. 50, Issue 31, pp. 7052-7055.

Ma et al. "Lipid Membrane Adhesion and Fusion Driven by Designed, Minimally Multivalent Hydrogen-Bonding Lipids" J. Am. Chem. Soc., 2009, vol. 131, No. 46, pp. 16919-16926.

MacKellar et al. "Synthesis and physical properties of anti-H IV antisense oligonucleotides bearing terminal lipophilic groups" Nucleic Acids Research, 1992, vol. 20, No. 13, pp. 3411-3417.

Selden NS et al. "Chemically Programmed Cell Adhesion with Membrane-Anchored Oligonucleotides" J. Am. Chem. Soc., 2012, vol. 134, pp. 765-768.

Van Lengerich et al. (2010) "Covalent attachment of lipid vesicles to a fluid-supported bilayer allows observation of DNA-mediated vesicle interactions" *Langmuir* 26(11):8666-8672.

Yang et al. "Immobilized artificial membranes—screens for drug membrane interactions" Advanced Drug Delivery Reviews, 1996, vol. 23., pp. 229-256.

Yu et al. "Engineering supported membranes for cell biology" Med. Biol. Eng. Comput., 2010, vol. 48, pp. 955-963.

* cited by examiner

A

B

D

Programmed Assemblies (WT)

| day 1 | day 4 | day 16 |
|---|---|---|
|  Cleaved casp-3 DAPI | | |
| Ki-67 DAPI |  |  |

MCF10A growth → growth arrest → lumen formation

Microtissue ⟶ Acinus

D

REPROGRAMMING OF CELLULAR ADHESION

CROSS-REFERENCE TO RELATED APPLICATIONS

This application is a divisional of U.S. patent application Ser. No. 14/349,644, filed Apr. 3, 2014, issued as U.S. Pat. No. 9,650,407, which is a 371 of International Application Ser. No. PCT/US2012/063092, filed Nov. 1, 2012, which claims priority to the filing date of the United States Provisional Patent Application Ser. No. 61/554,912, filed Nov. 2, 2011, the disclosure of which is incorporated herein by reference.

STATEMENT REGARDING FEDERALLY SPONSORED RESEARCH

This invention was made with government support under grant nos. W81XWH-10-1-1023 and W81XWH-13-1-0221 awarded by The United States Army Medical Research and Materiel Command. The government has certain rights in the invention.

INTRODUCTION

Cells interact with materials and each other through adhesion molecules on their surfaces. These interactions serve to physically couple cells to their surroundings, and also alter cell behavior by triggering signaling cascades within the cytosol. There is considerable interest in understanding the mechanics of cell adhesion and in the development of methods to control cellular adhesion.

SUMMARY

The present disclosure provides membrane anchored polynucleotides, and compositions comprising the membrane anchored polynucleotides, Also provided are methods for the synthesis of the membrane anchored polynucleotides, compositions comprising such membrane anchored polynucleotides, and the use of such membrane anchored polynucleotides and compositions thereof in certain therapeutic and research applications, including certain applications relating to controlling cellular adhesion.

In one embodiment, a composition is provided which comprises (1) a compound having a membrane anchoring region comprising a long alkyl chain of at least 12 carbon atoms; and (2) a polynucleotide conjugated to the membrane anchoring region, which contains at least 50 nucleotides and comprises (a) a linker region made up of a contiguous stretch of at least about 20 nucleotides, and (b) a membrane distal adhesion region comprising at least 10 nucleotides, positioned distal to the linker region, that is not hybridizable to the linker region. Said polynucleotide may he DNA, and may be conjugated to the membrane anchoring region at the 5' end. In another embodiment, a composition is provided which comprises two such compounds as described, wherein the membrane distal adhesion regions of the compounds are hybridizable.

In another embodiment, a composition is provided which comprises (1) a compound having a membrane anchoring region comprising a monoalkyl chain of at least 12 carbon atoms; and (2) a polynucleotide conjugated to the membrane anchoring region, which contains at least 50 nucleotides and comprises (a) a linker region made up of a contiguous stretch of at least about 20 nucleotides, and (b) a membrane distal adhesion region comprising at least 10 nucleotides, positioned distal to the linker region, that is not hybridizable to the linker region. The monoalkyl chain may be a monoalkylamide. In certain embodiments, the monoalkylamide comprises 16 to 18 carbon atoms.

In another embodiment, a composition is provided which comprises (1) a compound having a membrane anchoring region comprising a dialkylphosphoglyceride; and (2) a polynucleotide conjugated to the membrane anchoring region, which contains at least 50 nucleotides and comprises (a) a linker region made up of a contiguous stretch of at least about 20 nucleotides, and (b) a membrane distal adhesion region comprising at least 10 nucleotides, positioned distal to the linker region, that is not hybridizable to the linker region. The dialkylphosphoglyceride may be a $C_{16}$ dialkylphosphoglyceride.

In one embodiment, a composition is provided which comprises (1) a compound having a membrane anchoring region comprising a long alkyl chain of at least 12 carbon atoms; and (2) a polynucleotide conjugated to the membrane anchoring region, which contains at least 50 nucleotides and comprises (a) a linker region made up of a contiguous stretch of about 20 to 200 nucleotides, and (b) a membrane distal adhesion region comprising at least 10 nucleotides, positioned distal to the linker region, that is not hybridizable to the linker region. Such contiguous stretch of the liker region may be made up of only one type of base, such as thymine. In certain embodiments, such contiguous stretch of the liker region may he made up of two types of bases, such as thymine or adenine nucleotides.

In another embodiment, a composition is provided which comprises (1) a compound having a membrane anchoring region comprising a long alkyl chain of at least 12 carbon atoms; (2) a polynucleotide conjugated to the membrane anchoring region, which contains at least 50 nucleotides and comprises (a) a linker region made up of a contiguous stretch of at least about 20 nucleotides, and (b) a membrane distal adhesion region comprising at least 10 nucleotides, positioned distal to the linker region, that is not hybridizable to the linker region; and (3) a fluorophore or pharmaceutical composition. The fluorophore or pharmaceutical composition may be conjugated to the polypeptide.

In another embodiment, a composition is provided which comprises any two of the aforementioned compounds, wherein the membrane distal adhesion regions of the compounds are hybridizable.

In another embodiment, an isolated membrane is provided which comprises any of the aforementioned compositions. The isolated membrane may be part of a whole cell.

In another embodiment, a kit is provided which comprises any of the aforementioned compositions. Such kit may comprise an isolated membrane which comprises any of the aforementioned compositions.

The present disclosure also provides methods for using any of the aforementioned compositions. In one embodiment, a method is provided that comprises contacting a membrane with a composition which comprises (1) a compound having a membrane anchoring region comprising a long alkyl chain of at least 12 carbon atoms; and (2) a polynucleotide conjugated to the membrane anchoring region, which contains at least 50 nucleotides and comprises (a) a linker region made up of a contiguous stretch of at least about 20 nucleotides, and (b) a membrane distal adhesion region comprising at least 10 nucleotides, positioned distal to the linker region, that is not hybridizable to the linker region; and incubating the composition with the membrane under conditions allowing insertion of said composition into the membrane. incubating said composition with said lipid membrane under conditions allowing insertion of said composition into said lipid membrane. The method may further comprise contacting the composition with a cargo, including without limitation a lipid vesicle. In some embodiments, the lipid vesicle contains a pharmaceutical composition.

In another embodiment, a method is provided which comprises (1) contacting a membrane with a composition which comprises (i) a compound having a membrane anchoring region comprising a long alkyl chain of at least 12 carbon atoms; and (ii) a polynucleotide conjugated to the membrane anchoring region, which contains at least 50 nucleotides and comprises (a) a linker region made up of a contiguous stretch of at least about 20 nucleotides, and (b) a membrane distal adhesion region comprising at least 10 nucleotides, positioned distal to the linker region, that is not hybridizable to the linker region; and incubating the composition with the membrane under conditions allowing insertion of said composition into the membrane; (2) contacting the membrane with a second composition which comprises (i) a compound having a membrane anchoring region comprising a long alkyl chain of at least 12 carbon atoms; and (ii) a polynucleotide conjugated to the membrane anchoring region, which contains at least 50 nucleotides and comprises (a) a linker region made up of a contiguous stretch of at least about 20 nucleotides, and (b) a membrane distal adhesion region comprising at least 10 nucleotides, positioned distal to the linker region, that is not hybridizable to the linker region; and incubating the composition with the membrane under conditions allowing insertion of said second composition into the membrane; wherein the membrane distal adhesion region of the second composition hybridizes to the membrane distal adhesion region of the first composition.

In another embodiment, a method is provided that comprises (i) contacting a membrane with a first composition which comprises (1) a compound having a membrane anchoring region comprising a long alkyl chain of at least 12 carbon atoms; and (2) a polynucleotide conjugated to the membrane anchoring region, which contains at least 50 nucleotides and comprises (a) a linker region made up of a contiguous stretch of at least about 20 nucleotides, and (b) a membrane distal adhesion region comprising at least 10 nucleotides, positioned distal to the linker region, that is not hybridizable to the linker region; and incubating the composition with the membrane under conditions allowing insertion of said composition into the membrane; and (ii) contacting a surface comprising a second composition according under conditions allowing for said first composition to hybridize to said second composition. In some embodiments, an agent may be added, including without limitation a drug.

BRIEF DESCRIPTION OF THE DRAWINGS

The invention may be best understood from the following detailed description when read in conjunction with the accompanying drawings. Included in the drawings are the following figures.

Panel A: Representative time-lapse images of emergent phenotypes, showing normal and emergent phenotypes in the mosaic MCF10ARas/MCF10AWT microtissues. Panel B: Quantification of normal, basal cell extrusion, and motile multicellular protrusion frequency in homogeneous and heterogeneous microtissues. Data are expressed as the mean of at least 700 observations from four independent experiments, and error bars represent the SD of the mean. Panel C: Sensitivity of the frequency of emergent phenotypes to the addition of high-activity DNase immediately after assembly. Panel D: Sensitivity of cell extrusion and (Panel E) motile multicellular protrusions to inhibition of PI3K by LY294002 and MEK by PD325901. Values are the averages of at least 400 total events from three independent experiments, and error bars show the SD of the means. Scale bar, 20 μm. ***$p<0.001$; ns, not significant (one-way ANOVA and Tukey's test).

Figure 28:
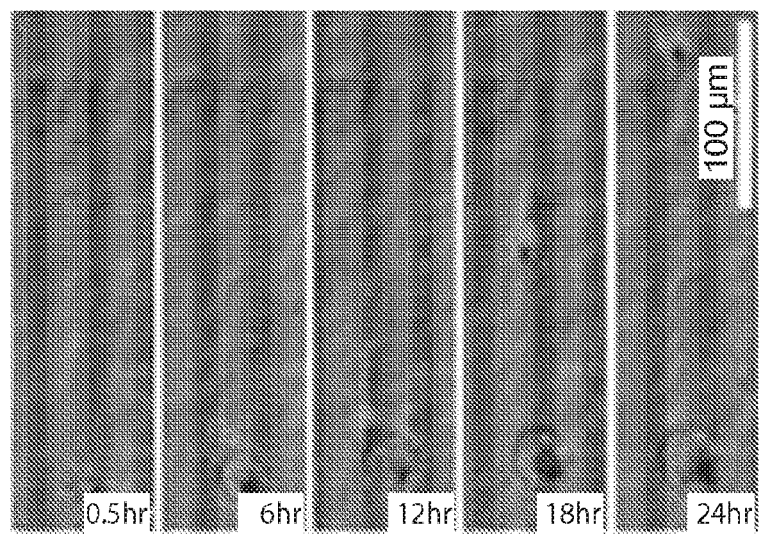
Figure 28:
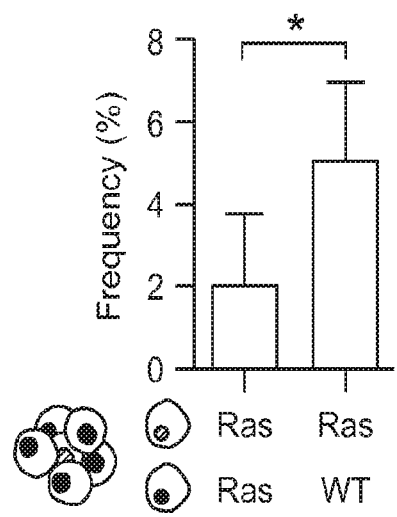
Figure 28:
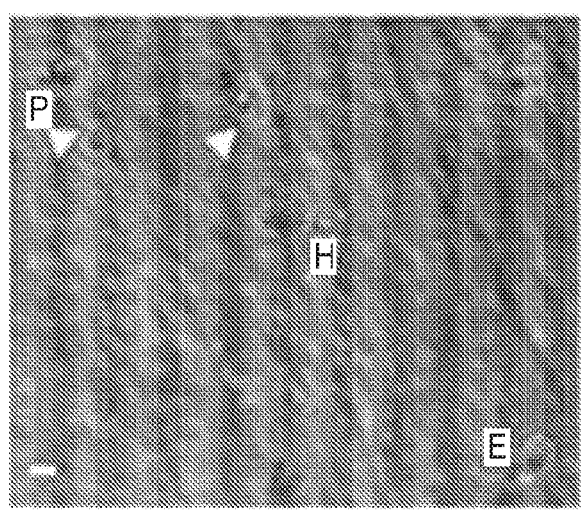
Figure 28:
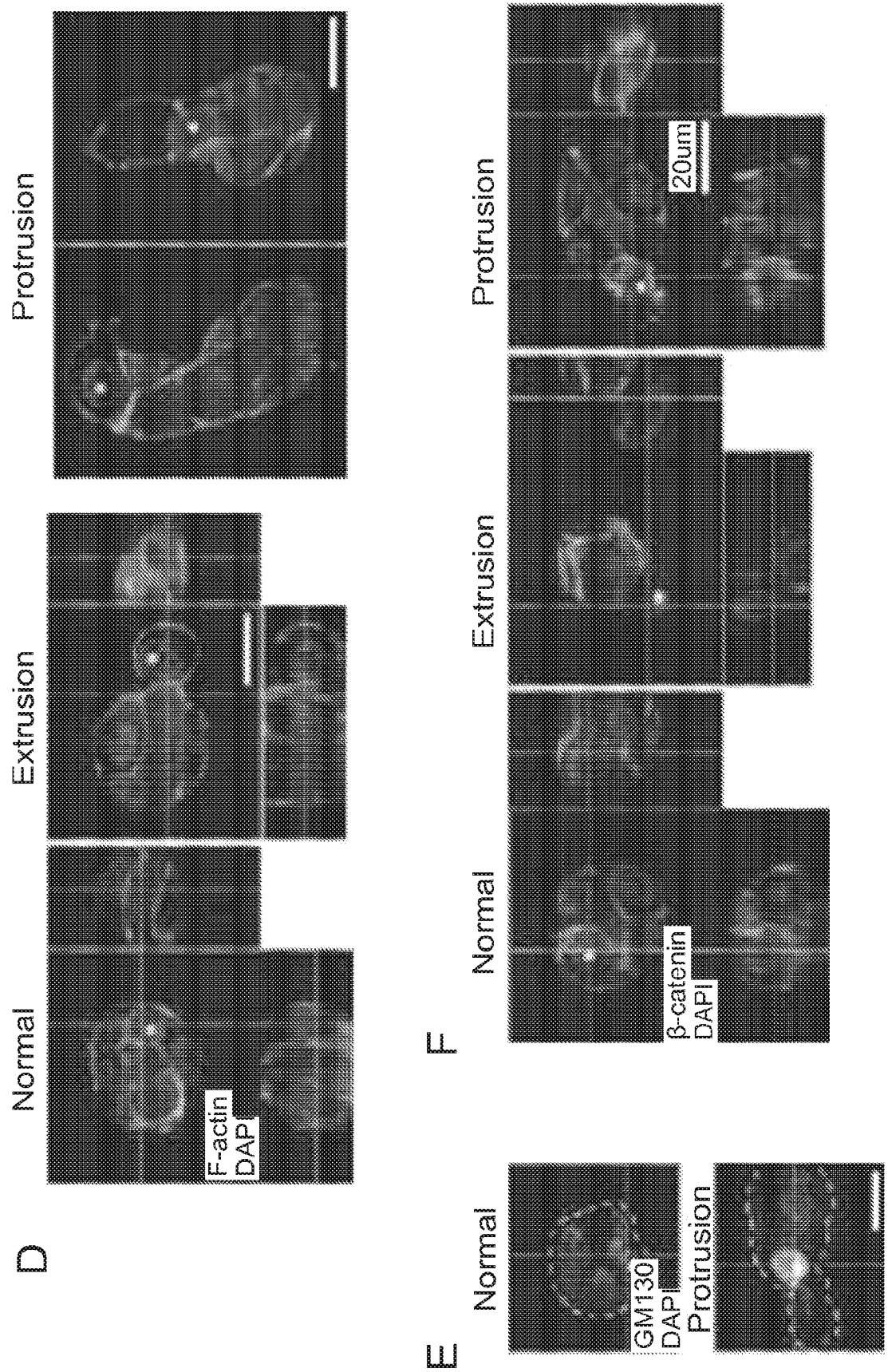
Figure 28:
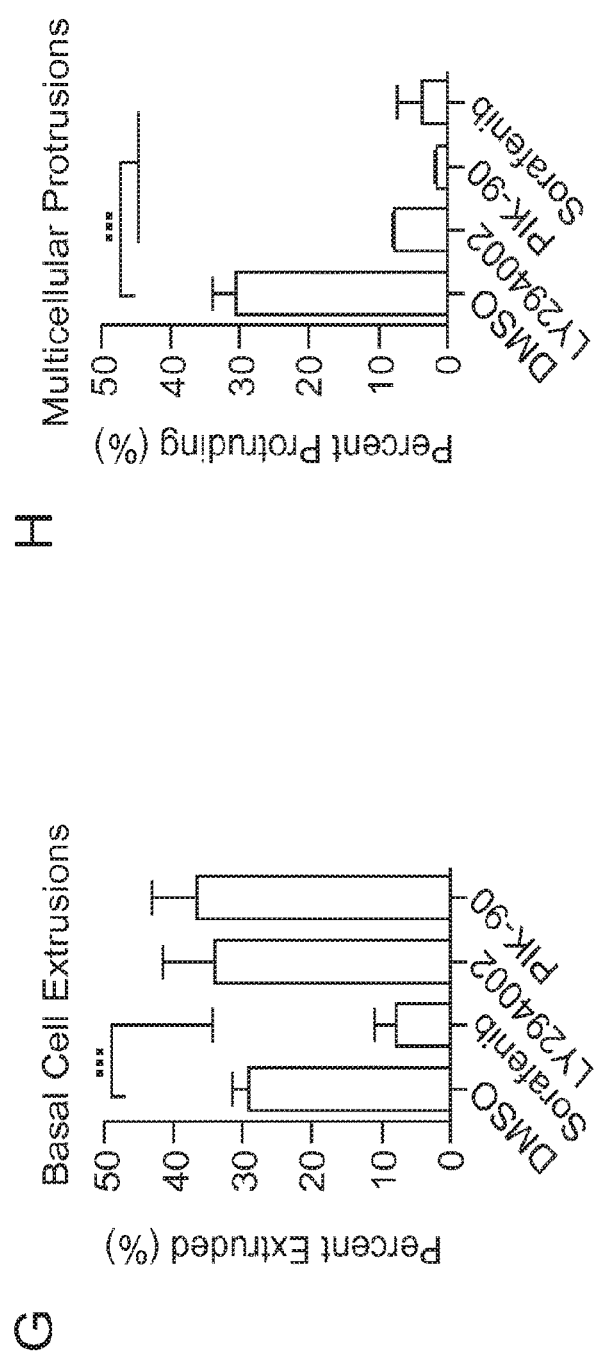
Figure 28:
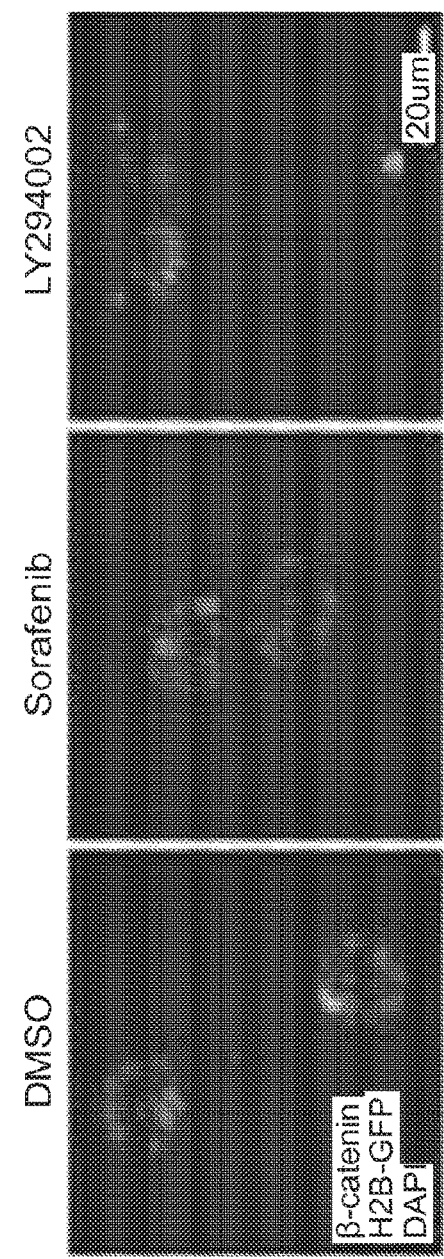
Figure 28:
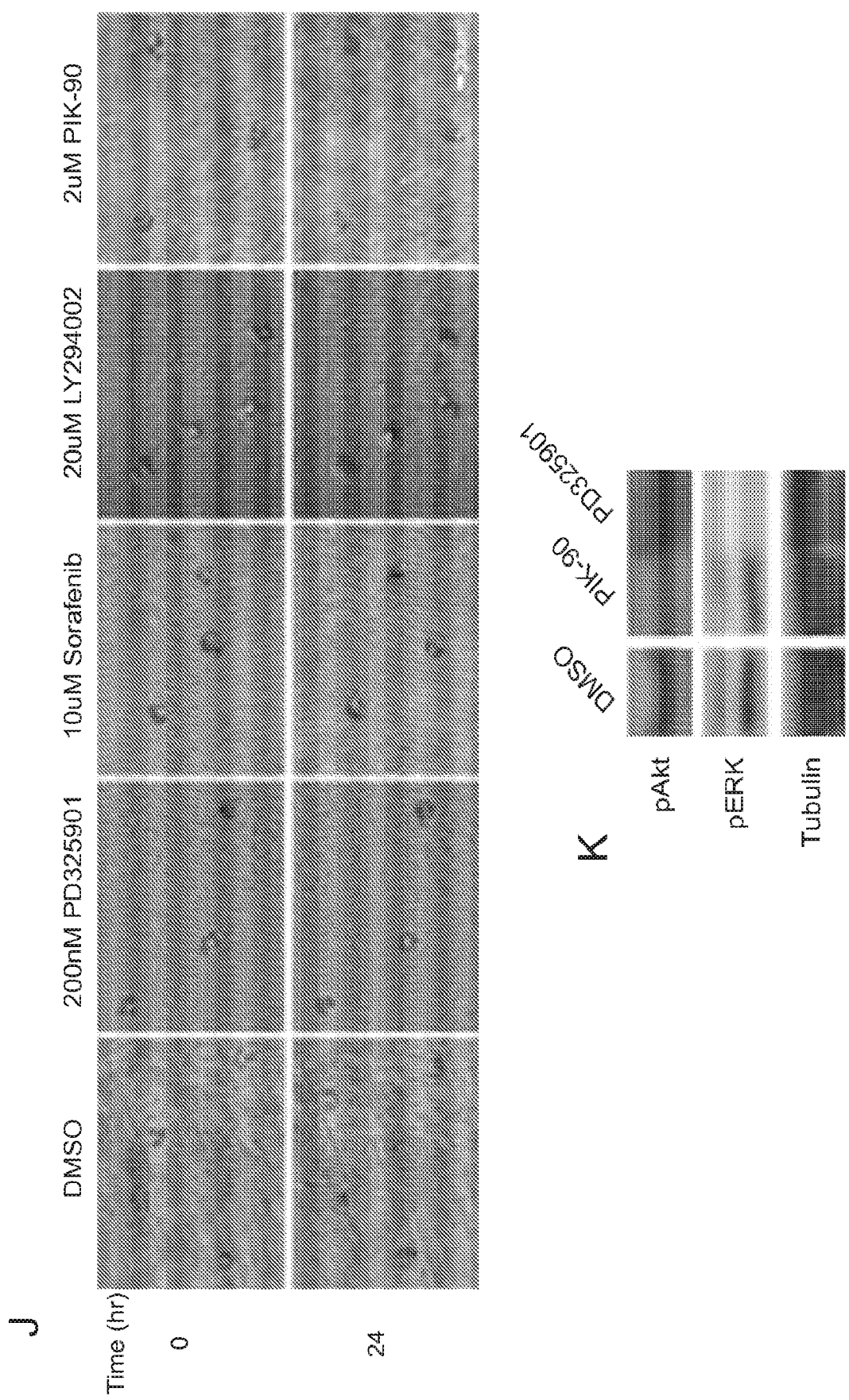

FIG. 28, Panels A-K depict characterization of emergent behaviors. Panel A: Representative time-series images of a hypermotile MCF10ARas cell from a heterogeneous microtissues, Scale bar=100 μm. Panel B: Quantification of hypermotile MCF10ARas behavior in microtissues of heterogeneous and homogeneous composition across 532 observations from 4 replicate experiments. Data are shown as the mean with error bars representing the standard deviation of the mean. Panel C: Representative image of heterogeneous microtissues in DMSO-treated control treated with ethidium homodimer-1. Extruding (E), protruding (P), and hypermotile (H) cells are labeled and do not uptake ethidium homodimer. Arrowheads show other cells in the same field which have taken up ethidium homodimer. Panel D: Representative confocal, immunofluorescence images of normal, basal extrusion, and motile multicellular protrusion phenotypes stained for F-actin. Orthogonal x-z and y-z planes are also shown. Samples were imaged for 12 hr prior to fixing and staining. The x-y coordinates of all microtissues manifesting emergent phenotypes were identified from the time-lapse images. Motile multicellular protrusions and basal extrusions thus identified were relocated for imaging by confocal microscopy. Panel E: Representative confocal, immunofluorescence images of normal and protrusion phenotypes stained for GM130 after 12 hr in 3D culture as in C. The border of the microtissue is traced in dashed outline. Panel F: Representative confocal, immunofluorescence images of normal, basal extrusion, and motile multicellular protrusion phenotypes stained for β-catenin after 12 hr in 3D culture as in Panels C and D. Asterisks mark H2R-GFP-expressing MCF10ARas cells in Panels D, E, and F. Panels G and H: Quantification of cell extrusion and protrusion frequency in heterogeneous microtissues when treated with LY294002, PIK90, or Sorafenib over 24 hr in 3D culture. Values are the average of three independent experiments. Panel I: Representative confocal, immunofluorescence images of heterogeneous MCF10ARas/MCF10AWT aggregates treated with LY294002. or Sorafenib after 24 hr in 3D culture and then stained for β-catenin. Panel J: Representative phase contrast images of heterogeneous MCF10ARas/MCF10AWT aggregates treated with kinase inhibitors after 0 and 24 hr in 3D culture. Panel K: Western blot of phospho-ERK and phospho-Akt Ser473 in MC10ARas cells treated with PIK-90 or PD325901. Scale bar=20 μm except for Panel A.

Figure 29:
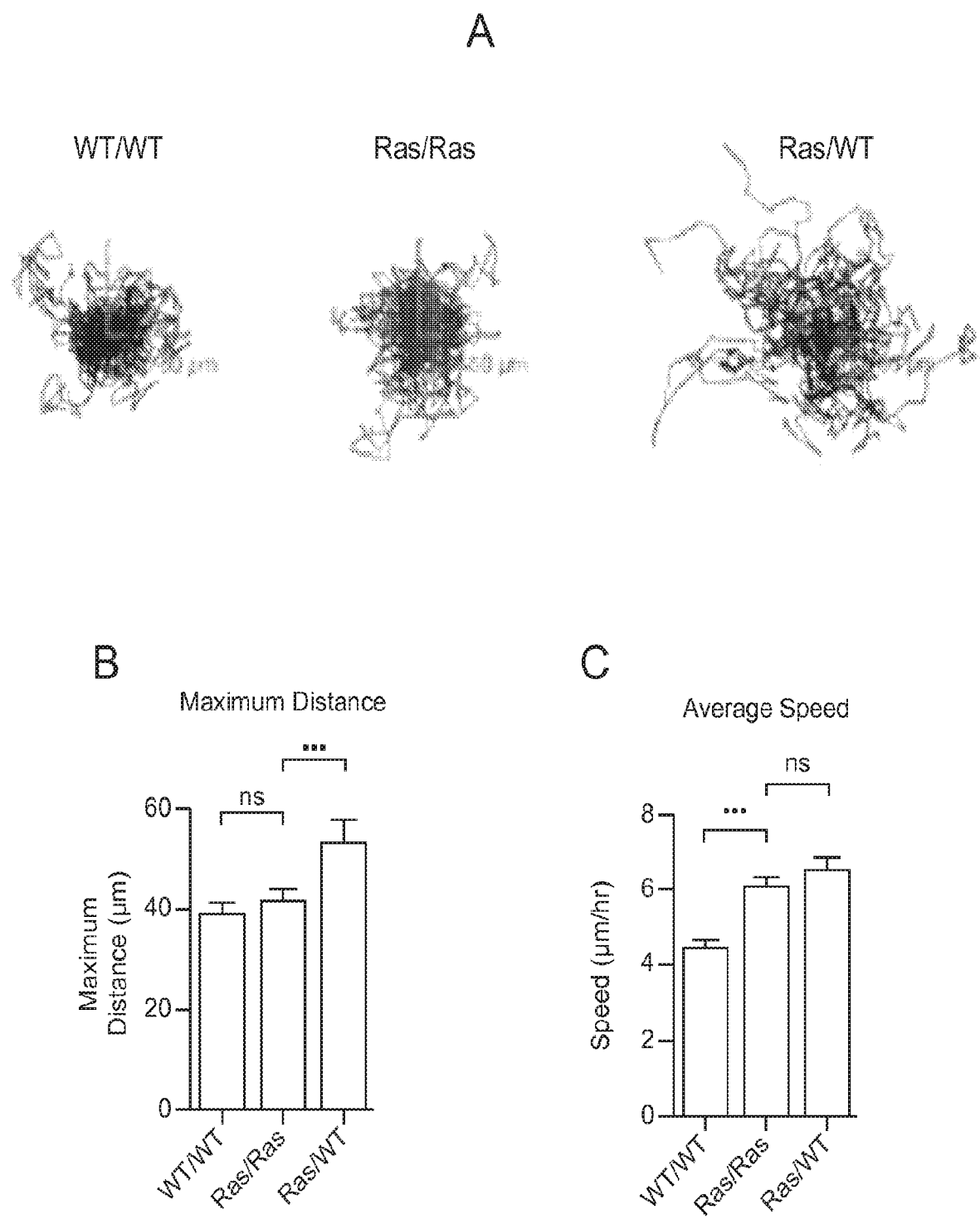
Figure 29:
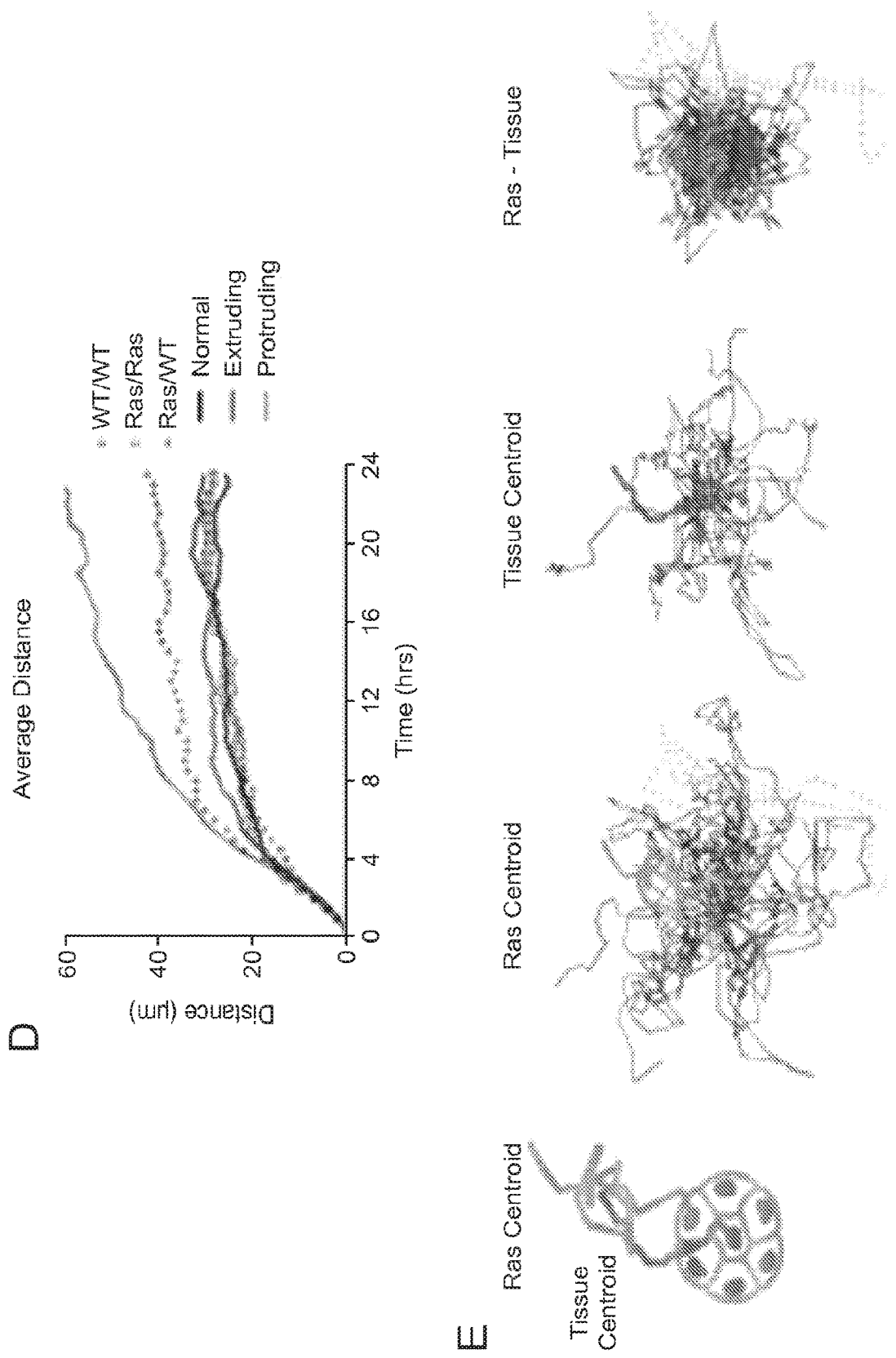

FIG. 29, Panels A-E show quantitative analysis of cell motility during emergent behaviors. Panel A: A total of 30 superimposed 24 hr trajectories for cells expressing H2B-GFP fusions growing in homogeneous and heterogeneous MCF10ARas/MCF10AWT microtissues of the indicated composition. Panels B-C: Average maximum distance traveled (Panel B) and speed (Panel C) of the H2B-GFP-expressing cell under the conditions in Panel A. Panel D: Average distance traveled as a function of time for H2B-GFP-expressing cell in either homogeneous or heterogeneous microtissues. Average distances for H2B-GFP-expressing cells in heterogeneous microtissues are broken down into normal, motile multicellular protrusion, and basal extrusion phenotypes. Panel E: Trajectories of H2B-GFP-expressing MCF10ARas cells and the centroid of the surrounding WT microtissue. Microtissue trajectories (center) are subtracted from MCF10ARas trajectories (left) to produce the residual trajectories (right). A representative MCF10ARas cell (green), associated microtissue (red), and residual trajectory (hatched green and red) are highlighted. Trajectory of a hypermotile cell leaves a large residual (dashed orange lines). For Panels B and C, values are expressed as the mean with SD of 525 observations for three replicate experiments. For Panels A, D, and E, data are shown from a single experiment that is representative of three replicates. Trajectories are bounded by a 100 μm radius.

Figure 30:
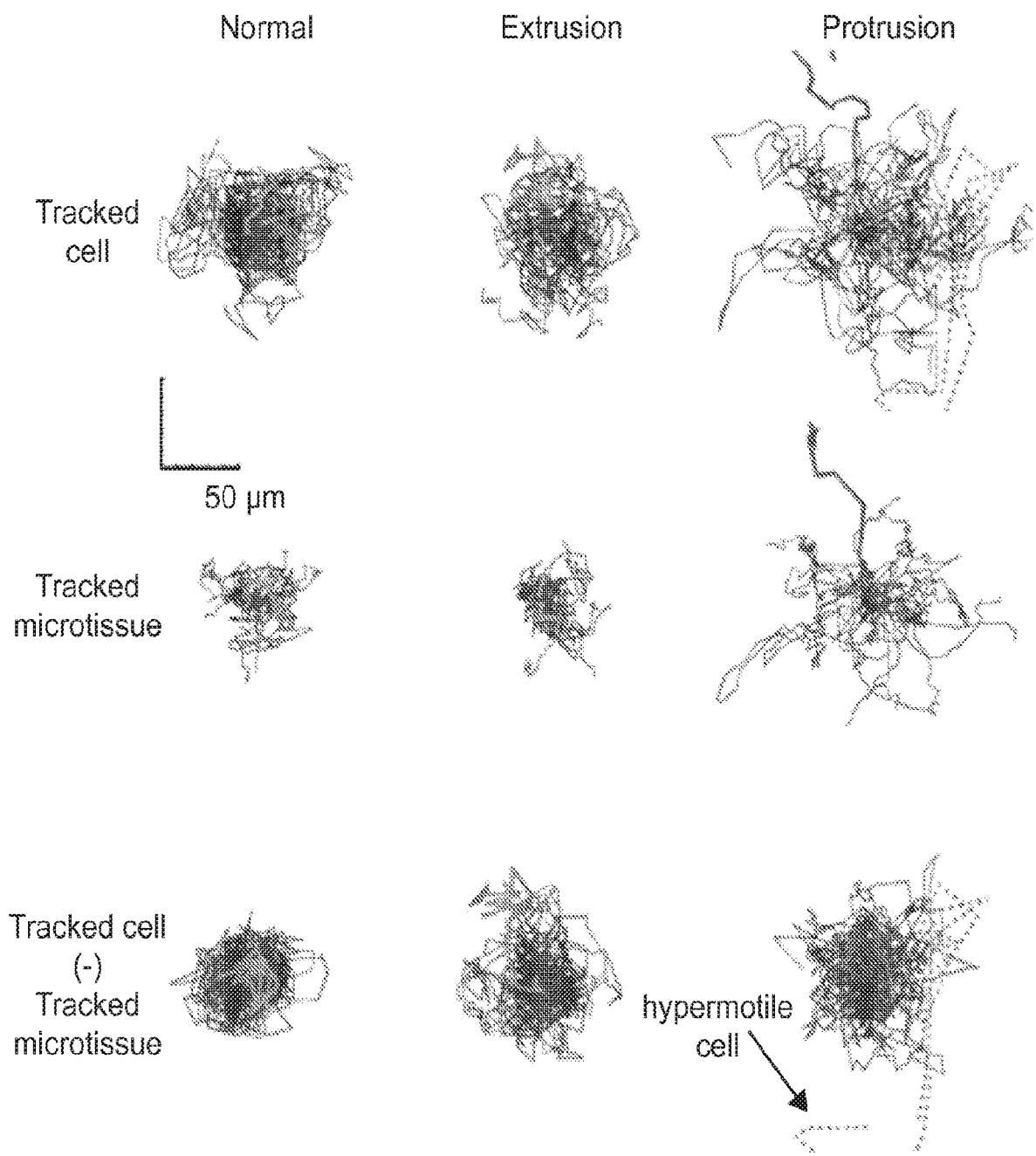

FIG. 30 shows tracking data for H2B-GFP-expressing MCF10ARas cells in WT microtissues exhibiting normal, basal extruding, or motile multicellular protrusion phenotypes. (Top row) Thirty superimposed cell tracks for the three phenotypes described in FIG. 27, Panels A-E and FIG. 29, Panels A-E. A single representative track is highlighted in red. (Middle Row) Thirty superimposed tracks following the centroid of the surrounding WT microtissue. (Bottom Row) Residual tracks generated by subtracting the WT microtissue track from the track of the corresponding MCF10ARas cell. A track from a cell exhibiting the hypermotile phenotype is indicated by the dashed red line in the protrusion trajectories. Trajectories are bounded by a 100 μm radius.

DETAILED DESCRIPTION

The present disclosure provides membrane anchored polynucleotides, and compositions comprising the membrane anchored polynucleotides. Also provided are methods for the synthesis of the membrane anchored polynucleotides, compositions comprising such membrane anchored polynucleotides, and the use of such membrane anchored polynucleotides and compositions thereof in certain therapeutic and research applications, including certain applications relating to controlling cellular adhesion.

Before exemplary embodiments of the present invention are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and exemplary methods and materials may now be described. Any and all publications mentioned herein are incorporated herein by reference to disclose and describe the methods and/or materials in connection with which the publications are cited. It is understood that the present disclosure supersedes any disclosure of an incorporated publication to the extent there is a contradiction.

It must he noted that as used herein and in the appended claims, the singular forms "a", "an", and "the" include plural referents unless the context clearly dictates otherwise. Thus, for example, reference to "a membrane anchored polynucleotide" includes a plurality of such membrane-anchored polynucleotides and reference to "the polynucleotide" includes reference to one or more polynucleotides, and so forth.

It is further noted that the claims may be drafted to exclude any element which may be optional. As such, this statement is intended to serve as antecedent basis for use of such exclusive terminology as "solely", "only" and the like in connection with the recitation of claim elements, or the use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may he different from the actual publication dates which may need to be independently confirmed. To the extent such publications may set out definitions of a term that conflicts with the explicit or implicit definition of the present disclosure, the definition of the present disclosure controls.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can he carried out in the order of events recited or in any other order which is logically possible.

Definitions

The terms "membrane-anchored polynucleotide" and "membrane anchored polynucleotide," "lipid-DNA" and similar terms are to be broadly construed to include any oligonucleotide or polynucleotide that is attached by any means to a hydrophobic, lipophilic, or amphiphilic region that can be inserted into a membrane, regardless of whether the "membrane-anchored polynucleotide" or portion thereof is actually inserted into a membrane.

The term "membrane" or any similar term is used broadly and generically herein to refer to any lipid-containing membrane, cellular membrane, monolayer, bilayer, vesicle, liposome, lipid bilayer, etc., and the present invention is not meant to be limited to any particular membranes.

The particular use of terms "nucleic acid," "oligonucleotide," and "polynucleotide" should in no way be considered limiting and may be used interchangeably herein. "Oligonucleotide" is used when the relevant nucleic acid molecules typically comprise less than about 100 bases. "Polynucleotide" is used when the relevant nucleic acid molecules typically comprise more than about 100 bases. Both terms are used to denote DNA, RNA, modified or synthetic DNA or RNA (including, but not limited to nucleic acids comprising synthetic and naturally-occurring base analogs, dideoxy or other sugars, thiols or other non-natural or natural polymer backbones), or other nucleobase containing polymers. Accordingly, the terms should not be construed to define or limit the length of the nucleic acids referred to and used herein.

Polynucleotides of the present disclosure may be single-stranded, double-stranded, triple-stranded, or include a combination of these conformations. Generally polynucleotides contain phosphodiester bonds, although in some cases, as outlined below, nucleic acid analogs are included that may have alternate backbones, comprising, for example, phosphoramide, phosphorothioate, phosphorodithioate, O-methylphophoroamidite linkages, and peptide nucleic acid backbones and linkages. Other analog nucleic acids include morpholinos, as well as those with positive backbones, non-ionic backbones, and non-ribose backbones. Nucleic acids containing one or more carbocyclic sugars are also included within the definition of nucleic acids. These modifications of the ribose-phosphate backbone may be done to facilitate the addition of additional moieties such as labels, or to increase the stability and half-life of such molecules in physiological environments.

The term "nucleic acid sequence" or "polynucleotide sequence" refers to a contiguous string of nucleotide bases and in particular contexts also refers to the particular placement of nucleotide bases in relation to each other as they appear in a polynucleotide.

The terms "complementary" or "complementarity" refer to polynucleotides (i.e., a sequence of nucleotides) related by base-pairing rules, For example, the sequence "5'-AGT-3'," is complementary to the sequence "5'-ACT-3'". Complementarity may be "partial," in which only some of the nucleic acids' bases are matched according to the base pairing rules, or there may be "complete" or "total" complementarity between the nucleic acids. The degree of complementarity between nucleic acid strands can have significant effects on the efficiency and strength of hybridization between nucleic acid strands under defined conditions. This is of particular importance for methods that depend upon binding between nucleic acids.

As used herein, the term "hybridization" is used in reference to the pairing of complementary nucleic acids. Hybridization and the strength of hybridization(i.e., the strength of the association between the nucleic acids) is influenced by such factors as the degree of complementary between the nucleic acids, stringency of the conditions involved, and the $T_m$ of the formed hybrid. "Hybridization" methods involve the annealing of one nucleic acid to another, complementary nucleic acid, i.e., a nucleic acid having a complementary nucleotide sequence.

Hybridization is carried out in conditions permitting specific hybridization. The length of the complementary sequences, the secondary structure, and GC content affects the thermal melting point $T_m$ of the hybridization conditions necessary for obtaining specific hybridization of the target site to the target nucleic acid. Hybridization may be carried out under stringent conditions. The phrase "stringent hybridization conditions" refers to conditions under which a probe will hybridize to its target subsequence, typically in a complex mixture of nucleic acid, but to no other sequences at a detectable or significant level. Stringent conditions are sequence-dependent and will be different in different circumstances. Stringent conditions are those in which the salt concentration is less than about 1.0 M sodium ion, such as less than about 0.01 M, including from about 0.001 M to about 1.0 M sodium ion concentration (or other salts) at a pH between about 6 to about 8 and the temperature is in the range of about 20° C. to about 65° C. Stringent conditions may also be achieved with the addition of destabilizing agents, such as but not limited to formamide.

The terms "thermal melting point", "melting temperature" or "$T_m$" refer herein to the temperature (under defined ionic strength, pH, and nucleic acid concentration) at which 50% of probes complementary to a target hybridize to the target sequence at equilibrium (as the target sequences are present in excess, at $T_m$, 50% of the probes are occupied at equilibrium). In some cases, the term "$T_d$" is used to define the temperature at which at least half of a probe dissociates from a perfectly matched target nucleic acid.

The formation of a duplex molecule with all perfectly formed hydrogen-bonds between corresponding nucleotides is referred as "matched" or "perfectly matched", and duplexes with single or several pairs of nucleotides that do not correspond are referred to as "mismatched." Any combination of single-stranded RNA or DNA molecules can form duplex molecules (DNA:DNA, DNA:RNA, RNA:DNA, or RNA:RNA) under appropriate experimental conditions.

The phrase "selectively (or specifically) hybridizing" refers to the binding, duplexing, or hybridizing of a molecule only to a particular nucleotide sequence under stringent hybridization conditions when that sequence is present in a complex mixture (e.g. total cellular or library DNA or RNA).

Those of ordinary skill in the art will readily recognize that alternative hybridization and wash conditions can be utilized to provide conditions of similar stringency and will recognize that the combination of parameters is much more important than the measure of any single parameter.

The term "fluorophore" refers to any molecular entity that is capable of absorbing energy of a first wavelength and re-emit energy at a different second wavelength. Exemplary fluorophores include, but are not limited to CAL Fluor Red 610 (FR610; Biosearch Technologies, Novato, Calif.), fluorescein isothiocyanate, fluorescein, thodamine and rhodamine derivatives, coumarin and coumarin derivatives, cyanine and cyanine derivatives, Alexa Fluors (Molecular Probes, Eugene, Oreg.), DyLight Fluors (Thermo Fisher Scientific, Waltham, Mass.), and the like.

The terms "optional" or "optionally" as used herein mean that the subsequently described circumstance may or may not occur, so that the description includes instances where the circumstance occurs and instances where it does not. For example, the phrase "optionally substituted" means that a non-hydrogen substituent may or may not be present, and, thus, the description includes structures wherein a non-hydrogen substituent is present and structures wherein a non-hydrogen substituent is not present.

"Analyte" refers to a substance or chemical constituent that is determined in an analytical or qualitative detection procedure, such as a titration, immunoassay, chromatography, spectrophotometry, thermography and the like. An analyte itself typically cannot be measured, but a measurable property of the analyte can. For instance, typical properties measured or detected are concentration, optical absorbance, molecular weight, melting temperature, binding properties, biological activity, and so forth.

"Pharmaceutical agent" refers to an agent that finds use in the testing, development or application as a pharmaceutical, including nutraceuticals.

"Therapeutic agent" refers to an agent that finds use in the testing, development or application as a therapeutic, including pharmaceutical agents.

"Imaging agent" refers to an agent that finds use in locating the position of a lipid particle in an animal, including: optical agents, ultrasound contrast agents, high mass X-ray contrast agents, radioactive, imaging agents or nuclear magnetic imaging agents.

"Cosmetic agent" refers to an agent that finds use in the testing, development or application as a cosmetic.

The terms "therapeutically acceptable", "pharmaceutically acceptable" and "cosmetically acceptable" refer to a material that is not biologically or otherwise undesirable, i.e., the material is of an acceptable quality and composition that may be administered to an individual along with the selected active ingredient without causing any undesirable biological effects or interacting in a deleterious manner with any of the other components of the composition in which it is contained.

The term "bilayer" refers to a "sandwich-like" structure composed of amphiphilic lipid molecules (often phospholipids) that are arranged as two molecular layers with the hydrophobic tails on the inside and the polar head groups on the outside surfaces.

The term "monolayer" refers to a structure defined by a molecular layer of amphipathic molecules with the head groups enriched and substantially aligned on one side and hydrophobic groups enriched and substantially on the opposite side.

The term "physiological conditions" is meant to encompass those conditions compatible with living cells, e.g., predominantly aqueous conditions of a temperature, pH, salinity, etc. that are compatible with living cells.

The terms "therapeutic composition", "pharmaceutical composition", "cosmetic compositions", "therapeutic preparation", "pharmaceutical preparation" or "cosmetic preparation" are meant to encompass a composition suitable for application or administration to a subject, such as a mammal, especially a human. In general such composition is safe, usually sterile, and preferably free of contaminants that are capable of eliciting an undesirable response of the subject (e.g., the compound(s) in the composition is of an acceptable grade for a given end use). Compositions can be designed for application or administration to subjects or patients in need thereof via a number of different routes of administration including topical, oral, buccal, rectal, parenteral, subcutaneous, intravenous, intraperitoneal, intradermal, intratracheal, intrathecal, pulmonary, and the like. In some embodiments the composition is suitable for application or administration by a transdermal route. In other embodiments, the compositions are suitable for application or administration by a route other than transdermal administration.

As used herein, the terms "determining," "measuring," and "assessing," and "assaying" are used interchangeably and include both quantitative and qualitative determinations.

The term "substantially similar" as used in the context of nucleic acid or amino acid sequence identity refers to two or more sequences which have at least about 50%, at least about 60%, at least about 70%, at least about 75%, at least about 80%, at least about 85%, at least about 90%, at least about 95%, at least about 98%, at least about 99%, or 100% sequence identity.

As used herein "% sequence identity" is determined using the EMBOSS Pairwise Alignment Algorithms tool available from The European Bioinformatics Institute (EMBL-EBI), which is part of the European Molecular Biology Laboratory (EMBL). This tool is accessible at the website located by placing "www," in front of "ebi.ac.uk/Tools/emboss/align/". This tool utilizes the Needleman-Wunsch global alignment algorithm (Needleman, S. B. and Wunsch, C. D. (1970) J. Mol. Biol. 48, 443-453; Kruskal, J. B. (1983) An overview of sequence comparison In D. Sankoff and B. Kruskal, (ed.), Time warps, string edits and macromolecules: the theory and practice of sequence comparison, pp. 1-44 Addison Wesley. Default settings are utilized which include Gap Open: 10.0 and Gap Extend 0.5. The default matrix "Blosum62" is utilized for amino acid sequences and the default matrix "DNAfull" is utilized for nucleic acid sequences.

Throughout the present disclosure, the nomenclature used to describe the membrane-anchored polynucleotides is as follows. First, conventional names are used for certain membrane-anchored portions of the compounds, such as dialkylphosphoglycieride, and monoalkylamide. Second, for the convenience of description, the following acronyms may be utilized: FACS, Fluorescence Activated Cell Sorting; DNA, Deoxyribonucleic Acids; DIFO, Difluorocyclooctyne; NHS, N-hydroxysuccinimide; PEG, polyethylene glycol; MFI median fold fluorescence increase; dT, deoxythymidine; MEF, mouse embryonic fibroblast; PBS, phosphate buffered saline; TEAA, triethylammonium acetate; HPLC, high pressure liquid chromatography; P/I, phorbol-12-myristate-13-acetate (PMA) and ionomycin; FITC, fluoroscein isothiocyanate.

Introduction

The present disclosure provides compositions and compounds comprising membrane anchored polynucleotides. The disclosure also provides methods for the production of such membrane anchored polynucleotides and compositions that contain them. The disclosure also provides methods of using membrane anchored polynucleotides, as well as kits comprising one or more membrane anchored polynucleotides and/or compositions.

The compounds and compositions of the invention can be adapted for a variety of applications that find, or benefit by, the use of membrane anchored polynucleotides, for instance, as therapeutic and imaging agents themselves, to facilitate delivery of therapeutics, detectable labels, and other agents of interest, to enable tissue engineering, high-throughput screening of non-adherent cells, facilitate cell-based therapies, and improve wound healing. The membrane-anchored polynucleotides can also be designed so as facilitate the delivery of drugs, as will be described in more detail below.

Membrane-Anchored Polynucleotides

The present disclosure provides membrane-anchored polynucleotides, as well as compositions comprising membrane-anchored polynucleotides. The compositions of the present disclosure typically comprise polynucleotides comprising a membrane anchoring region that can insert into a membrane.

Figure 1:
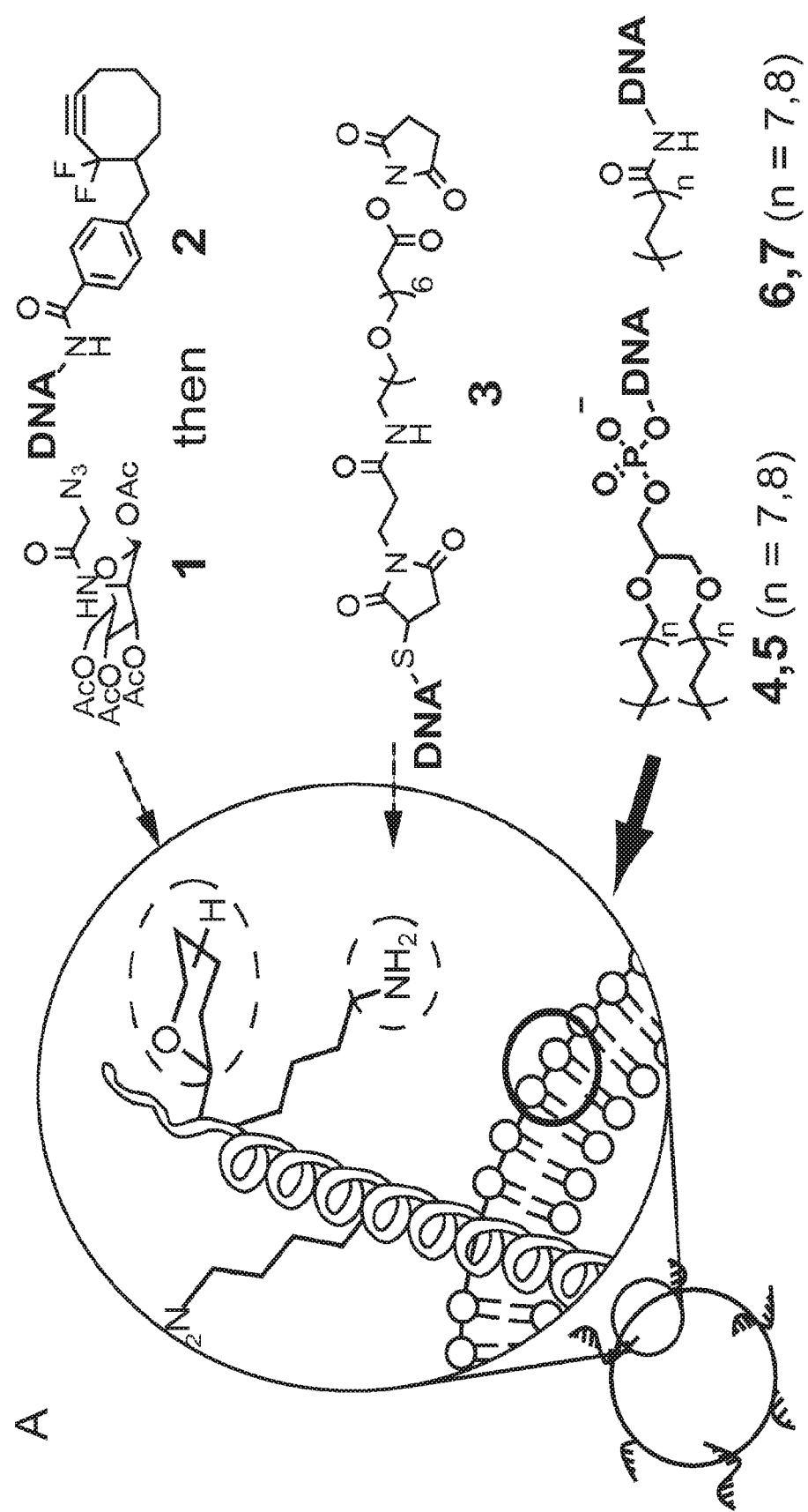
FIG. 1, Panels A-B depict various strategies for modifying a membrane with polynucleotides. Panel A: Examples of strategies for modifying a membrane with polynucleotides. Cell surface glycans are targeted for chemical remodeling following a three-day incubation in azido sugar and subsequent covalent modification with DIFO (2) conjugated polynucleotides. Protein lysine side chains are conjugated to NHS-ester modified polynucleotides (3). Fatty acid amides (6, 7) and dialkylphosphoglyceride-modified polynucleotides ($C_{16}$ dialkylphosphoglyceride=4, $C_{18}$ dialkylphosphoglyceride=5) modify the lipid bilayer independent of cell surface proteins and glycans. Panel B: A depiction of one possible structure of a membrane anchored polynucleotide.
Figure 1:
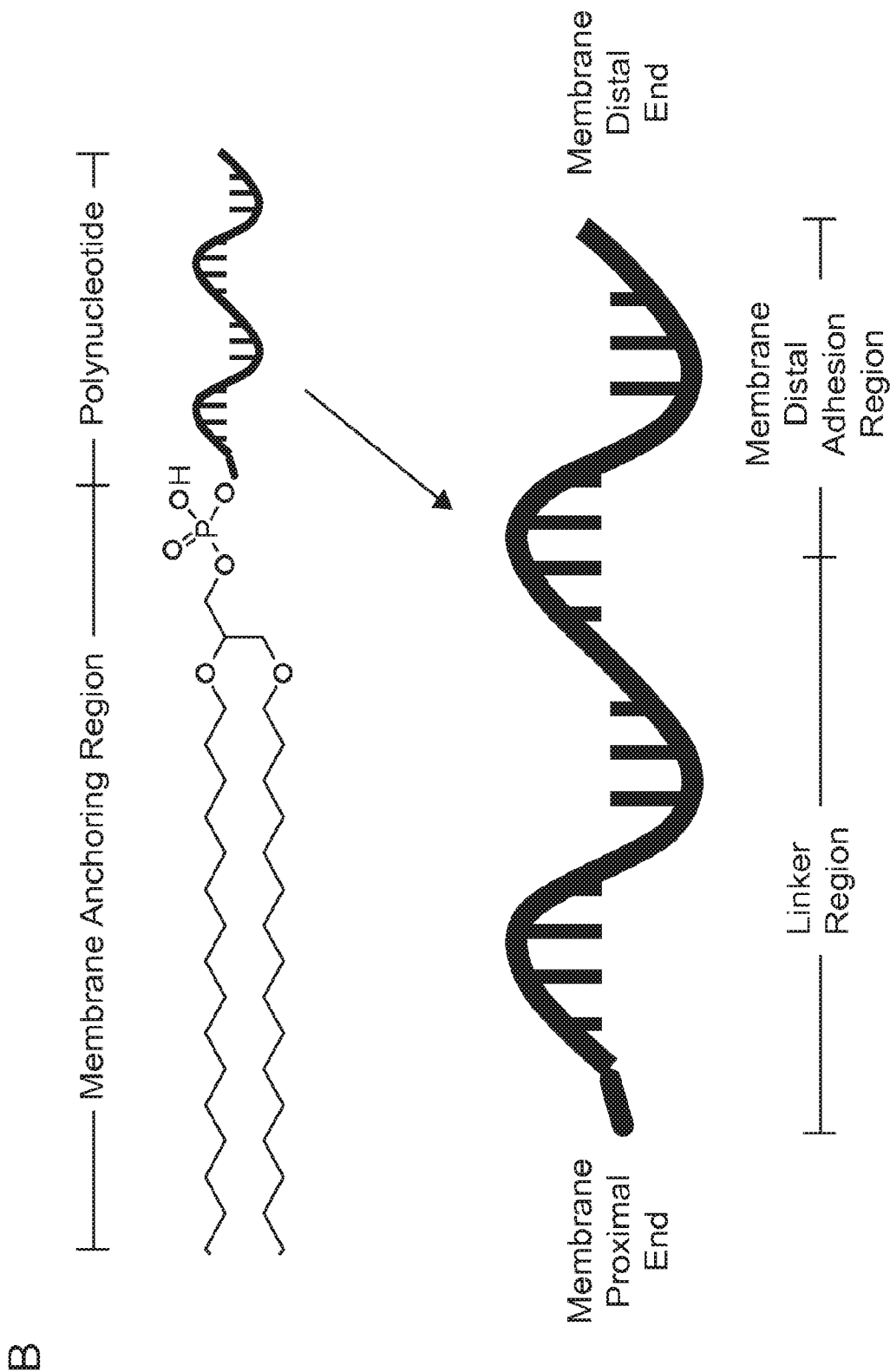

One general and non-limiting example of a membrane anchored polynucleotide is presented in FIG. 1, Panel B. This membrane anchored polynucleotide comprises a membrane anchored region, and a polynucleotide. The polynucleotide has a membrane proximal end, and a membrane distal end. As described herein, the polynucleotide may comprise a linker region and a membrane distal adhesion region. A linker region of a polynucleotide may comprise a contiguous stretch of at least about 20 nucleotides. A membrane distal adhesion region may comprise at least 10 nucleotides and be positioned distal to the linker region, wherein the linker region is not hybridizable to the membrane distal adhesion region.

Polynucleotides

The polynucleotide portion of a membrane-anchored polynucleotide typically comprises DNA, most typically a single stranded DNA. In some embodiments, the polynucleotide may comprise RNA. In some embodiments, the polynucleotide may be single-stranded.

Regardless of whether the 5' or 3' end of the polynucleotide is affixed closer to the membrane anchoring region, the end of the polynucleotide that is closer to the membrane anchoring region is considered to be the "membrane proximal end," whereas the other end of the polynucleotide is considered to be the "membrane distal end," unless the context clearly dictates otherwise. Moreover, if some A is "proximal" to some B, it is to be understood that A is closer to the membrane proximal end than is B. Similarly, if some A is "distal" to some B, it is to be understood that A is closer to the membrane distal end than is B.

A polynucleotide often comprises a linker region and a membrane distal adhesion region, wherein the linker region is closer to the membrane proximal end of the polynucleotide than is the membrane distal adhesion region. A polynucleotide may include a membrane proximal adhesion region, described in greater detail herein.

The polynucleotide may be naturally occurring, or isolated from a naturally occurring source. In other embodiments, the polynucleotide may be synthesized or synthetic. In certain embodiments, the polynucleotide may be chimeric or heterologous.

A polynucleotide may be attached to a membrane anchoring region at either its 5' end or 3' end, or attached at a position that is at neither end. In some embodiments, the polynucleotide is attached directly to the membrane anchoring region, such as by conjugation. When not directly attached to the membrane anchoring region, the polynucleotide may be separated from the membrane anchoring region by one or more atoms, most typically between one and 10 atoms, more typically between 1 and 8 atoms, more typically between 1 and 5 atoms.

In certain embodiments, the polynucleotide may contain adenine, guanine, cytosine, thymine, or uracil. In other embodiments, the polynucleotide may contain other bases, including non-natural bases.

In some embodiments, the poly-nucleotide comprises between about 5 and 3000 nucleotides. In other embodiments, the polynucleotide comprises about 5 to 10 nucleotides, about 10 to 20 nucleotides, about 20 to 40 nucleotides, about 40 to 60 nucleotides, about 60 to 80 nucleotides, about 80 to 100 nucleotides, about 100 to 120 nucleotides, about 120 to 140 nucleotides, about 140 to 160 nucleotides, about 160 to 180 nucleotides, about 180 to 200 nucleotides, about 200 to 225 nucleotides, about 225 to 250 nucleotides, about 250 to 275 nucleotides, about 275 to about 300 nucleotides, about 300 to 350 nucleotides, about 350 to 400 nucleotides, about 450 to 500 nucleotides, about 500 to 600 nucleotides, about 600 to 700 nucleotides, about 700 to 800 nucleotides, about 800 to 900 nucleotides, about 1000 to 1200 nucleotides, about 1200 to 1400 nucleotides, about 1400 to 1600 nucleotides, about 1600 to 1800 nucleotides, about 1800 to 2000 nucleotides, about 2000 to 2250 nucleotides, about 2250 to 2500 nucleotides, about 2500 to 2750 nucleotides, about 2750 to 3000 nucleotides or more.

Linker Region

A polynucleotide may comprise a linker region, wherein the linker region comprises a contiguous stretch of about 20 to about 3000 nucleotides. In many embodiments, the linker region is separated from the membrane distal end of the polynucleotide by about 10 nucleotides or more. In many embodiments, the linker region is separated from the membrane distal end of the polynucleotide by about 10 to 2000 nucleotides or more. In some embodiments, the linker region is separated from the membrane distal end by about 5 to 10 nucleotides, about 10 to 20 nucleotides, about 20 to 40 nucleotides, about 40 to 60 nucleotides, about 60 to 80 nucleotides, about 80 to 100 nucleotides, about 100 to 120 nucleotides, about 120 to 140 nucleotides, about 140 to 160 nucleotides, about 160 to 180 nucleotides, about 180 to 200 nucleotides, about 200 to 225 nucleotides, about 225 to 250 nucleotides, about 250 to 275 nucleotides, about 275 to about 300 nucleotides, about 300 to 350 nucleotides, about 350 to 400 nucleotides, about 450 to 500 nucleotides, about 500 to 600 nucleotides, about 600 to 700 nucleotides, about 700 to 800 nucleotides, about 800 to 900 nucleotides, about 1000 to 1200 nucleotides, about 1200 to 1400 nucleotides, about 1400 to 1600 nucleotides, about 1600 to 1800 nucleotides, about 1800 to 2000 nucleotides.

In many embodiments, the linker region comprises a contiguous stretch of about 5 to 3000 identical nucleotides. In some embodiments, the linker region comprises a contiguous stretch of about 10 to 2000 nucleotides comprising only two types of bases. In some embodiments, the linker region does not hybridize with any contiguous stretch of at least about 10 nucleotides that are distal to the linker region in the polynucleotide. In some embodiments, the linker region does not hybridize with any contiguous stretch of about 10 to 500 nucleotides that are distal to the linker region in the polynucleotide.

In certain embodiments, the linker region comprises a contiguous stretch of about 5 to 3000 identical nucleotides. In some embodiments, the contiguous stretch comprises about 5 to 10 nucleotides, about 10 to 20 nucleotides, about 20 to 40 nucleotides, about 40 to 60 nucleotides, about 60 to 80 nucleotides, about 80 to 100 nucleotides, about 100 to 120 nucleotides, about 120 to 140 nucleotides, about 140 to 160 nucleotides, about 160 to 180 nucleotides, about 180 to 200 nucleotides, about 200 to 225 nucleotides, about 225 to 250 nucleotides, about 250 to 275 nucleotides, about 275 to about 300 nucleotides, about 300 to 350 nucleotides, about 350 to 400 nucleotides, about 450 to 500 nucleotides, about 500 to 600 nucleotides, about 600 to 700 nucleotides, about 700 to 800 nucleotides, about 800 to 900 nucleotides, about 1000 to 1200 nucleotides, about 1200 to 1400 nucleotides, about 1400 to 1600 nucleotides, about 1600 to 1800 nucleotides, about 1800 to 2000 nucleotides, about 2000 to 2250 nucleotides, about 2250 to 2500 nucleotides, about 2500 to 2750 nucleotides, about 2750 to 3000 nucleotides or more. In particular embodiments, the contiguous stretch comprises thymine nucleotides. In other embodiments, the contiguous stretch comprises adenine nucleotides. In still other embodiments, the contiguous stretch comprises cytosine nucleotides. In still other embodiments, the contiguous stretch comprises guanine nucleotides. In yet other embodiments, the contiguous stretch comprises uracil nucleotides.

In particular embodiments, the contiguous stretch begins at the membrane proximal end of the polynucleotide. In other embodiments, it is separated from the membrane proximal end by 1 or more nucleotides. In certain embodiments, it is separated from the membrane proximal end by about 5 to about 3000 nucleotides. In particular embodiments, it is separated from the membrane proximal end by about 5 to 10 nucleotides, about 10 to 20 nucleotides, about 20 to 40 nucleotides, about 40 to 60 nucleotides, about 60 to 80 nucleotides, about 80 to 100 nucleotides, about 100 to 120 nucleotides, about 120 to 140 nucleotides, about 140 to 160 nucleotides, about 160 to 180 nucleotides, about 180 to 200 nucleotides, about 200 to 225 nucleotides, about 225 to 250 nucleotides, about 250 to 275 nucleotides, about 275 to about 300 nucleotides, about 300 to 350 nucleotides, about 350 to 400 nucleotides, about 450 to 500 nucleotides, about 500 to 600 nucleotides, about 600 to 700 nucleotides, about 700 to 800 nucleotides, about 800 to 900 nucleotides, about 1000 to 1200 nucleotides, about 1200 to 1400 nucleotides, about 1400 to 1600 nucleotides, about 1600 to 1800 nucleotides, about 1800 to 2000 nucleotides, about 2000 to 2250 nucleotides, about 2250 to 2500 nucleotides, about 2500 to 2750 nucleotides, about 2750 to 3000 nucleotides or more.

In certain embodiments, the polynucleotide comprises a contiguous stretch of about 10 to 2000 nucleotides comprising only two types of bases. In some embodiments, the two bases are adenine and cytosine. In other embodiments, the two bases are adenine and guanine. In other embodiments, the two bases are adenine and thymine. In other embodiments, the two bases are adenine and uracil. In other embodiments, the two bases are cytosine and guanine. In still other embodiments, the two bases are cytosine and thymine. In still other embodiments, the two bases are cytosine and uracil. In other embodiments, the two bases are guanine and thymine. In other embodiments, the two bases are guanine and uracil. In certain embodiments, the contiguous stretch comprises about 10 to 20 nucleotides, about 20 to 40 nucleotides, about 40 to 60 nucleotides, about 60 to 80 nucleotides, about 80 to 100 nucleotides, about 100 to 120 nucleotides, about 120 to 140 nucleotides, about 140 to 160 nucleotides, about 160 to 180 nucleotides, about 180 to 200 nucleotides, about 200 to 225 nucleotides, about 225 to 250 nucleotides, about 250 to 275 nucleotides, about 275 to about 300 nucleotides, about 300 to 350 nucleotides, about 350 to 400 nucleotides, about 450 to 500 nucleotides, about 500 to 600 nucleotides, about 600 to 700 nucleotides, about 700 to 800 nucleotides, about 800 to 900 nucleotides, about 1000 to 1200 nucleotides, about 1200 to 1400 nucleotides, about 1400 to 1600 nucleotides, about 1600 to 1800 nucleotides, about 1800 to 2000 nucleotides or more.

In particular embodiments, the contiguous stretch comprising only two types of bases begins at the membrane proximal end of the polynucleotide. In other embodiments, it is separated from the membrane proximal end by 1 or more nucleotides. In certain embodiments, it is separated from the membrane proximal end by about 5 to about 3000 nucleotides. In particular embodiments, it is separated from the membrane proximal end by about 5 to 10 nucleotides, about 10 to 20 nucleotides, about 20 to 40 nucleotides, about 40 to 60 nucleotides, about 60 to 80 nucleotides, about 80 to 100 nucleotides, about 100 to 120 nucleotides, about 120 to 140 nucleotides, about 140 to 160 nucleotides, about 160 to 180 nucleotides, about 180 to 200 nucleotides, about 200 to 225 nucleotides, about 225 to 250 nucleotides, about 250 to 275 nucleotides, about 275 to about 300 nucleotides, about 300 to 350 nucleotides, about 350 to 400 nucleotides, about 450 to 500 nucleotides, about 500 to 600 nucleotides, about 600 to 700 nucleotides, about 700 to 800 nucleotides, about 800 to 900 nucleotides, about 1000 to 1200 nucleotides, about 1200 to 1400 nucleotides, about 1400 to 1600 nucleotides, about 1600 to 1800 nucleotides, about 1800 to 2000 nucleotides, about 2000 to 2250 nucleotides, about 2250 to 2500 nucleotides, about 2500 to 2750 nucleotides, about 2750 to 3000 nucleotides or more.

In certain embodiments, the polynucleotide comprises a contiguous stretch of about 10 to 2000 nucleotides comprising only three types of bases. In some embodiments, the three bases are selected from A, C, T, and G. In certain embodiments, the three bases are A, C, and T.

Membrane Distal Adhesion Region

In most embodiments, the polynucleotide region distal to the linker region and before the membrane distal end comprises a membrane distal adhesion region. The membrane distal adhesion region may hybridize to a polynucleotide, fluorophore, or pharmaceutical composition. The membrane distal adhesion region may hybridize to a polynucleotide present in another membrane anchored polynucleotide. Such hybridization may be between the membrane distal adhesion regions of the two membrane anchored polynucleotides. Such hybridization may be strict hybridization.

In certain embodiments, the sequence of the membrane distal adhesion region does not hybridize with any other region of the polynucleotide. In certain embodiments, the membrane distal adhesion region comprises about 5 to about 3000 nucleotides. In particular embodiments, it comprises 5 to 10 nucleotides, about 10 to 20 nucleotides, about 20 to 40 nucleotides, about 40 to 60 nucleotides, about 60 to 80 nucleotides, about 80 to 100 nucleotides, about 100 to 120 nucleotides, about 120 to 140 nucleotides, about 140 to 160 nucleotides, about 160 to 180 nucleotides, about 180 to 200 nucleotides, about 200 to 225 nucleotides, about 225 to 250 nucleotides, about 250 to 275 nucleotides, about 275 to about 300 nucleotides, about 300 to 350 nucleotides, about 350 to 400 nucleotides, about 450 to 500 nucleotides, about 500 to 600 nucleotides, about 600 to 700 nucleotides, about 700 to 800 nucleotides, about 800 to 900 nucleotides, about 1000 to 1200 nucleotides, about 1200 to 1400 nucleotides, about 1400 to 1600 nucleotides, about 1600 to 1800 nucleotides, about 1800 to 2000 nucleotides, about 2000 to 2250 nucleotides, about 2250 to 2500 nucleotides, about 2500 to 2750 nucleotides, about 2750 to 3000 nucleotides or more.

The membrane distal adhesion region may comprise $(CAGT)_n$ and/or $(ACTG)_n$, where n is an integer equal to or greater than 1. In some embodiments, n is 1. In other embodiments, n is between 1 and 20. In certain embodiments, n is between 1 and 10, or more preferably between 1 and 5.

Membrane Proximal Adhesion Region

In many embodiments, the region proximal to the linker region comprises a membrane proximal adhesion region. In certain embodiments, the sequence of the membrane proximal adhesion region does not hybridize with any other region of the polynucleotide. In certain embodiments, the sequence of the membrane proximal adhesion region does not hybridize with any other region of the polynucleotide. In certain embodiments, the membrane proximal adhesion region comprises about 5 to about 3000 nucleotides. In particular embodiments, it comprises 5 to 10 nucleotides, about 10 to 20 nucleotides, about 20 to 40 nucleotides, about 40 to 60 nucleotides, about 60 to 80 nucleotides, about 80 to 100 nucleotides, about 100 to 120 nucleotides, about 120 to 140 nucleotides, about 140 to 160 nucleotides, about 160 to 180 nucleotides, about 180 to 200 nucleotides, about 200 to 225 nucleotides, about 225 to 250 nucleotides, about 250 to 275 nucleotides, about 275 to about 300 nucleotides, about 300 to 350 nucleotides, about 350 to 400 nucleotides, about 450 to 500 nucleotides, about 500 to 600 nucleotides, about 600 to 700 nucleotides. about 700 to 800 nucleotides, about 800 to 900 nucleotides, about 1000 to 1200 nucleotides, about 1200 to 1400 nucleotides, about 1400 to 1600 nucleotides, about 1600 to 1800 nucleotides, about 1800 to 2000 nucleotides, about 2000 to 2250 nucleotides, about 2250 to 2500 nucleotides, about 2500 to 2750 nucleotides, about 2750 to 3000 nucleotides or more.

In some embodiments, the membrane proximal adhesion region comprises $(CAGT)_n$ and/or $(ACTG)_n$, where n is an integer equal to or greater than 1. In some embodiments, n is 1. In other embodiments, n is between 1 and 20. In certain embodiments, n is between 1 and 10, or more preferably between 1 and 5. In other embodiments, the membrane proximal adhesion region comprises GTAACGATCCAGCTGTCACT (SEQ ID NO: 1), GATCCAGCTGTCACT (SEQ ID NO: 2), AGCTGTCACT (SEQ ID NO: 3), AGTGACAGCTGGATCGTTAC (SEQ ID NO: 4), AGTGACAGCTGGATC (SEQ ID NO: 5), or AGTGACAGCT (SEQ ID NO: 6).

Sequence of the Polynucleotide

As described herein, the specific sequence of the polynucleotide can vary based upon the specific usage and desired properties for the membrane bound polynucleotide.

In particular embodiments, the polynucleotide comprises a sequence selected from:

```
5'-GTAACGATCCAGCTGTCACT-T_x(CAGT)_5-3',     (SEQ ID NO: 7)

5'-GATCCAGCTGTCACT-T_x(CAGT)_5-3',          (SEQ ID NO: 8)

5'-AGCTGTCACT-T_x(CAGT)_5-3',               (SEQ ID NO: 9)

5'-T_60(ACTG)_5-3',                          (SEQ ID NO: 10)

5'-AGTGACAGCTGGATCGTTAC-3',                  (SEQ ID NO: 11)

5'-AGTGACATCTGGATC-3',                       (SEQ ID NO: 12)

5'-AGTGACAGCT-3',                            (SEQ ID NO: 13)

5'-T_x(CAGT)_5-3',                           (SEQ ID NO: 14)

5'-T_x(ACTG)_5-3',                           (SEQ ID NO: 15)
or

5'-(CAGT)_5-3',                              (SEQ ID NO: 16)
where x = 0-100.
```

The polynucleotide selected from the above may be attached to the membrane anchoring region at the 5' end. In other embodiments, the polynucleotide selected above may be attached to the membrane anchoring region at the 3' end.

In certain other embodiments, the polynucleotide comprises a sequence that hybridizes to a sequence selected from:

```
5'-GTAACGATCCAGCTGTCACT-T_x(CAGT)_5-3',     (SEQ ID NO: 7)

5'-GATCCAGCTGTCACT-T_x(CAGT)_5-3',          (SEQ ID NO: 8)

5'-AGCTGTCACT-T_x(CAGT)_5-3',               (SEQ ID NO: 9)

5'-T_60(ACTG)_5-3',                          (SEQ ID NO: 10)

5'-AGTGACAGCTGGATCGTTAC-3',                  (SEQ ID NO: 11)

5'-AGTGACATCTGGATC-3',                       (SEQ ID NO: 12)

5'-AGTGACAGCT-3',                            (SEQ ID NO: 13)

5'-T_x(CAGT)_5-3',                           (SEQ ID NO: 14)

5'-T_x(ACTG)_5-3',                           (SEQ ID NO: 15)
or

5'-(CAGT)_5-3',                              (SEQ ID NO: 16)
where x = 0-100.
```

In still other embodiments, the polynucleotide comprises a polynucleotide having at least about 75%, at least about 80%, at least about 85%, at least about 90%, at least about 95%, at least about 98%, at least about 99%, or 100%, sequence identity to a contiguous stretch of from about 10 nucleotides to about 25 nucleotides, from about 25 nucleotides to about 50 nucleotides, from about 50 nucleotides to about 75 nucleotides, from 75 nucleotides to about 100 nucleotides with a sequence selected from:

```
5'-GTAACGATCCAGCTGTCACT-T_x(CAGT)_5-3',     (SEQ ID NO: 7)

5'-GATCCAGCTGTCACT-T_x(CAGT)_5-3',          (SEQ ID NO: 8)

5'-AGCTGTCACT-T_x(CAGT)_5-3',               (SEQ ID NO: 9)

5'-T_60(ACTG)_5-3',                          (SEQ ID NO: 10)

5'-AGTGACAGCTGGATCGTTAC-3',                  (SEQ ID NO: 11)

5'-AGTGACATCTGGATC-3',                       (SEQ ID NO: 12)

5'-AGTGACAGCT-3',                            (SEQ ID NO: 13)

5'-T_x(CAGT)_5-3',                           (SEQ ID NO: 14)

5'-T_x(ACTG)_5-3',                           (SEQ ID NO: 15)
or

5'-(CAGT)_5-3',                              (SEQ ID NO: 16)
where x = 0-100.
```

In still other embodiments, the polynucleotide sequence is selected so as to hybridize with a membrane distal adhesion region of another polynucleotide. This polynucleotide may be part of a membrane anchored polynucleotide, or may be attached or affixed to, for example, a fluorophore, pharmaceutical agent, nutraceutical agent, cosmeceutical agent, imaging agent, radiopharmaceutical, nuclear magnetic resonance contrast reagent, and the like.

Such hybridization may occur over about 5 to 1000 nucleotides or more. In some embodiments, such hybridization occurs over about 5 to 10 nucleotides, about 10 to 20 nucleotides, about 20 to 40 nucleotides, about 40 to 60 nucleotides, about 60 to 80 nucleotides, about 80 to 100 nucleotides, about 100 to 120 nucleotides, about 120 to 1.40 nucleotides, about 140 to 160 nucleotides, about 160 to 180 nucleotides, about 180 to 200 nucleotides, about 200 to 225 nucleotides, about 225 to 250 nucleotides, about 250 to 275 nucleotides, about 275 to about 300 nucleotides, about 300 to 350 nucleotides, about 350 to 400 nucleotides, about 450 to 500 nucleotides, about 500 to 600 nucleotides, about 600 to 700 nucleotides, about 700 to 800 nucleotides, about 800 to 900 nucleotides, or about 900 to 1000 nucleotides or more.

In yet another embodiment, the polynucleotide sequence is selected so that at least a region of the polypeptide hybridizes with a membrane proximal adhesion region of another polynucleotide. Such hybridization may occur over about 5 to 1000 nucleotides or more. In some embodiments, such hybridization occurs over about 5 to 10 nucleotides, about 10 to 20 nucleotides, about 20 to 40 nucleotides, about 40 to 60 nucleotides, about 60 to 80 nucleotides, about 80 to 100 nucleotides, about 100 to 120 nucleotides, about 120 to 140 nucleotides, about 140 to 160 nucleotides, about 160 to 180 nucleotides, about 180 to 200 nucleotides, about 200 to 225 nucleotides, about 225 to 250 nucleotides, about 250 to 275 nucleotides, about 275 to about 300 nucleotides, about 300 to 350 nucleotides, about 350 to 400 nucleotides, about 450 to 500 nucleotides, about 500 to 600 nucleotides, about 600 to 700 nucleotides, about 700 to 800 nucleotides, about 800 to 900 nucleotides, or about 900 to 1000 nucleotides or more.

The polynucleotide sequence may also be selected so as to hybridize with any region of another polynucleotide. In certain embodiments, such hybridization occurs over about 5 to 1000 nucleotides or more. In some embodiments, such hybridization occurs over about 5 to 10 nucleotides, about 10 to 20 nucleotides, about 20 to 40 nucleotides, about 40 to 60 nucleotides, about 60 to 80 nucleotides, about 80 to 100 nucleotides, about 100 to 120 nucleotides, about 120 to 140 nucleotides, about 140 to 160 nucleotides, about 160 to 180 nucleotides, about 180 to 200 nucleotides, about 200 to 225 nucleotides, about 225 to 250 nucleotides, about 250 to 275 nucleotides, about 275 to about 300 nucleotides, about 300 to 350 nucleotides, about 350 to 400 nucleotides, about 450 to 500 nucleotides, about 500 to 600 nucleotides, about 600 to 700 nucleotides, about 700 to 800 nucleotides, about 800 to 900 nucleotides, or about 900 to 1000 nucleotides or more.

Membrane Anchoring Region

Membrane anchored polynucleotides of the current disclosure contain a membrane anchoring region, which typically comprises a long alkyl chain comprising 12-22 carbons. In most embodiments, the membrane anchoring region is attached to a polynucleotide.

In some embodiments, the membrane anchoring region is hydrophobic. In some embodiments, the membrane anchoring region is lipophilic. In some embodiments, the entire membrane anchoring region is hydrophobic. In some embodiments, the entire membrane anchoring region is lipophilic. In some embodiments, only a portion is lipophilic or hydrophobic. In some embodiments, the membrane anchoring region is amphiphilic. In many embodiments, the membrane anchoring region is such that it is energetically more favorable for the chain to be inserted into a membrane than be contained in solution (e.g. water). In many embodiments, the membrane anchoring region can spontaneously insert into a lipid membrane.

In some embodiments, the membrane anchoring region will insert into the membrane of a cell. In such embodiments, the polynucleotide attached to the membrane anchoring region will most often be on the extracellular side of the cell membrane. In certain embodiments, the polynucleotide will instead be on the intracellular side of the cell membrane.

The membrane anchoring region may comprise a single alkyl chain. In other embodiments, the membrane anchoring region comprises two alkyl chains. In certain embodiments, the membrane anchoring region comprises more than two alkyl chains. Certain embodiments may include 3 or more alkyl chains.

In some embodiments, the membrane anchoring region comprises an alkyl chain and an alkenyl, alkyl, aryl, or aralkyl chain. This alkenyl, alkyl, aryl, or aralkyl chain may comprise 12-22 carbon atoms. In some embodiments, the alkyl chain comprises about 12-22 carbon atoms, and the alkenyl, alkyl, aryl, or aralkyl chain comprises about 12-22 carbon atoms. In some embodiments, the chains share the same number of carbon atoms. In other embodiments, one chain has between about 1 and 10 fewer carbon atoms than the other chain. In some embodiments, one chain has about 1 fewer carbon atom than the other chain, about 2 fewer carbon atoms, about 3 fewer carbon atoms, about 4 fewer carbon atoms, about 5 fewer carbon atoms, about 6 fewer carbon atoms, about 7 fewer carbon atoms, about 8 fewer carbon atoms, about 9 fewer carbon atoms, or about 10 fewer carbon atoms. The membrane anchoring region may comprise more than one alkenyl, aryl, or aralkyl chain, with each chain comprising 12-22 carbon atoms.

In some embodiments, the membrane anchoring region may contain one or more unsaturated carbon bonds. In some embodiments, the unsaturated bonds are all contained within the same chain. In still other embodiments, the unsaturated bonds may be contained in more than one chain.

In certain embodiments, the membrane anchoring region comprises a dialkylphosphoglycieride, and the polynucleotide is conjugated to the dialkylphosphoglycieride. In some embodiments, each chain of the dialkylphosphoglycieride has the same number of carbon atoms with the other chain. In other embodiments, the number of carbon atoms is different between the two alkyl chains of the dialkylphosphoglycieride. In some embodiments, each chain has between 12 to 22 carbons. In some embodiments, each chain has about 12 carbon atoms, or about 14 carbon atoms, about 16 carbon atoms, about 18 carbon atoms, about 20 carbon atoms, or about 22 carbon atoms. In some embodiments, at least one chain has about 12 carbon atoms, about 14 carbon atoms, about 16 carbon atoms, about 18 carbon atoms, about 20 carbon atoms, or about 22 carbon atoms. In particular embodiments, the membrane anchoring region comprises $C_{16}$ dialkyiphosphoglyceride.

The membrane anchoring region may comprise a monoalkylamide, and the polynucleotide may be conjugated to the monoalkylamide. In some embodiments, the monoalkylamide chain has between 12 to 22 carbon atoms. In some embodiments, the monoalkylamide chain has about 12 carbon atoms, or about 14 carbon atoms, about 16 carbon atoms, about 18 carbon atoms, about 20 carbon atoms, or about 22 carbon atoms. In certain embodiments, the monoalkylamide comprises about 16 or 18 carbon atoms.

In other embodiments, the membrane anchoring region and the polynucleotide are joined by a compound comprising, a phosphate group. In other embodiments, the membrane anchoring region and the polynucleotide are joined by a compound comprising a urea group. In still other embodiments, the membrane anchoring region and the polynucleotide are joined by a compound comprising a sulfonyl group. In another embodiment, the membrane anchoring region and the polynucleotide are joined by a compound comprising a sulfonamido group.

In still other embodiments, the membrane anchoring region may comprise a sterol group. In some embodiments, the sterol group may be natural or synthetic or derived from a sterol compound bearing (or modified to bear) a functional group used for attachment to the polynucleotide. For instance, sterols from biological sources are usually found either as free sterol alcohols, acylated (sterol esters), alkylated (steryl alkyl ethers), sulfated (cholesterol sulfate), or linked to a glycoside moiety (steryl glycosides) which can be itself acylated (acylated sterol glycosides) (See, e.g., Fahy et al., *J. Lipid Research* (2005) 46:839-861, which reference is incorporated in its entirety). Examples include (1) sterols obtainable from animal sources, referred to herein "zoosterols" such as the zoosterols cholesterol and certain steroid hormones; and (2) sterols obtainable from plants, fungi and marine sources, referred to herein as "phytosterols," such as the phytosterols campesterol, sitosterol, stigmasterol, and ergosterol. These sterols generally bear at least one free hydroxyl group, usually at the 3 position of ring A, at another position, or combinations thereof, or can be modified to incorporate a suitable hydroxyl or other functional group as needed.

Sterols of particular interest are the simple sterols, which bear a unique functional group for attachment to the polynucleotide. Of specific interest are simple sterols in which the unique functional group is a hydroxyl, and in particular, the simple sterol alcohols having a hydroxyl group located at position 3 of ring A (e.g., cholesterol, β-sitosterol, stigmasterol, campesterol, and brassicasterol, ergosterol and the like, and derivatives thereof).

Cholesterol is of particular interest in certain embodiments for inclusion in the membrane anchoring region. Representative sterols of the cholesterol class (including substituted cholesterols) of interest include, for example, the following: (1) natural and synthetic sterols such as cholesterol (ovine wool), cholesterol (plant derived), desmosterol, stigmasterol, β-sitosterol, thiocholesterol, 3-cholesteryl acrylate; (2) A-ring substituted oxysterols such as cholastanol, and cholestenone; (3) B-ring substituted oxysterols such as 7-ketocholesterol, 5α,6α-epoxycholestanol, 5β,6β-epoxycholestanol, and 7-dehydrocholesterol; (4) D-ring substituted oxysterols such as 25-ketocholestene, and 15-ketocholestane; (5) side-chain substituted oxysterols such as 25-hydroxycholesterol, 27-hydroxycholesterol, 24(R/S)-hydroxycholesterol, 24(R/S),25-epoxycholesterol, and 24(S), 25-epoxycholesterol; (6) lanosterols such as 24-dihydrolanosterol and lanosterol; (7) fluorinated sterols such as F7-cholesterol, F7-5α,6α-epoxycholestanol, F7-5β,6β-epoxycholostanol, and F7-7-ketocholesterol; (8) fluorescent cholesterol such as 25-NBD cholesterol, dehydroergosterol, and cholesterol triene. These compounds may also include deuterated and non-deuterated versions, and are available commercially, such as from Avanti Polar Lipids, Inc.

In certain embodiments, the membrane anchoring region may comprise a saturated or unsaturated, linear or branched, substituted or unsubstituted aliphatic chain. Of particular interest are saturated or unsaturated, linear or branched, substituted or unsubstituted hydrocarbon chains having from 2 to 40 carbon atoms, usually from 4 to 30 carbon atoms, usually from 4 to 25 carbon atoms, more usually from 6 to 24 carbon atoms, more usually from 10 to 20 carbon atoms.

Further embodiments may comprise elements based on or derivable from various lipids, such the aliphatic acids, gycerolipids, glycerophospholipids, sphingolipids, prenol lipids, and saccharolipids, such as the from lipids described in Fahy et al., *J. Lipid Research* (2005) 46:839-861.

Compositions Comprising Membrane-Anchored Polynucleotide Compounds

The present disclosure contemplates a variety of compositions containing membrane anchored polynucleotide compounds of the present disclosure. Such compositions can he homogenous with respect to the membrane anchored polynucleotide compound, or can include one or more of the different membrane anchored polynucleotide compounds disclosed herein. Compositions having mixtures of different membrane anchored polynucleotide compounds, e.g., comprising different membrane anchoring groups, different polynucleotide sequences, etc., can provide for fine tuning of the physical properties of the compositions.

In certain embodiments, the composition comprises one membrane-anchored polynucleotide compound. In other embodiments, the composition may comprise about 2 or more membrane-anchored polynucleotide compounds. In certain embodiments, the composition may comprise about 2 to 10 membrane-anchored polynucleotide compounds, more usually from 2 to 6, more usually 2 to 4.

Compositions comprising one membrane-anchored polynucleotide compound can be said to comprise a "first compound." Compositions comprising more than one membrane-anchored polynucleotide compound can be said to comprise a "first compound," a "second compound," a "third compound," etc. as the context makes clear.

In certain embodiments, the composition comprises a first membrane-anchored polynucleotide compound comprising a membrane anchoring region comprising a long alkyl chain of at least 12 carbon atoms; and a DNA polynucleotide having a membrane distal end and a membrane proximal end, wherein said DNA polynucleotide is at least 50 nucleotides and comprises: a linker region comprising a contiguous stretch of at least about 20 nucleotides, and a membrane distal adhesion region comprising at least 10 nucleotides and positioned distal to the linker region, wherein the linker region is not hybridizable to the membrane distal adhesion region; and wherein said DNA polynucleotide is conjugated to said membrane anchoring region at the membrane proximal end. In other embodiments, this composition may also comprise a second membrane-anchored polynucleotide compound, or a third membrane-anchored polynucleotide compound, a fourth membrane-anchored polynucleotide compound, a fifth membrane-anchored polynucleotide compound, a sixth membrane-anchored polynucleotide compound, etc. Compositions may comprise about 1 to 50 membrane-anchored polynucleotides, or more.

When more than one membrane anchored polynucleotide compound is present in a composition, the membrane anchored polynucleotides may hybridize with one another. Such hybridization may occur only at a particular region, e.g. the membrane distal adhesion region. Hybridization may span occur across regions or include more than one region. In some embodiments, the full polypeptide of a first membrane anchored polynucleotide may hybridize with the full polypeptide of a second (or third, or fourth, etc.) membrane anchored polynucleotide.

Membrane Anchored Polynucleotide Duplexes

Also provided are membrane anchored polynucleotide duplexes. Membrane anchored polynucleotide duplexes are generally two membrane anchored polynucleotides that are inserted into the same membrane, and hybridize with one another over at least about 10 nucleotides. Such membrane anchored polynucleotide duplexes are often more stable in the membrane than either membrane anchored polynucleotide is individually.

The phrase 'duplex region' may be understood to refer to the region between the two membrane anchored polynucleotides that is hybridized. The duplex region is typically towards the membrane proximal end, and is typically proximal to a linker region. The duplex region is typically proximal to the membrane distal adhesion region. In certain embodiments, the duplex region itself may comprise a membrane proximal adhesion region. The duplex region typically does not include the membrane distal adhesion region.

Figure 13:
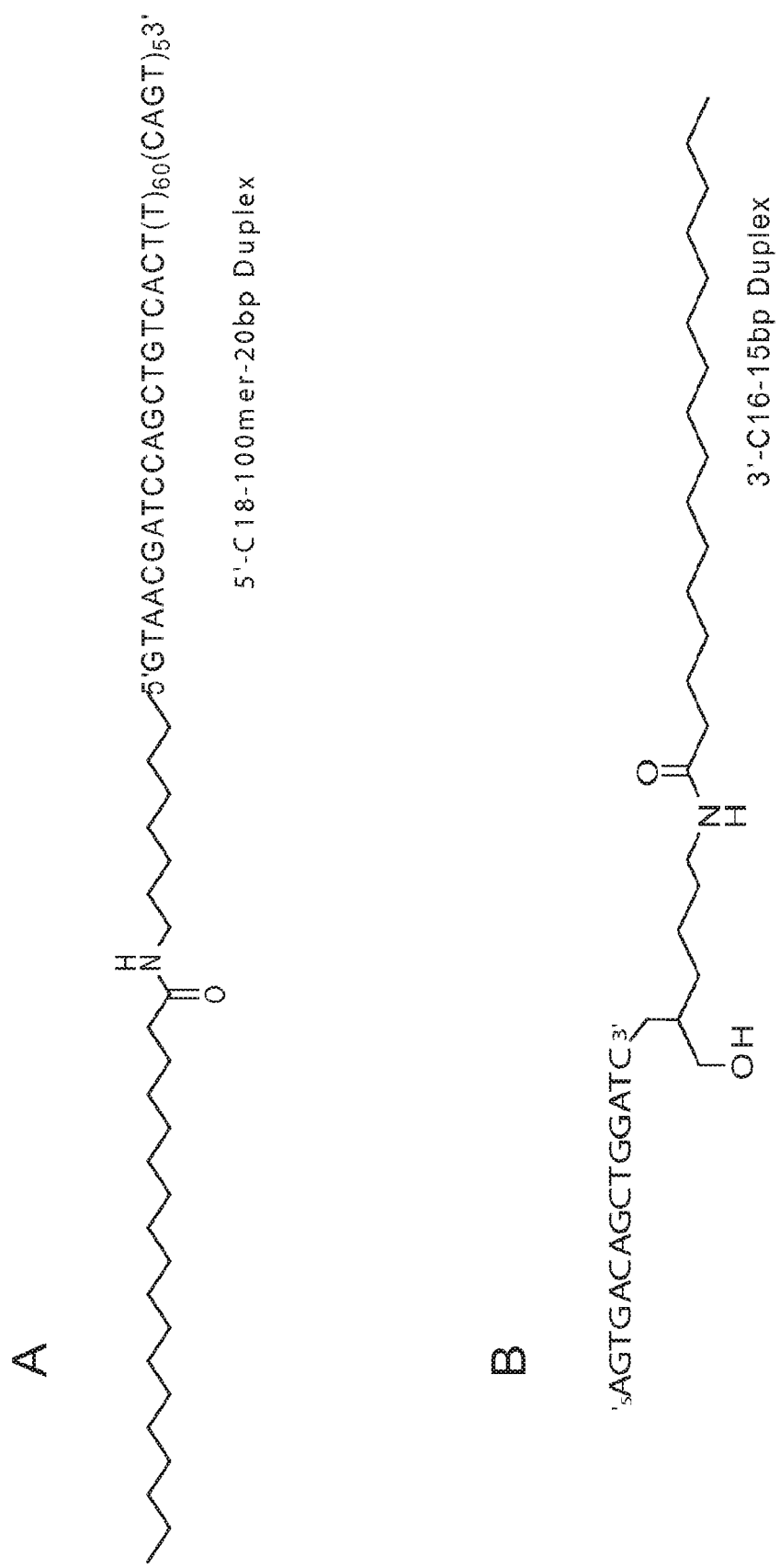
FIG. 13, Panels A-C depict membrane-anchored polynucleotides. Panel A shows a membrane-anchored polynucleotide having a sequence depicted in SEQ ID NO: 35-from position 1-80 and 101-120 of SEQ ID NO: 35. Panel B presents a membrane-anchored polynucleotide comprising a polynucleotide sequence (SEQ ID NO: 40) that can hybridize to a portion of the polynucleotide sequence of the compound presented in Panel A. Panel C depicts how the long (i.e. from FIG. 13, Panel A) and short (i.e. from FIG. 13, Panel B) membrane-anchored polynucleotides may interact with a membrane, individually and/or together.
Figure 13:
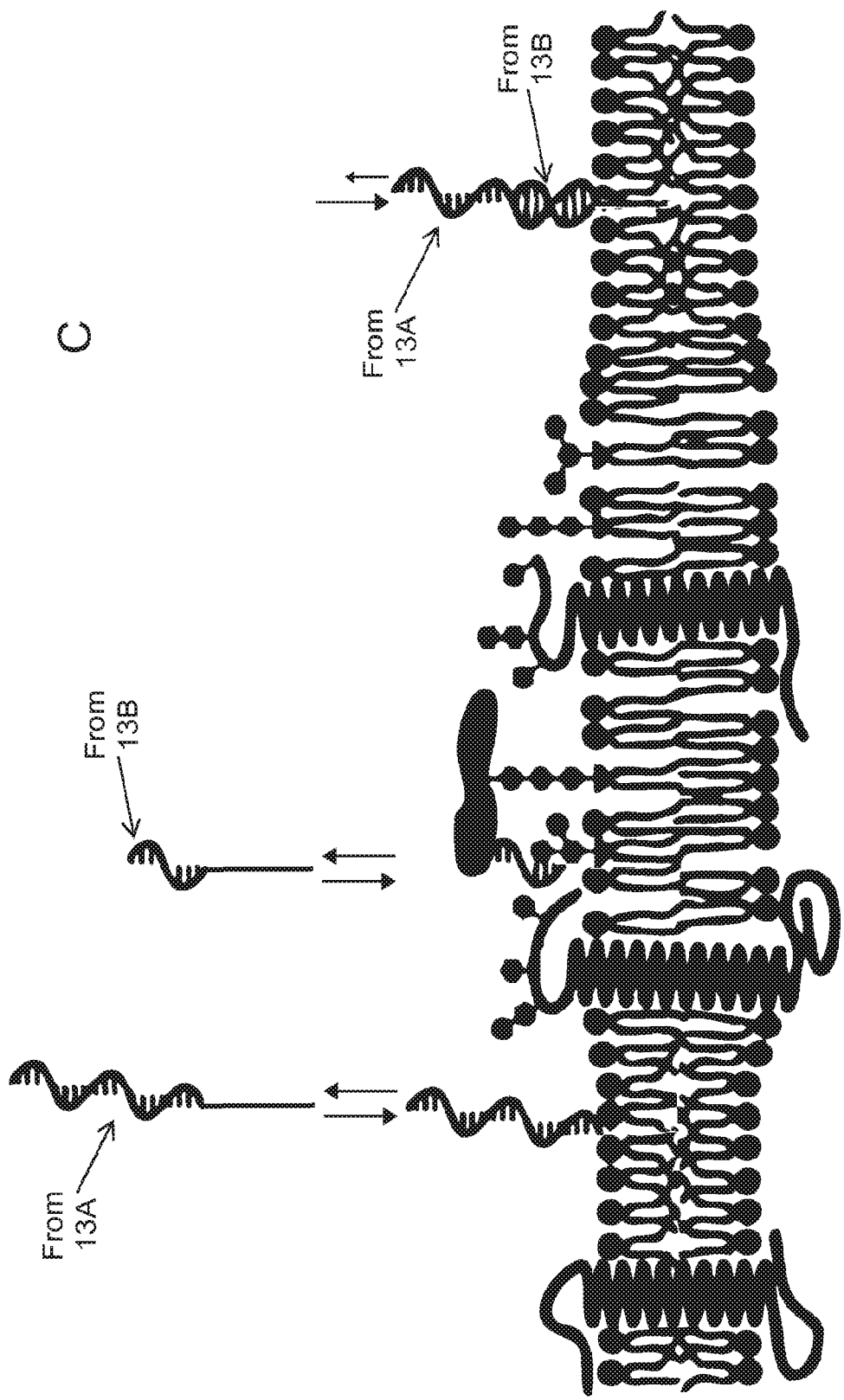
Figure 14:
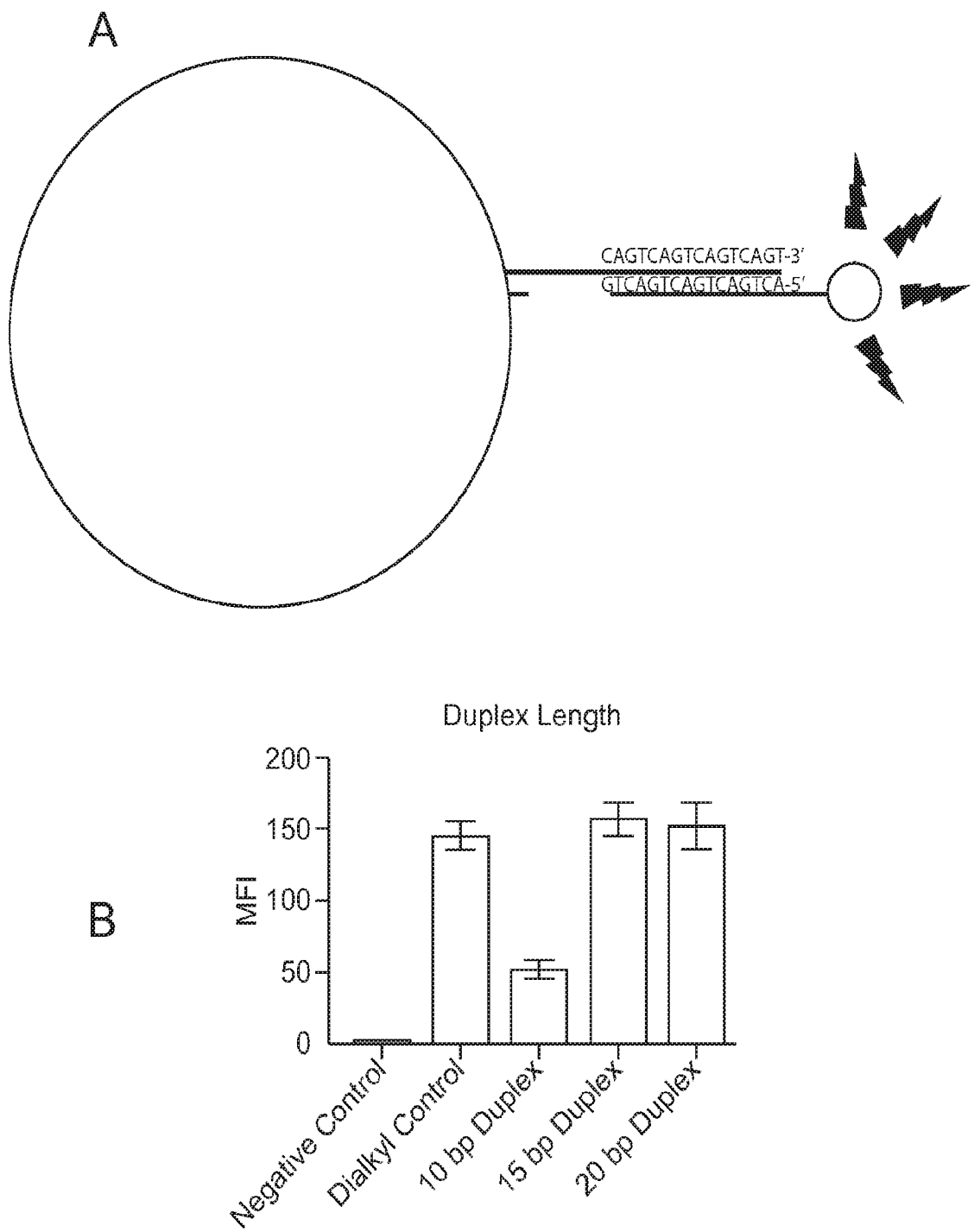
FIG. 14, Panels A-B depict a labeling scheme. Panel A shows a membrane modified with a polynucleotide, wherein the membrane-distal portion (having a sequence 5'-CAGTCAGTCAGTCAGT-3' (SEQ ID NO: 50)) of the polynucleotide hybridizes to a sequence: 5'-ACTGACTGACTGACTG-3' (SEQ ID NO: 51) of a polynucleotide strand that is attached to a fluorophore. Panel B depicts the Median Fold Fluorescence Increase (MFI) of Jurkat cells labeled with DNA polynucleotides as in Panel A, as a function of the number of base pairs that are complementary between the long and short DNA strands. The assay is performed by adding 1 uM of each long strand to a population of Jurkat cells; shaking for 5 min, repeat with short strand; washing; introducing complementary a complimentary Fluorescent Oligo (FITC), 40 min incubation at 4° C.; washing; staining with far-red Live/Dead stain for 15 min at 4° C.; and washing.
Figure 15:
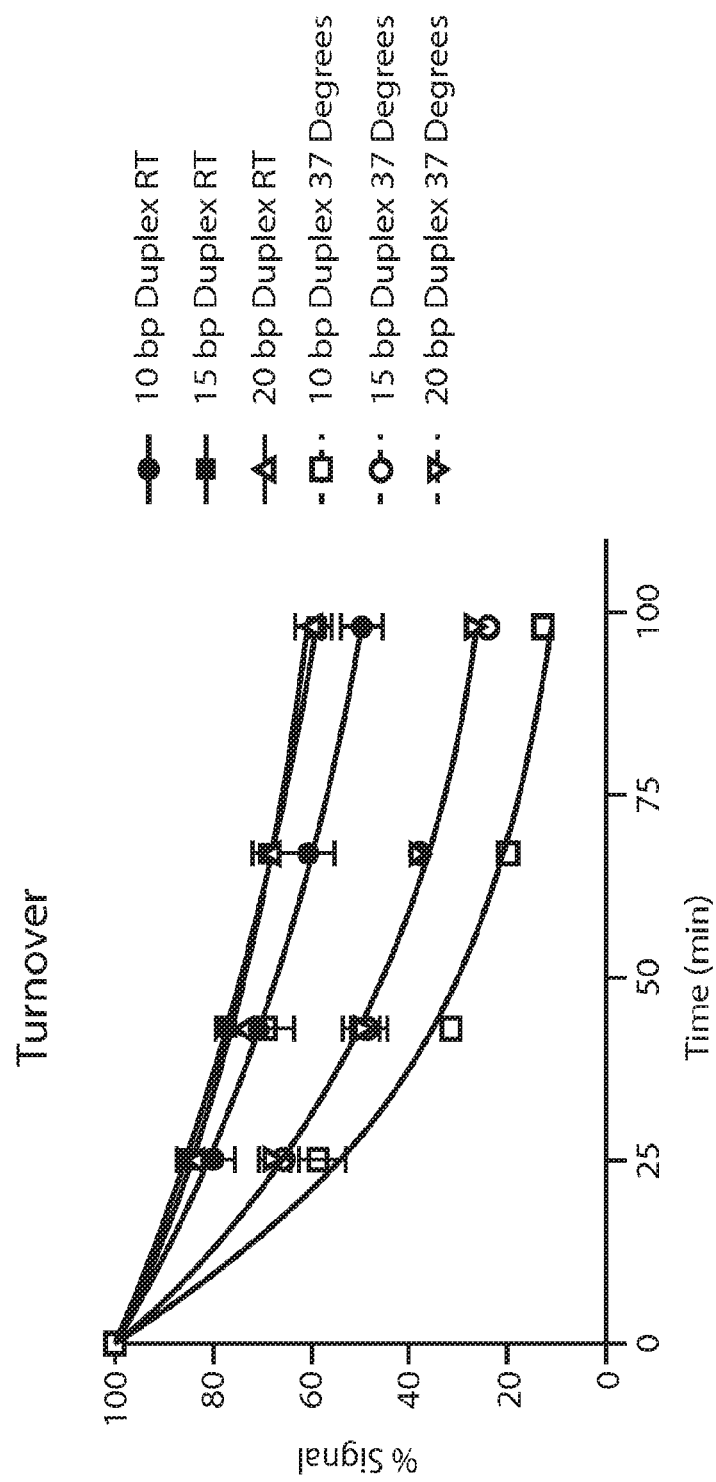
FIG. 15 depicts the turnover of a system of the general type presented in FIG. 14, Panels A-B, as a function of the temperature and the length of complementarity between the long- and short membrane-bound DNA polynucleotides.
Figure 16:
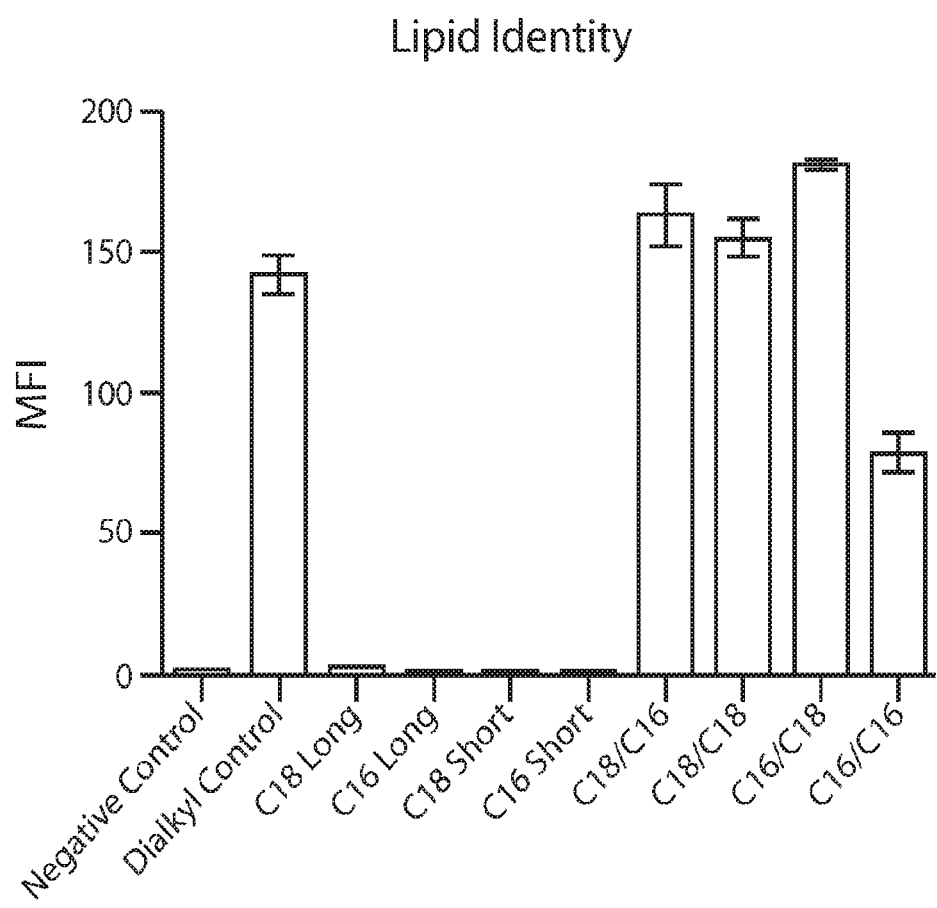
FIG. 16 depicts the effect of alkyl chain type on the system of FIG. 14, Panels A-B, and FIG. 15.
Figure 17:
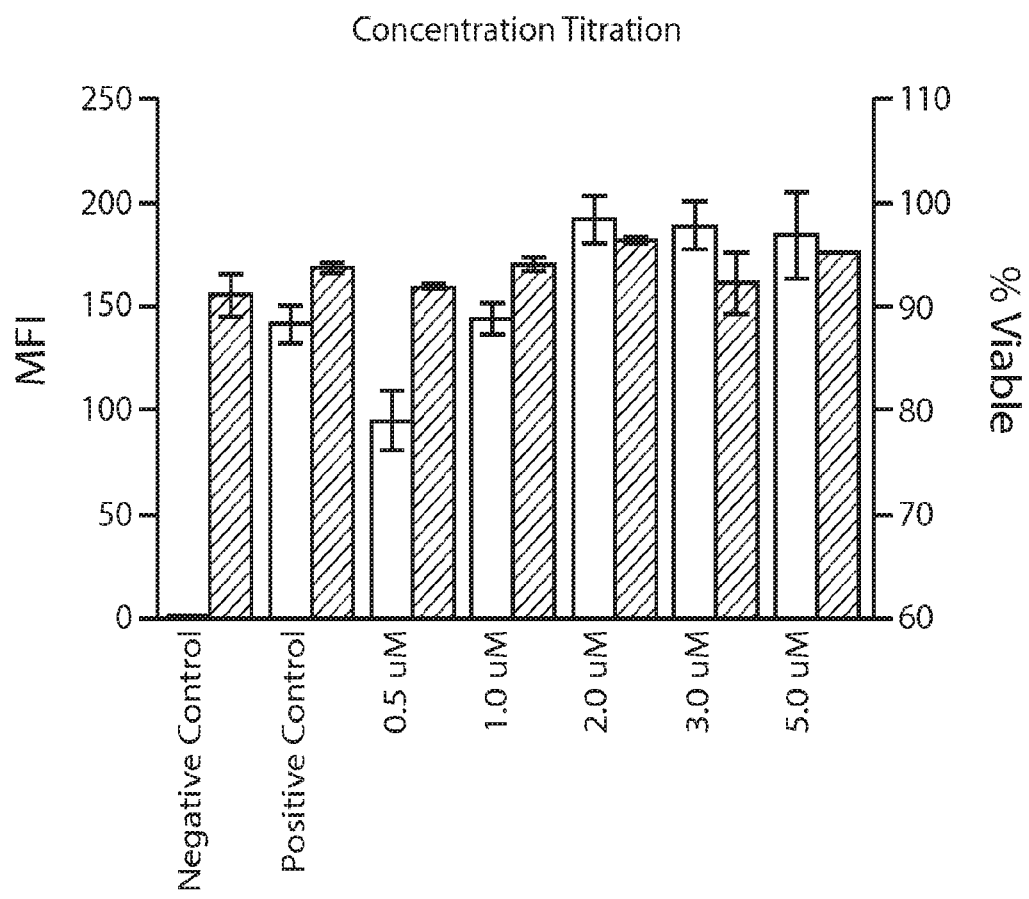
FIG. 17 depict the concentration titration of the MFI assay of FIG. 14, Panels A-B, and FIGS. 15-16, using a 20bp overlap region between the long and short-membrane-bound DNA polynucleotides, wherein either the short or long strand contained a monoalkyl chains comprising $C_{18}$, with the other strand containing a monoalkyl chain comprising $C_{16}$.
Figure 18:
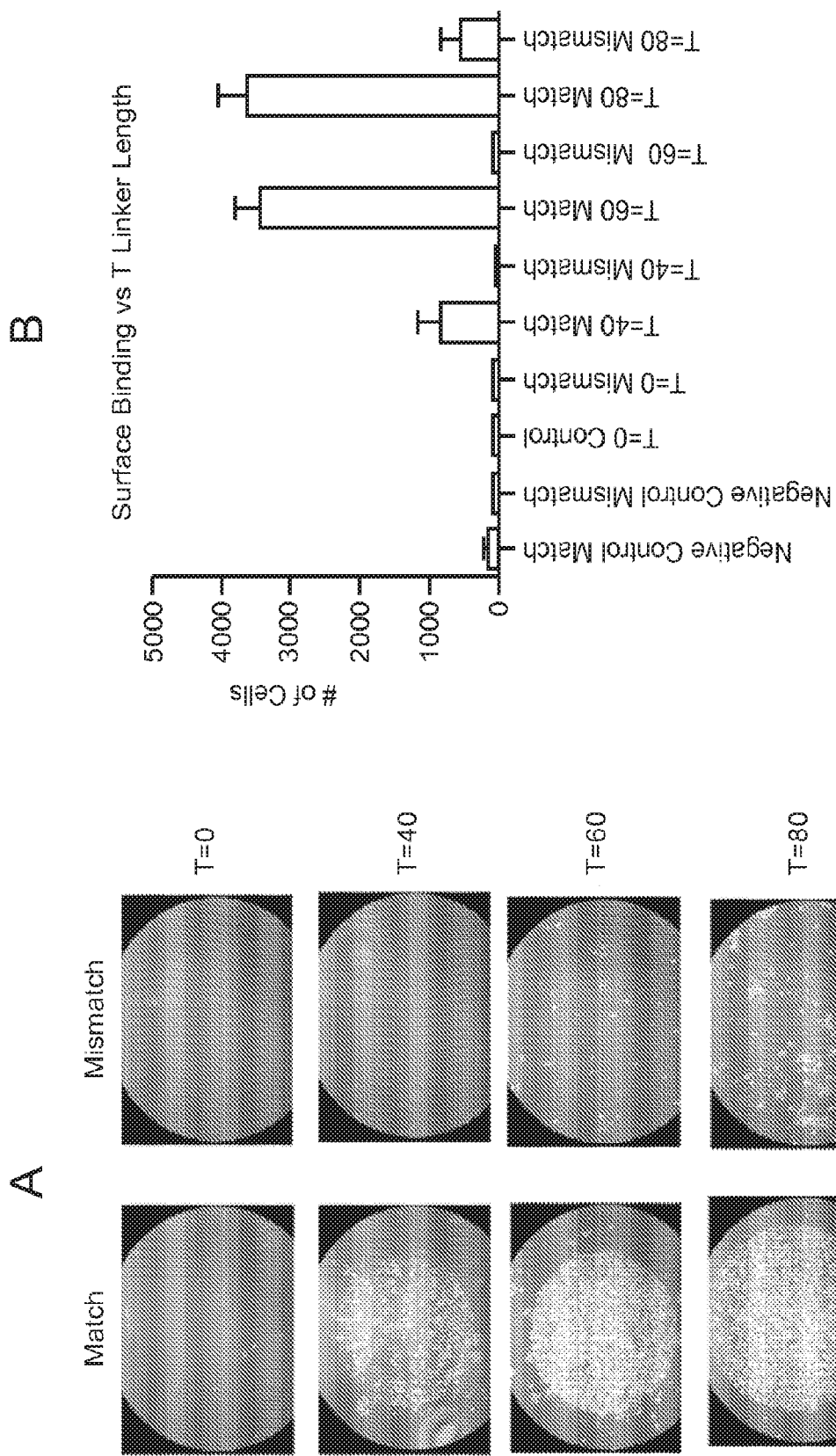
FIG. 18, Panels A-B depict the effect of adding a poly(dT) linker to the system of FIG. 16, as a function of linker length. Panel A shows poly(dT) linker lengths of T=0, 40, 60, or 80 base pairs within the polynucleotides. Panel B depicts the number of cells as a function of T linker length.
Figure 19:
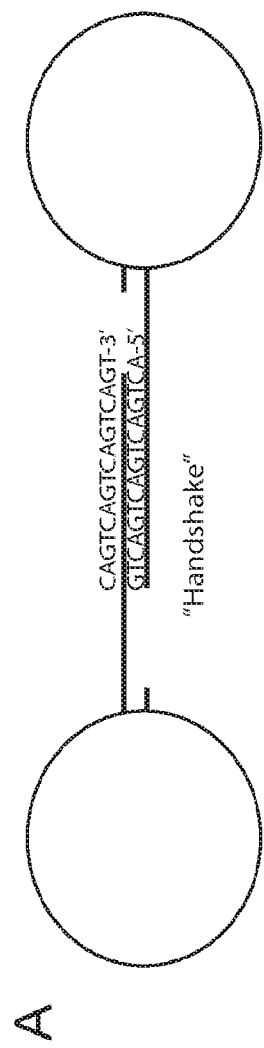
FIG. 19, Panels A-C depict cellular assembly using membrane anchored DNA according to aspects of the instant disclosure. Panel A depicts a schematic in which the membrane at left is modified by the addition of a long membrane-anchored polynucleotides and a short membrane-anchored polynucleotide strand that is complementary to the long strand at its membrane-proximal region. The membrane at right is labeled in a similar manner. The long membrane-anchored polynucleotide strand of the left membrane and the right membrane contain complementary sequences (SEQ ID NOs: 50 and 51, respectively) at their membrane distal ends. Panels B-C depict an example assembly.
Figure 19:
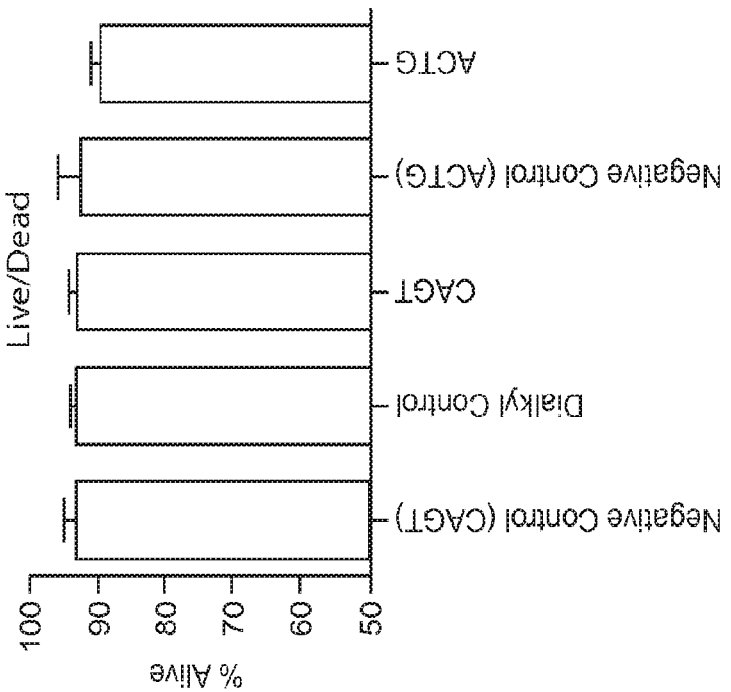
Figure 19:
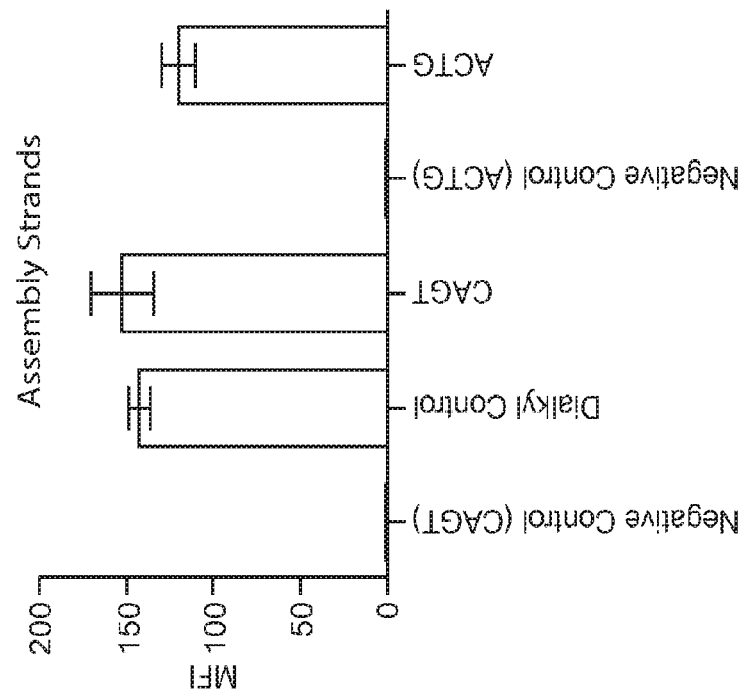

In certain embodiments, membrane anchored polynucleotide duplexes comprise a first membrane-anchored polynucleotide of the general structure shown in FIG. 13, Panel A. In other embodiments, the composition comprises a first membrane-anchored polynucleotide of the type that is produced by methods outlined in Example 2.

Membrane anchored polynucleotides that make up a membrane anchored polynucleotide duplex are often heterogeneous. In some embodiments, only one membrane anchored polynucleotide comprises a linker region, or a membrane distal adhesion region. In such embodiments, the membrane anchored polynucleotide lacking a linker and/or membrane distal adhesion region often comprises a shorter polynucleotide than the polynucleotide which is contained in the other membrane anchored polynucleotide of the duplex. Nomenclature that may be used to describe each membrane anchored polynucleotides reflects this fact: the 'long strand' or 'long membrane-bound DNA polynucleotide' may refer to a membrane anchored polynucleotide of the duplex that comprises a membrane distal adhesion region; while the 'short strand' or 'short membrane-bound DNA polynucleotide' may refer to a membrane anchored polynucleotide of the duplex that does not comprise a membrane distal adhesion region.

FIG. 13, Panels A-B present a non-limiting example of membrane anchored polynucleotide duplexes. Panel A presents a non-limiting example of a 'long strand,' while Panel B presents a non-limiting example of a 'short strand.' A general, non-limiting depiction of how a membrane anchored polynucleotide duplex may be formed is presented in Panel C. In this particular depiction, the short strand hybridizes to a portion of the long strand, where such hybridization occurs in each membrane anchored polynucleotide at the membrane proximal end.

In some embodiments, the short strand does not contain a linker region. In certain embodiments, the short strand does not contain a membrane distal adhesion region.

In some embodiments, the long- and short-strands of the membrane anchored polynucleotide duplex hybridize with one another over about 5 to 1000 nucleotides or more. In some embodiments, such hybridization occurs over about 5 to 10 nucleotides, about 10 to 20 nucleotides, about 20 to 40 nucleotides, about 40 to 60 nucleotides, about 60 to 80 nucleotides, about 80 to 100 nucleotides, about 100 to 120 nucleotides, about 120 to 140 nucleotides, about 140 to 160 nucleotides, about 160 to 180 nucleotides, about 180 to 200 nucleotides, about 200 to 225 nucleotides, about 225 to 250 nucleotides, about 250 to 275 nucleotides, about 275 to about 300 nucleotides, about 300 to 350 nucleotides, about 350 to 400 nucleotides, about 450 to 500 nucleotides, about 500 to 600 nucleotides, about 600 to 700 nucleotides, about 700 to 800 nucleotides, about 800 to 900 nucleotides, or about 900 to 1000 nucleotides or more.

In particular embodiments, such hybridization occurs in the long strand at the membrane proximal end of the polynucleotide. In other embodiments, it is separated from the membrane proximal end by 1 or more nucleotides. In certain embodiments, it is separated from the membrane proximal end by about 5 to about 1000 nucleotides. In particular embodiments, it is separated from the membrane proximal end by about 5 to 10 nucleotides, about 10 to 20 nucleotides, about 2.0 to 40 nucleotides, about 40 to 60 nucleotides, about 60 to 80 nucleotides, about 80 to 100 nucleotides, about 100 to 120 nucleotides, about 120 to 140 nucleotides, about 140 to 160 nucleotides, about 160 to 180 nucleotides, about 180 to 200 nucleotides, about 200 to 225 nucleotides, about 225 to 250 nucleotides, about 250 to 275 nucleotides, about 275 to about 300 nucleotides, about 300 to 350 nucleotides, about 350 to 400 nucleotides, about 450 to 500 nucleotides, about 500 to 600 nucleotides, about 600 to 700 nucleotides, about 700 to 800 nucleotides, about 800 to 900 nucleotides, about 900 to 1000 or more.

In particular embodiments, such hybridization occurs in the short strand at the membrane proximal end of the polynucleotide. In other embodiments, it is separated from the membrane proximal end by 1 or more nucleotides. In certain embodiments, it is separated from the membrane proximal end by about 5 to about 1000 nucleotides. In particular embodiments, it is separated from the membrane proximal end by about 5 to 10 nucleotides, about 10 to 20 nucleotides, about 20 to 40 nucleotides, about 40 to 60 nucleotides, about 60 to 80 nucleotides, about 80 to 100 nucleotides, about 100 to 120 nucleotides, about 120 to 140 nucleotides, about 140 to 160 nucleotides, about 160 to 180 nucleotides, about 180 to 200 nucleotides, about 200 to 225 nucleotides, about 225 to 250 nucleotides, about 250 to 275 nucleotides, about 275 to about 300 nucleotides, about 300 to 350 nucleotides, about 350 to 400 nucleotides, about 450 to 500 nucleotides, about 500 to 600 nucleotides, about 600 to 700 nucleotides, about 700 to 800 nucleotides, about 800 to 900 nucleotides, about 900 to 1000 nucleotides or more.

A membrane anchored polynucleotide duplex may be provided in compositions. In some embodiments, the composition may also comprise a second a compound comprising: a membrane anchoring region comprising a long alkyl chain of at least 12 carbon atoms; and a DNA polynucleotide having a membrane distal end and a membrane proximal end, wherein said DNA polynucleotide is at least about 10 nucleotides; wherein said DNA polynucleotide of said second compound comprises a contiguous stretch of at least about 10 nucleotides that hybridize to the DNA polynucleotide of said first compound.

A membrane anchored polynucleotide duplex may be provided in kits. In some embodiments, each membrane anchored polynucleotide that may make up a membrane anchored polynucleotide duplex is provided in a separate container of the kit.

Fluorophores and Pharmaceutical Compositions

In certain embodiments, the composition may comprise a fluorophore. The fluorophore may be conjugated to the membrane distal end of a polynucleotide contained in the composition. In other embodiments, the fluorophore may be attached to a different region of the first compound. In still other embodiments, the fluorophore may be attached to a polynucleotide sequence that hybridizes to a portion of the polynucleotide contained in a membrane-anchored polynucleotide of the composition.

In other embodiments, the composition may further comprise a pharmaceutical composition. The pharmaceutical composition may comprise a drug.

The term "drug" or "active agent" or any similar term is used broadly and generically herein to refer to any drug or any chemical or biological material or compound suitable or other beneficial agent which it is desired to deliver to an animal, and the present invention is not limited to any particular drugs. For illustrative purposes only, this includes but is not limited to anaesthetics, analgesics, cell transport/mobility impending agents such as colchicines, vincristine, cytochalasin B and related compounds; carbonic anhydrase inhibitors such as acetazolamide, methazolamide, dichlorphenamide, diamox and neuroprotectants such as nimodipine and related compounds; antibiotics such as tetracycline, chlortetracycline, bacitracin, neomycin, polymyxin, gramicidin, cephalexin, oxytetracycline, chloramphenicol, rifampicin, ciprofloxacin, aminosides, gentamycin, erythromycin and penicillin, quinolone, ceftazidime, vancomycin imipeneme; antifungals such as amphotericin B, fluconazole, ketoconazole and miconazole; antibacterials such as sulfonamides, sulfadiazine, sulfacetamide, sulfamethizole and sulfisoxazole, nitrofurazone and sodium propionate; antivirals, such as idoxuridine, trifluorothymidine, trifluorouridine, acyclovir, ganciclovir, cidofovir, interferon, DDI, AZT, foscamet, vidarabine, irbavirin, protease inhibitors and anti-cytomegalovirus agents; antiallergenics such as sodium cromoglycate, antazoline, methapyriline, chlorpheniramine, cetirizine, pyrilamine and prophenpyridamine; synthetic gluocorticoids and mineralocorticoids and more generally hormones forms derivating from the cholesterol metabolism (DHEA, progesterone, estrogens); non-steroidal antiinflammatories such as salicylate, indomethacin, ibuprofen, diclofenac, flurbiprofen, piroxicam and COX2 inhibitors; antineoplastics such as carmustine, cisplatin, fluorouracil, adriamycin, asparaginase, azacitidine, azathioprine, Neomycin, busulfan, carboplatin, carmustine, chlorambucil, cyclophosphamide, cyclosporine, cytarabine, dacarbazine, dactinomycin, daunorubicin, doxorubicin, estramustine, etoposide, etretinate, filgrastin, floxuridine, fludarabine, fluorouracil, florxymesterone, flutamide, goserelin, hydroxyurea, ifosfamide, leuprolide, levamisole, limustine, nitrogen mustard, melphalan, mercaptopurine, methotrexate, mitomycin, mitotane, pentostatin, pipobroman, plicamycin, procarbazine, sargramostin, streptozocin, tamoxifen, taxol, teniposide, thioguanine, uracil mustard, vinblasline, vincristine and vindesine; immunological drugs such as vaccines and immune stimulants; insulin, calcitonin, parathyroid hormone and peptide and vasopressin hypothalamus releasing factor; beta adrenergic blockers such as timolol, levobunolol and betaxolol; cytokines, interleukines and growth factors epidermal growth factor, fibroblast growth factor, platelet derived growth factor, transforming growth factor beta, ciliary neurotrophic growth factor, glial derived neurotrophic factor, NGF, EPO, PLGF, brain nerve growth factor (BNGF), vascular endothelial growth factor (VEGF) and monoclonal antibodies or fragments thereof directed against such growth factors; antiinflammatories such as hydrocortisone, dexamethasone, fluocinolone, prednisone, prednisolone, methylprednisolone, fluorometholone, betamethasone and triamcinolone; decongestants such as phenylephrine, naphazoline and tetrahydrazoline; miotics and anti-cholinesterases such as pilocarpine, carbachol, diisopropyl fluorophosphate, phospholine iodine and demecarium bromide; mydriatics such as atropine sulphate, cyclopentolate, homatropine, scopolamine, tropicamide, eucatropine; sympathomimetics such as epinephrine and vasoconstrictors and vasodilators, anticlotting agents such as heparin, antifibrinogen, fibrinolysin, anticlotting activase, antidiabetic agents include acetohexamide, chlorpropamide, glipizide, glyburide, tolazamide, tolbutamide, insulin and aldose reductase inhibitors, hormones, peptides, nucleic acids, saccharides, lipids, glycolipids, glycoproteins and other macromolecules include endocrine hormones such as pituitary, insulin, insulin-related growth factor, thyroid, growth hormones; heat shock proteins; immunological response modifiers such as muramyl dipeptide, cyclosporins, interferons (including alpha-, beta- and gamma-interferons), interleukin-2, cytokines, tumor necrosis factor, pentostatin, thymopentin, transforming factor beta2, erythropoetin; anti-angeogenesis proteins (e.g. anti VEGF, interferons), antibodies (monoclonal, polyclonal, humanized, etc.) or antibodies fragments, oligoaptamers, aptamers and gene fragments (oligonucleotides, plasmids, ribozymes, small interference RNA (siRNA), nucleic acid fragments, peptides), immunomodulators such as endoxan, thalidomide, tamoxifene; antithrombolytic and vasodilator agents such as rtPA, urokinase, plasmin; nitric oxide donors, nucleic acids, dexamethasone, cyclosporin A, azathioprine, brequinar, gusperimus, 6-mercaptopurine, mizoribine, folic acid analogs (e.g., denopterin, edatrexate, methotrexate, piritrexim, pteropterin, Tomudex(R), trimetrexate), purine analogs (e.g., cladribine, fludarabine, 6-mercaptopurine, thiamiprine, thiaguanine), pyrimidine analogs (e.g., ancitabine, azacitidine, 6-azauridine, carmofur, cytarabine, doxifluridine, emitefur, enocitabine, floxuridine, fluorouracil, gemcitabine, tegafur) fluocinolone, triaminolone, anecortave acetate, fluorometholone, medrysone, and prednislone; anti-infectives such as antibiotics and antiviral agents; analgesics and analgesic combinations; anorexics; antihelminthics; antiarthritics; antiasthmatic agents; anticonvulsants; antidepressants; antidiabetic agents; antidiarrheals; antihistamines; antiinflammatory agents; antimigraine preparations; antinauseants; antineoplastics; antiparkinsonisrn drugs; antipruritics; antipsychotics; antipyretics; antispasmodics; anticholinergics; sympathomimetics; xanthine derivatives; cardiovascular preparations including potassium and calcium channel blockers, beta-blockers, alpha-blockers, and antiarrhythmics; antihypertensives; diuretics and antidiuretics; vasodilators including general coronary, peripheral and cerebral; central nervous system stimulants; vasoconstrictors; cough and cold preparations, including decongestants; hormones such as estradiol and other steroids, including corticosteroids; hypnotics; immunosuppressives; muscle relaxants; parasympatholytics; psychostimulants; sedatives; tranquilizers; and nicotine and acid addition salts thereof.

Membranes

The present invention further provides membranes comprising a subject composition. In some embodiments, the membrane is a biological membrane (e.g., a lipid bilayer surrounding a biological compartment such as a cell, including artificial cells, or a membrane vesicle or sheet). In some embodiments, such cell is a Jurkat, MCF-10A, HeLa, or MEF cell. In some embodiments, the membrane is part of a living cell, as described above. In other embodiments, the membrane is an artificial (synthetic) membrane, e.g., a planar membrane, a liposome, etc. Membranes may be isolated membranes. In some embodiments, a membrane is affixed to a surface.

In some embodiments, the artificial membrane is a lipid bilayer. In other embodiments, the artificial membrane is a lipid monolayer. In some embodiments, the artificial membrane is part of a liposome. Liposomes include unilamellar vesicles composed of a single membrane or lipid bilayer, and multilamellar vesicles (MLVs) composed of many concentric membranes (or lipid bilayers).

Artificial membranes, and methods of making same, have been described in the art. See, e.g., U.S. Pat. No. 6,861,260; Kansy et al. (1998) *J. Med. Chem.* 41(7):1007-10; and Yang et al. (1996) *Advanced Drug Delivery Reviews* 23:229-256.

A subject artificial membrane will in some embodiments, include one or more phospholipids. In some embodiments, the artificial membrane comprises a mixture of phospholipids containing saturated or unsaturated mono or disubstituted fatty acids and a combination thereof. These phospholipids are in some embodiments selected from dioleoylphosphatidylcholine, dioleoylphosphatidylserine, dioleoylphosphatidylethanolamine, dioleoylphosphatidylglycerol, dioleoylphosphatidic acid, palmitoyloleoylphosphatidylcholine, palmitoyloleoylphosphandylserine, palmitoyloleoylphosphatidylethanolamine, palmitoyloleoylphophatidylglycerol, palmitoyloleoylphosphatidic acid, palmitelaidoyloleoylphosphatidylcholine, paimitelaidoyloleoylphosphatidylserine, palmitelaidoyloleoylphosphatidylethanolamine, pahnitelaidoyloleoylphosphatidylglycerol, palmitelaidoyloleoylphosphatidic acid, myristoleoyloleoylphosphatidylcholine, myristoleoyloleoylphosphatidylserine, myristoleoyloleoylphosphatidylethanoamine, myristoleoyloleoylphosphatidylglycerol, myristoleoyloleoylphosphatidic acid, dilinoleoylphosphatidylcholine, dilinoleoylphosphatidylserine, dilinoleoylphosphatidylethanolamine, dilinoleoylphosphatidyiglycerol, dilinoleoylphosphatidic acid, palmiticlinoleoylphosphatidylcholine, palmiticlinoleoylphosphatidylserine, palmiticlinoleoylphosphatidylethanolamine, palmiticlinoleoylphosphatidylglycerol, and palmiticlinoleoylphosphatidic acid. Suitable phospholipids also include the monoacylated derivatives of phosphatidylcholine (lysophophatidylidylcholine), phosphatidylserine (lysophosphatidylserine), phosphatidylethanolamine (lysophosphatidylethanolamine), phophatidylglycerol (lysophosphatidyiglycerol) and phosphatidic acid (lysophosphatidic acid), The monoacyl chain in such lysophosphatidyl derivatives will in some embodiments be palimtoyl, oleoyl, palmitoleoyl, linoleoyl myristoyl or myristoleoyl.

Kits and Systems

Kits and systems are provided which can facilitate the production and/or use of the compositions disclosed herein. Kits contemplated herein can include one or more of a membrane-anchored polynucleotide, compositions comprising membrane-anchored polynucleotides, an agent of interest for delivery, which may be provided in separate containers or, more usually, in a single composition in a sterile container.

In addition, the kit can contain instructions for using the components of the kit, particularly the compositions of the invention that are contained in the kit.

Utility

Membrane anchored polynucleotides, or compositions comprising membrane anchored polynucleotides, are useful in various research and therapeutic applications, including the study of cell-cell interactions, membrane mechanics, the bottom-up assembly of tissues, the quantitative imaging of non-adherent cells, or the study of biological processes occurring near a cell surface.

Methods of Use of Membrane Anchored Polynucleotides

Membrane anchored polynucleotide compounds and membrane anchored polynucleotide-containing compositions can be used in a variety of different pharmaceutical, cosmeceutical, diagnostic and biomedical applications. Non-limiting examples of such uses are described below and in the various Examples described herein.

For example, membrane anchored polynucleotide compounds and compositions comprising membrane anchored polynucleotide compounds find use in research and therapeutic applications, including the study of cell-cell interactions, membrane mechanics, the bottom-up assembly of tissues, the quantitative imaging of non-adherent cells, or the study of biological processes occurring near a cell surface.

In practicing such methods, a composition comprising a membrane anchored polynucleotide may first be contacted with a membrane under conditions allowing insertion of said composition into said membrane. In some embodiments, the method comprises contacting a membrane with a composition comprising a membrane anchored polynucleotide; and incubating said composition with said lipid membrane under conditions allowing insertion of said composition into said membrane. In certain embodiments, a method may comprise (1) contacting a membrane with a first composition comprising a membrane anchored polynucleotide; and incubating said composition with said lipid membrane under conditions allowing insertion of said composition into said membrane; (2) contacting the membrane with a second composition comprising a membrane anchored polynucleotide; and incubating said composition with said lipid membrane under conditions allowing insertion of said composition into said membrane; wherein the first and second compositions form a membrane anchored polynucleotide duplex.

Once associated with a membrane, the composition comprising a membrane anchored polynucleotide may be used to attach to a cargo or payload. Representative "cargo" or "payload" may include components that are encapsulated by a lipid vesicle or lipid particle (e.g., pharmaceutical agents, nutriceutical agents, cosmeceutical agents, imaging agents (e.g., gases, including air), radiopharmaceuticals, nuclear magnetic resonance contrast reagents, and the like). In certain embodiments, the encapsulated payload is typically in solution, as a crystal, as a powder, or a combination thereof. In some embodiments the payload may be a virus (e.g., an inactivated or attenuated virus) or bacteria (e.g., an inactivated or attenuated bacteria) or nucleic acid.

Attachment of a payload to a surface of a lipid particle can be accomplished by, for example, covalent attachment to the distal functional group of a sterol-modified amphiphilic lipid of the lipid particle. Various methods suitable for use or that can be adapted for use for attachment of a payload are described in, for example, *Liposomes: 2nd edition*, Oxford University Press, 2003, V. Torchilin and V. Weissig., Ed., The payload may thus be any of a variety of different agents, which may be adapted for a variety of different uses including, but not limited to pharmaceutical, nutriceutical, cosmeceutical, and diagnostic applications. Exemplary agent include, but are not limited to, bisphosphonates, carboplatin, cisplatin, oxaloplatin, carmustine, camptothecins, ciprofloxacin, chloromethane, cyclophosphamide, cyclopamine, cytosine arabinoside, dacarbazine, retinoic acid, doxifluridine, fluoroortic acid, geldanamycin, gemcitabine, gossypol, ifosfamide, hydroxytamoxifen, inrinotecan, phytic acid, protein kinase inhibitors, paclitaxel, resveratrol, taxanes, methylselano-cysteine, methotrexate, 6-thioguanine, tyrphostin, wogonin, etoposide, antisense oligonucleotides, siRNA, chemically modified RNA, citrate, 1, 2, 3, 4 butane tetracarboxylic acid, octasulfate sucrose, polyphosphates, ciprofloxicin, morphine, oxymorphone, buprenorphine and methadone. Such agents can be encapsulated alone or with another agent in the same liposome (e.g., one or more agents, two or more agents) to provide synergistic effects.

Payloads of particular interest include, but are not limited to, anti-cancer chemotherapeutics (e.g., doxorubicin, danorubicin, camptothecin, cisplatin, and the like), antibiotics (e.g., antibacterials, antifungals, antivirals, anti-parasitic agents, and the like), analgesics, anesthetics, anti-acne agents, biomolecules (e.g., nucleic acids (e.g., RNA, DNA, siRNA, and the like), polypeptides (e.g., peptides, including recombinant polypeptides and peptides, including naturally or chemically modified polypeptides and peptides (e.g., PEGylated polypeptides)), antibodies and the like), antigenic substances (e.g., which may be a component of a vaccine), anti-blood clogging agents, compounds to treat neurogenerative diseases, anesthetic agents such as; benzocaine, chloroprocaine, cocaine, procaine, tetracaine, bupivacaine, lidocaine, mepivacaine, fentanyl and trimecaine, analgesic agents such as diclofenac and molecules to enable ion-gradient loading into the liposome such as ammonium sulfate, triethylamine sulfate, the triethylamine salt of sucrose octasulfate, triethylamine polyphosphate, ammonium salt of phytic acid, the sodium, triethylamine or ammonium salt of acetic acid, the sodium, triethylamine or ammonium salt of oxalic acid, the sodium, triethylamine or ammonium salt of propanic acid, the sodium, triethylamine or ammonium salt of succinic acid, the sodium, triethylamine or ammonium salt of 1, 2, 3, 4 butane tetracarboxylic acid, the the sodium, triethylamine or ammonium salt of pyridine-2,3,5,6 tetracarboxylic acid, the sodium, triethylamine or ammonium salt of 1,2,4,5-benzenetetracarboxylic acid, the sodium, triethylamine or ammonium salt of 1,2,4,5-cyclohexanetetracarboxylic acid, the sodium, triethylamine or ammonium salt of 1,3,5-benzenetricarboxylic acid, the acetate salt of a polyamine such as spermine, spermidine, tris aminoethylamine and the like Nutriceutical agents (e.g., flavonoids, antioxidants such as gamma-linolenic acid, beta carotene, anthocyanins, beta-sitosterol) and dietary supplements (e.g., vitamins) can also be used as payloads in the lipid compositions of the present disclosure.

Exemplary cosmeceutical agents that can serve as payloads of the compositions of the present disclosure can include hydrating agents, proteins (e.g., collagen), vitamins, phytochemicals, enzymes, antioxidants, essential oils, UV protective agents (e.g., oxybenzone), cleansing agents, dyes, fragrances, and the like (e.g., such as may find use cosmetics, toiletries, fragrances, perfumes, skin care products and beauty aids).

Diagnostic agents include detectable labels, which can be radiolabels, fluorophores, luminophores, nuclear magnetic resonance contrast agents such as gadolinum, positron emission tomography labels and the like. In some embodiments, the liposome itself can serve as a diagnostic agent, e.g., as in use as micro-bubbles in ultrasound diagnosis.

In other methods, a first composition comprising a membrane anchored polynucleotide may first be contacted with a membrane under conditions allowing insertion of said composition into said membrane. A second a composition comprising a membrane anchored polynucleotide may be contacted with a membrane under conditions allowing insertion of said composition into said second membrane. The first and second membranes may be incubated under conditions in which the membrane distal adhesion region of the membrane anchored polynucleotides of the compositions hybridize. Such hybridization may permit the membranes to come in close association with one another. Such hybridization may permit the cells to adhere to one another. In still other embodiments, such hybridization may permit membrane fusion.

In other embodiments, a composition comprising a membrane anchored polynucleotide may be affixed to a surface. Surfaces may include beads, sheets, and the like. In some embodiments, the surface may be glass, and may be a passivated glass. In some embodiments, a membrane comprising a composition comprising a membrane anchored polynucleotide is contacted with such surface, under conditions allowing hybridization between a membrane anchored polynucleotide affixed to the surface, and a membrane anchored polynucleotide inserted to the membrane. The membrane may become reversibly affixed to said surface. In some embodiments, an agent, such as a drug, may be introduced to membranes so affixed to a surface. In other embodiments, a FITC labeled complementary polynucleotide is introduced, and optionally visualized.

In other embodiments, a membrane comprising a membrane anchored polynucleotide may be contacted with a surface comprising a polynucleotide that hybridizes to a portion of the membrane anchored polynucleotide. Such contacting may be under conditions allowing hybridization between the membrane anchored polynucleotide and the polynucleotide of the surface. In some embodiments, an agent, such as a drug, may be introduced. In other embodiments, a FITC labeled complementary polynucleotide is introduced, and optionally visualized.

Accordingly, methods comprising the use of membrane anchored polynucleotide compounds and compositions comprising membrane anchored polynucleotide compounds have research and therapeutic applications, including the study of cell-cell interactions, membrane mechanics, the bottom-up assembly of tissues, the quantitative imaging of non-adherent cells, or the study of biological processes occurring near a cell surface.

EXAMPLES

As can be appreciated from the disclosure provided above, the present disclosure has a wide variety of applications. Accordingly, the following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Those of skill in the art will readily recognize a variety of noncritical parameters that could be changed or modified to yield essentially similar results. Thus, the following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, dimensions, etc.) but some experimental errors and deviations should be accounted for.

Example 1: Synthesis of Membrane-Anchored DNA Polynucleotides

Materials and Methods 1,2-O-Dihexadecyl-sn-glycerol and 1,2-O-Dioctadecyl-sn-glycerol were obtained from Chem-Impex. N,N-Diisopropylethylamine (DIPEA), 2-Cyanoethyl N,N-diisopropylchlorophosphoramidite, octadecanoic acid, hexadecanoic acid, N-Methyl-2-pyrrolidone (NMP), 5-(Ethylthio)-1H-tetrazole (ETT), N,N'-Diisopropylcarbodiimide (DIPC), and succinimidyl-[N-maleimidopropionamido)-hexaethyleneglycol] ester [SM(PEG)$_6$] were obtained from Sigma-Aldrich. HPLC grade acetonitrile, triethylamine, acetic acid, and tris(2-carboxyethyl)phosphine (TCEP) were obtained from Fisher Scientific. Controlled pore glass (CPG) support, 1-O-Dimethoxytrityl-hexyl-disulfide,1'-[(2-cyanoethyl)-(N, N-diisopropyl)]-phosphoramidite (thiol phosphoramidite), and columns were obtained from Glen Research. 6-(4-Monomethoxytritylamino)hexyl-(2-cyanoethyl)-(N,N-diisopropyl)-phosphoramidite (amine phosphoramidite), standard phosphoramidites and DNA synthesis reagents were obtained from Azco Biotech. All materials were used as received.

Polynucleotide Synthesis

DNA polynucleotides were synthesized on an Applied Biosystems Expedite 8909 DNA synthesizer. Thiol and amine modified DNA were synthesized using thiol and amine phosphoramidites (100 mM), respectively, using a standard coupling protocol. Polynucleotides were purified by reversed-phase high-performance liquid chromatography (HPLC) using an Agilent 1200 Series HPLC System with a diode array detector (DAD) monitoring at 230 and 260 nm. Purifications used 100 mM triethylamine acetate (pH 7) H$_2$O/acetortitrile mobile phase on a C$_{18}$ (Agilent), C$_8$ (Agilent) or C$_4$ (Phenomenex) column for thiol-and amine-, monoalkylamide- and DIFO-, or dialkylphosphoglyceride-modified DNA, respectively, running a gradient between 8% and 95% acetonitrile. Matrix-assisted laser desorption ionization (MALDI) mass spectrometry was performed on a Voyager-DE Pro with a hydroxypicolinic acid/ammonium citrate matrix supplemented with acetone solubilized nitrocellulose. All nuclear magnetic resonance (NMR) were recorded on a Varian Innova 400.

Dialkylglycerol Phosphoramidite Synthesis

Dialkylglycerol phosphoramidites were synthesized as follows. A solution of 1,2-di-O-hexadecyl-glycerol (448 mg, 0.83 mmol) and N,N-diisopropylethylamine (320 µL, 1.8 mmol) in dichloromethane (10 mL) was cooled to 0° C. 2-Cyanoethyl N,N-diisopropylchlorophosphoramidite (300 µL, 1.3 mmol) was added dropwise over 1 min. The reaction was then stirred at 0° C. for 1 h then allowed to warm to RT over 3 h. The reaction mixture was washed with sat. NaHCO3 (3×20 mL) then dried over MgSO4 and concentrated in vacuo. Silica gel chromatography (90:9:1 hexanes: EtOAc:NEt3) yielded a waxy semisolid (419 mg, 68% yield estimated at >80% purity). Spectral data was found to agree with previous reports.

Figure 5:
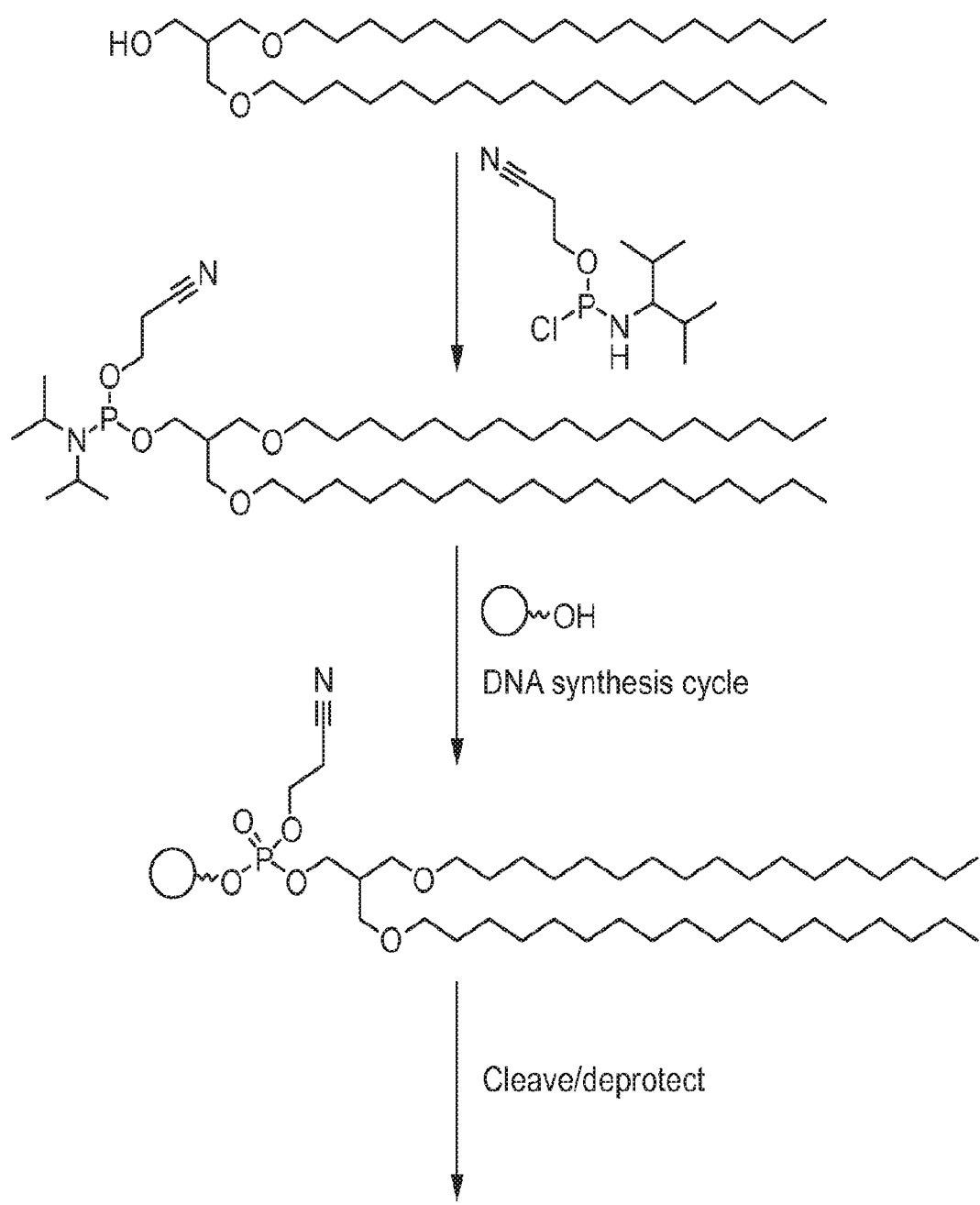
FIG. 5 depicts a synthesis scheme to produce dialkylphosphoglyceride-modified DNA polynucleotides.

Dialkylglycerol phosphoramidites were coupled to 5'-OH polynucleotides on controlled pore glass. Low support loading was important for efficient coupling. 500 µl of C$_{16}$ or C$_{18}$ dialkylglycerol phosphoramidite (200 mM) and 1 ml of ETT (300 mM) in dichloromethane were loaded into syringes and hand coupled to 200 nmol of polynucleotide on solid support. An overview of this process is presented in FIG. 5.

Fatty ACID Acylated DNA Synthesis

Fatty acid acylated DNA was synthesized by adding octadecanoic acid or hexadecanoic acid (200 mM), DIPC (200 mM), and DIPEA (400 mM) in NMP to 200 nmol of amine-modified polynucleotide on solid support shaking overnight at room temperature.

NHS-DNA was synthesized as follows. Thiol-modified DNA was resuspended in 10% distilled water, 40% 10 mM TCEP, and 50% 1×TE buffer (10 mM Tris with 1 mM EDTA, pH 7.5) to a final DNA concentration of 775 µM before being aliquoted and stored at −20° C. until use. Thiol-modified DNA (50 µl) was desalted using an aqueous equlibrated Centri-Spin 10 column (Princeton Separations) prior to adding 20 µl of SM(PEG)$_6$ (5mg/ml in DMSO) for 10 minutes at room temperature. The reaction was passed through a PBS equilibrated Centri-Spin 10 column prior to DNA concentration verification via UV-vis spectroscopy and application to cells.

DIFO-DNA Synthesis

DIFO-DNA was synthesized as described in Gartner, Z. J.; Bertozzi, C. R. *Proc Natl Acad Sci U S A* 2009, 106, 4606-10, the disclosure of which is fully incorporated herein by reference.

Polynucleotide Cleavage

All polynucleotides were cleaved from solid support with a 1:1 mixture of ammonium hydroxide/methylamine (AMA) for 15 minutes at 65° C. followed by evaporation of AMA with a speedvac system. Polynucleotides were filtered through 0.2-µm filters and purified by reversed-phase HPLC as described above. Membrane anchored polynucleotides were resuspended in distilled water and lyophilized repeatedly to remove residual buffer salts prior to use. The masses of representative samples were confirmed by MALDI-MS. Purified membrane anchored polynucleotides were resuspended in water and concentrations were determined by measuring their absorbance at 260 nm.

Synthesis Products

Using the protocols described above, the membrane-anchored polynucleotides were produced that included structures of the general formulae presented in FIG. 1, Panel A. Several products had the general structure shown in FIG. 1, Panel B. More specifically, specific membrane-anchored polynucleotides produced by the above methods included:

```
                                         (SEQ ID NO: 17)
Y-5'-T_x(CAGT)_5-3', where x = 0, 20, 40, 60, or 80,
Y = C_16 dialkylphosphoglyceride;

(SEQ ID NO: 18)
Y-5'-T_x(ACTG)_5-3', where x = 0, 20, 40, 60, or 80,
Y = C_16 dialkylphosphoglyceride;

(SEQ ID NO: 19)
Z-5'-(CAGT)_5-3', where Z = DIFO, NHS, C_18
dialkylphosphoglyceride, or C_16/_18 monoalkylamide;

(SEQ ID NO: 20)
Z-5'-(ACTG)_5-3', where Z = DIFO, NHS, C_18
dialkylphosphoglyceride, or C_16/_18 monoalkylamide;

(SEQ ID NO: 21)
FAM-5'-(CAGT)_5-3';

(SEQ ID NO: 22)
FAM-5'-(ACTG)_5-3';

(SEQ ID NO: 23)
Y-5'-T_80(CAGT)_5-3', where Y = C_16 dialkylphospho-
glyceride;

(SEQ ID NO: 241)
Y-5'-T_80(ACTG)_5-3', where Y = C_16 dialkylphospho-
glyceride;

(SEQ ID NO: 25)
Y-5'-T_80(GTA ACG ATC CAG CTG TCA CT)-3', where
Y = C_16 dialkylphosphoglyceride, (SEQ ID NO: 26)
Y-5'-T_80(AGT GAC AGC TGG ATC GTT AC)-3', where
Y = C_16 dialkylphosphoglyceride;

(SEQ ID NO: 27)
Y-5'-T_80(TCA TAC GAC TCA CTC TAG GG)-3', where
Y = C_16 dialkylphosphoglyceride;
```

-continued

Y-5'-T$_{80}$(CCC TAG AGT GAG TCG TAT GA)-3', where
Y = C$_{16}$ dialkylphosphoglyceride;
(SEQ ID NO: 28)

Y-5'-T$_{80}$(ACT GAC TGA CTG ACT GAC TG)-3', where
Y = C$_{16}$ dialkylphosphoglyceride;
(SEQ ID NO: 29)

Y-5'-T$_{80}$(CAG TCA GTC AGT CAG TCA GT)-3', where
Y = C$_{16}$ dialkylphosphoglyceride;
(SEQ ID NO: 30)

Y-5'-T$_{80}$(ACT GAT GGT AAT CTG CAC CT)-3', where
Y = C$_{16}$ dialkylphosphoglyceride;
(SEQ ID NO: 31)

Y-5'-T$_{80}$(AGG TGC AGA TTA CCA TCA GT)-3',
Y = C$_{16}$ dialkylphosphoglyceride;
(SEQ ID NO: 32)

Y-5'-T$_{39}$(CCC TCA TTC AAT ACC CTA TCG)T20(CAGT)5-3',
where Y = C$_{16}$ dialkylphosphoglyceride;
and
(SEQ ID NO: 33)

Y-5'-T$_{40}$(CCC TAG AGT GAG TCG TAT GA)T$_{20}$(CAGT)5-3',
where Y = C$_{16}$ dialylphosphoglyceride.
(SEQ ID NO: 34)

Example 2: Synthesis of Monoalkyl Membrane-Coupled Polynucleotides

Materials and Methods

N,N-Diisopropylethalamine (DIPEA), octadecanoic acid, hexadecanoic acid, N-Methyl-2-pyrrolidone (NMP), and N,N'-Diisopropylcarbodiimide (DIPC) were obtained from Sigma-Aldrich. HPLC grade acetonitrile, triethylamine, and acetic acid were obtained from Fisher Scientific. 6-(40Monomethoxytritylamine)hexyl-(2-cyanoethyl)-(N,N-diisopropyl)-phosphoramidite (5'-Amino-Modifier C6 phosphoramidite), controlled port glass (CPG) support and columns were obtained from Glen Research. Standard phosphoramidites and DNA synthesis reagents were obtained from Azco Biotech. All materials were used as received.

Polynucleotide Synthesis

Polynucleotides were synthesized on an Applied Biosystems Expedite 8909 DNA synthesizer. Amine modified DNA was synthesized using amine phosphoramidites (100 nM) using a standard coupling protocol. Polynucleotides were purified by reversed-phase high-performance liquid chromatography (HPLC) using an Agilent 1200 Series HPLC System with a diode array detector (DAD) monitoring at 230 and 260 nm. Purifications used 100 mM triethylamine acetate (pH 7) H20/acetonitrile mobile phase on a CS (Agilent) column for monoalkylamide-modified DNA, running a gradient between 8% and 95% acetonitrile. Matrix-assisted laser desorption ionization (MALDI) mass spectrometry was performed on a Voyager-DE Pro with hydroxypicolinic acid/ammonium citrate matrix supplemented with acetone solubilized nitrocellulose.

FMOC protecting group was removed by standard methods, CPG resin was suspended in 20% pyridine in DMF for 30 minutes. The resin was subsequently washed with DMF 3 times at room temperature. Carboxylic acid acylated DNA was synthesized by adding octadecanoic acid or hexadecanoic acid (200 mM), DIPC (200 mM) and DIPEA (400 mM) in NMP to 200 nmol of amine-modified polynucleotide on solid support, shaking overnight at room temperature.

Polynucleotides were cleaved from solid support with a 1:1 mixture of ammonium hydroxide/methylamine (AMA) for 15 minutes at 65° C. followed by evaporation of AMA with a SpeedVac system. Polynucleotides were filtered through 0.2 µm filters and purified by reversed-phase HPLC as described above. Lipid-modified polynucleotides were resuspended in distilled water and lyophilized three times to remove residual HPLC buffer salts prior to use. The concentrations of purified polynucleotide-lipids were quantified by measuring their absorbance at 260 nm.

Synthesis Products

Using the protocols described above, the membrane-anchored polynucleotides produced included those shown in FIG. 13, Panels A-C, and the following:

Y-5'-GTAACGATCCAGCTGTCACT-T$_x$(CAGT)$_5$-3', where X = 0, 40, 60, 80, Y = C$_{16}$/C$_{18}$ monoalkylamide;
(SEQ ID NO: 35)

Y-5'-GATCCAGCTCTCACT-T$_x$(CAGT)$_5$-3', where X = 60, Y = C$_{18}$ monoalkylamide;
(SEQ ID NO: 36)

Y-5'-AGCTGTCACT-T$_x$(CAGT)$_5$-3', where X = 60, Y = C$_{18}$ monoalkylamide;
(SEQ ID NO: 37)

C$_{18}$-5'-T$_{60}$(ACTG)$_5$-3';
(SEQ ID NO: 38)

5'-AGTGACAGCTGGATCGTTAC-3'Z, where Z = C$_{16}$ monoalkylamide;
(SEQ ID NO: 39)

5'-ACTGACACTCTGGATC-3'Z, where Z = C$_{16}$ monoalkylamide;
(SEQ ID NO: 40)

5'-ACTGACAGCT-3'-Z, where Z = C$_{16}$ monoalkylamide;
(SEQ ID NO: 41)

FAM-5'-(CAGT)$_5$-3';
(SEQ ID NO: 42)

FAM-5'-(ACTG)$_5$-3';
(SEQ ID NO: 43)

Example 3: DNA Polynucleotide Labeling of Cells and Quantification of Cell Surface Polynucleotides Membrane-anchored DNA Polynucleotide Molecules: adherent cells were lifted by incubating with 0.25% trypsin at 37° C. for 5 minutes followed quenching with 10% FBS containing media. In order to maintain intact proteins on the cell surface, cells labeled with NHS-DNA and DIFO-DNA were lifted by incubating at 37° C. in 0.04% EDTA in PBS for 20-30 minutes followed by a 30 second 0.05% trypsin pulse. Trypsin was quenched by addition of soybean trypsin inhibitor (1 mg/ml) and 10% FBS containing media. Lifted cells were washed with calcium and magnesium free PBS three times, and (10$^6$) cells were resuspended in 49 µl of PBS and labeled by addition of 1 µl of 250 µM lipid-DNA in water making a final DNA concentration of 5 µM. Cells were gently agitated by slow vortexing for 5 minutes at room temperature.

NHS-DNA and DIFO-DNA: was prepared as described and added to cells (1×10$^6$) in 50 µl of 175 µM NHS-DNA or DIFO-DNA and mixed for 30 minutes at room temperature or 37° C., respectively. All cells were washed in ice-cold PBS three times to remove residual, unreacted DNA before incubating in 50 µl of 20mer complementary 6-FAM modified polynucleotide (1 g/ml, Operon) for 30 minutes at 4° C. protected from light. Cells were washed one time before resuspending in LIVE/DEAD® Fixable Dead Cell Stain (Invitrogen) for 15 minutes at 4° C. protected from light. Cells were washed one last time before flow cytometry analysis. For kinetic stability time course experiments, cells were incubated at 37° C. for designated amount of time before probing with fluorescent, complementary polynucleotide. All reported values are the average of 3 independent measurements. Median fluorescence increase (MFI) was calculated as the fold increase of fluorescence levels over unmodified cells.

Figure 2:
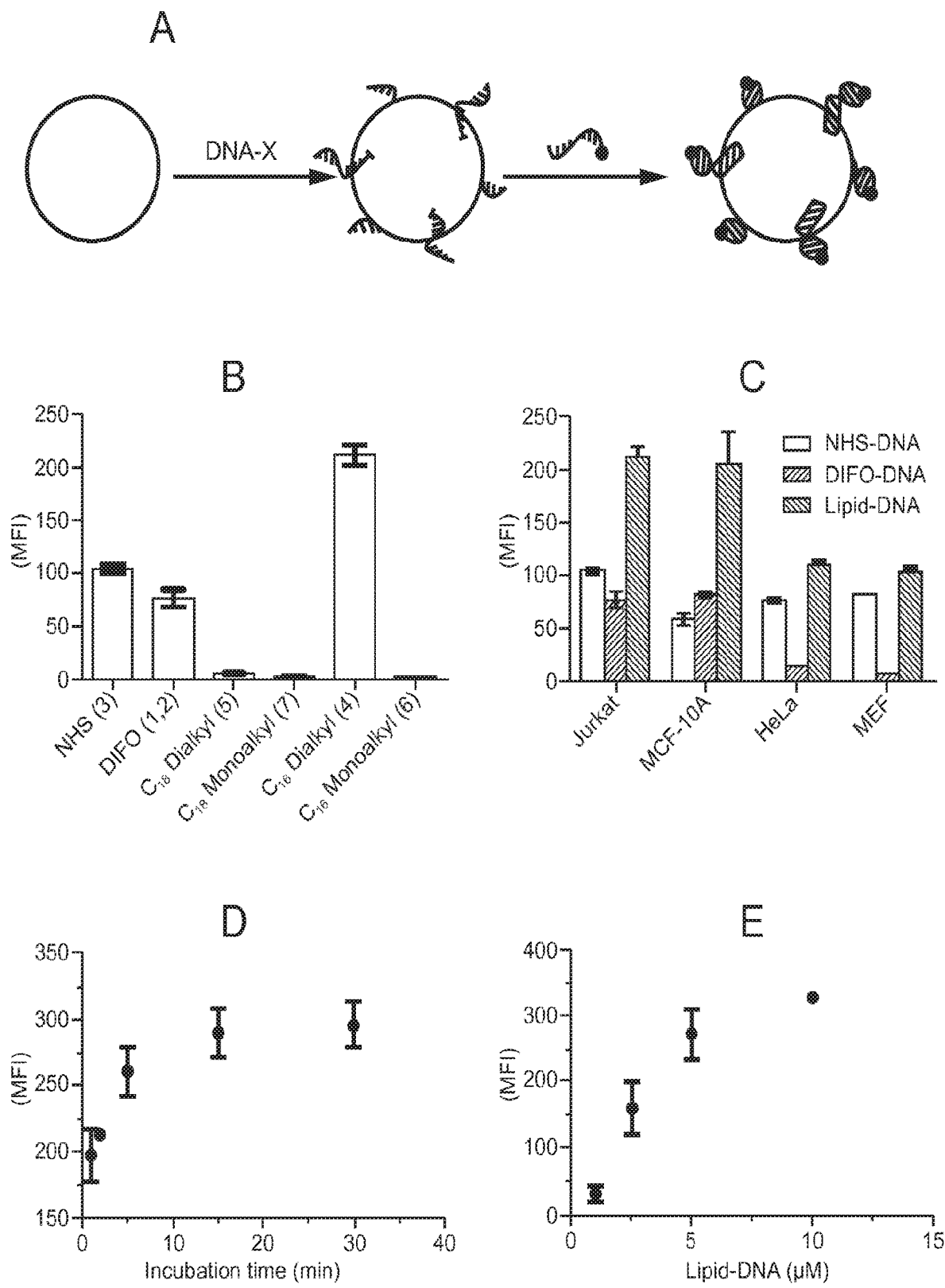
FIG. 2, Panels A-E depict the incorporation of polynucleotides to cell surfaces. Panel A: Scheme for labeling and selectively quantifying cell surface polynucleotides by flow cytometry. Panel B: Median Fold Fluorescence Increase (MFI) of Jurkat cells labeled with modified DNA polynucleotides. Panel. C: Extent of cell surface modification by NHS-DNA, DIFO-DNA, and $C_{16}$ dialkylphosphoglyceride-modified DNA polynucleotides (lipid-DNA) across four different cell types. Panel D: Time course for cell surface modification with $C_{16}$ dialkylphosphoglyceride-modified DNA polynucleotides (lipid-DNA). Panel E: Concentration dependence of cell surface labeling by $C_{16}$ dialkylphosphoglyceride-modified DNA (lipid-DNA). Nomenclature of the molecules used to modify the cell surfaces consistent with FIG. 1, Panels A-B; "lipid-DNA" denotes dialkylphosphoglyceride-modified DNA polynucleotides.

Results $C_{18}$ dialkylphosphoglyceride-modified DNA polynucleotides were prepared and assayed for their ability to partition into Jurkat T-lymphocyte cell membranes using flow cytometry (FIG. 2, Panel A). Although some polynucleotides incorporated into cell surfaces, their absolute numbers were insufficient to mediate cell-cell or cell surface adhesion (FIG. 2, Panel B). Neither increasing the concentration of modified DNA polynucleotides, the temperature, nor duration of incubation resulted in substantial increases in membrane incorporation (FIG. 6).

Figure 6:
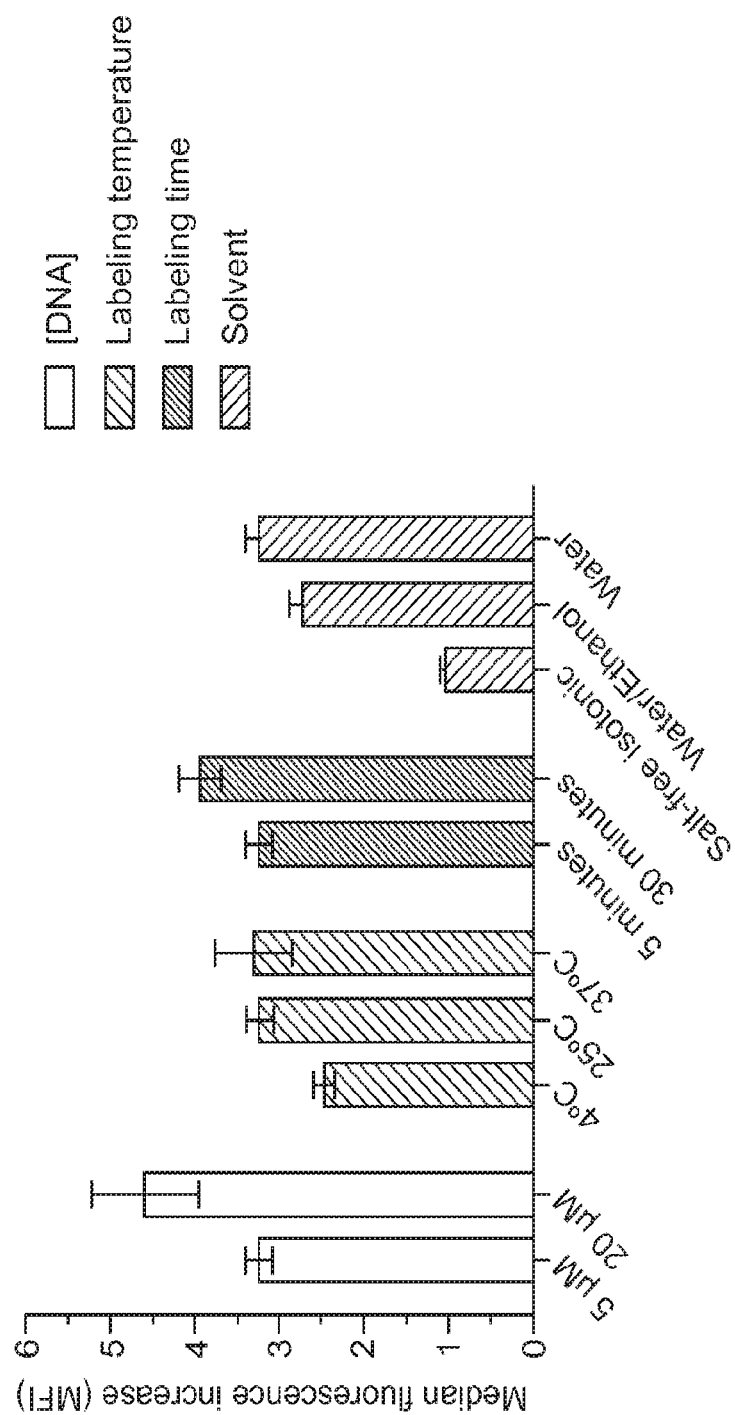
FIG. 6 depicts the effect of concentration, temperature, reaction time, and cosolvent on membrane insertion of 5' $C_{18}$ phosphoglyceride-labeled polynucleotides.

Attempting to destabilize aggregates by adding lipid-DNA from solutions containing 50% ethanol or under isotonic salt-free conditions did not lead to increased labeling (FIG. 6).

Single acyl chain bearing polynucleotides appeared to be unstable in the cell surface, as it was not possible to detect the DNA conjugates on the cell membrane under tissue culture conditions (FIG. 2, Panel B).

Figure 7:
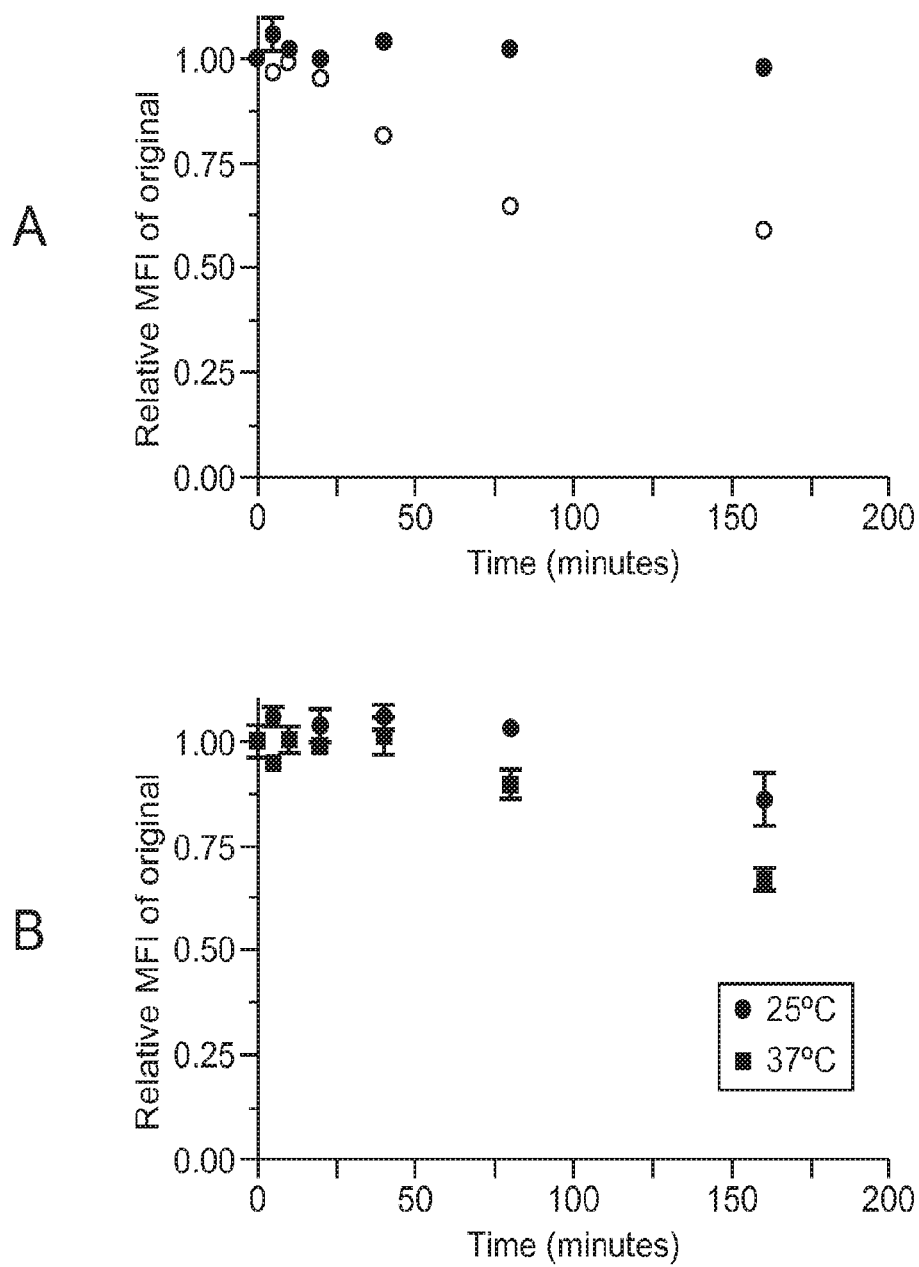
FIG. 7, Panels A-C depict the cell surface stability of polynucleotides introduced by NHS-ester modified DNA (Panel A) and dialkylphosphoglyceride-modified polynucleotides (Panel B). Panel C presents tabulated data from Panels A-B.

$C_{16}$ dialkylphosphoglyceride-modified polynucleotides were prepared and assayed as described. Surprisingly, the $C_{16}$ dialkylphosphoglyceride-rnodified polynucleotides rapidly incorporated into Jurkat cell membranes. Even after repeated washing with PBS containing 1% serum, only minor reductions in cell-surface $C_{16}$ dialkylphosphoglyceride-modified polynucleotides were observed (FIG. 2, Panel B). All tested cell-types were modified independent of trypsin treatment (FIG. 2, Panel C). Labeling was rapid (FIG. 2, Panel D) and dose dependent (FIG. 2, Panel E). Finally, the lifetime of cell surface DNA by flow cytometry was assayed and found that on Jurkat cell surfaces, $C_{16}$ dialkylphosphoglyceride-modified DNA polynucleotides decayed to 86% of its initial concentration by 160 minutes at 25° C. and to 67% of its initial intensity over the same time period at 37° C. These values were similar but not identical to those measured for protein or glycan-modified cell surfaces (FIG. 7, Panels A-C).

Example 4: Programmed Cell Assembly

Materials and Methods

CellTracker Green CMFDA and CellTrace Far Red DDAO-SE (Invitrogen) stocks were prepared at a concentration of 10 mM in anhydrous DMSO. Cells were resuspended in 10 μM stain in serum-free media for 15 minutes at 37° C. before going through labeling manipulations described above in other Examples herein. After washing away unreacted DNA, cells were resuspended at $1 \times 10^6$ cells/ml. Cell type of interest that had been labeled green was mixed with far red Jurkats at a ratio of 1:100 in 200 μl and mixed at 150 rpm for 10 minutes in an Ultra-Low Attachment 24-well plate (Corning) before analyzing via flow cytometry and visualizing on a Zeiss Axiovert at 40×magnification.

Results

Figure 3:
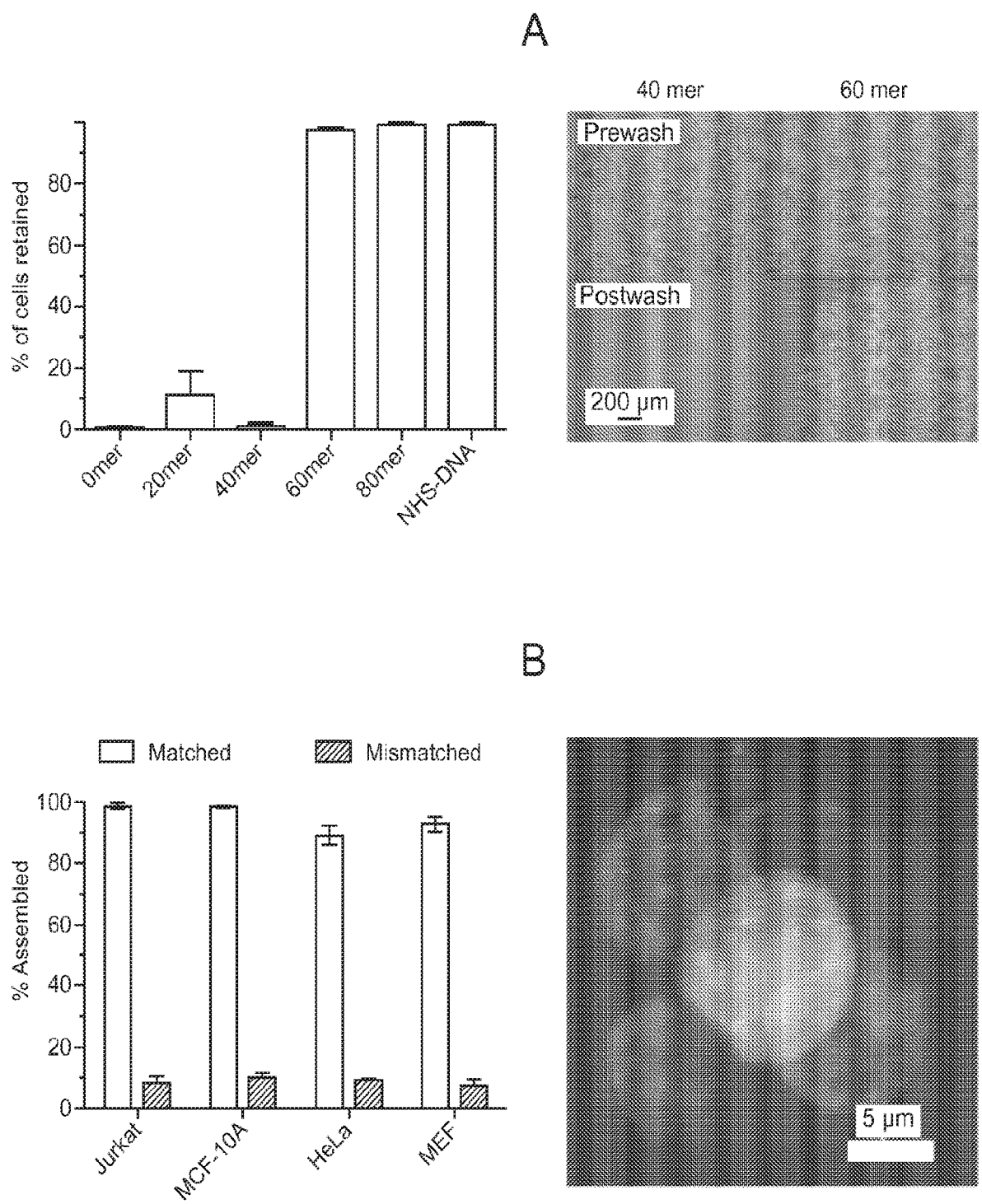
FIG. 3, Panels A-B depict chemical control of cellular adhesion by dialkylphosphoglyceride-modified DNA polynucleotides. Panel A: Jurkat cells bearing a 60- or 80mer poly(dT) linker within the DNA polynucleotides had considerably more cell-surface adhesion than cells with shorter linkers within the DNA polynucleotide. Panel B: The indicated cell type bearing $C_{16}$ dialkylphosphoglyceride-modified DNA polynucleotides incorporating 80mer poly(dT) linkers was assembled with a 100×excess of a complementary-labeled population of Jurkat cells and then analyzed by flow cytometry. Assembly efficiency is reported as the fraction of minority cells associated with at least one majority cell. A FACS purified cell cluster imaged by confocal fluorescence microscopy is shown to the right.

Protein lysine side chains conjugated to NHS-ester modified polynucleotides (3) react with functionality present throughout the cell surface. Without being bound by theory, $C_{16}$ dialkylphosphoglyceride-modified polynucleotides only localize proximal to the cell membrane, where steric hindrance from the glycocalyx may limit accessibility to complementary labeled surfaces. The ability of NHS-ester modified polynucleotides and $C_{16}$ dialkylphosphoglyceride-modified polynucleotides at modified cell surfaces to adhere to complementary labeled surfaces was compared. DNA-modified glass surfaces were prepared by reacting 5'-amino-terminated polynucleotides with aldehyde-coated glass surfaces by reductive amination. Subsequent reduction of unreacted aldehyde with $NaBH_4$ and passivation with Sigmacote then Plutonic F108 provided a non-adhesive surface. Populations of Jurkat cells were prepared that were labeled with a complementary 20mer strand anchored proteins through NHS-ester modified polynucleotides or to the cell membrane through and $C_{16}$ dialkylphosphoglyceride-modified polynucleotides. Finally, the ability of NHS-ester modified polynucleotide- and $C_{16}$ dialkylphosphoglyceride-modified polynucleotide-labeled cells to adhere to the DNA-labeled surface was tested. Cells labeled with the $C_{16}$ dialkylphosphoglyceride-conjugated 20mer strand did not significantly adhere to the glass surface whereas NHS-ester modified polynucleotide-labeled cells showed significant adhesion despite similar absolute numbers of polynucleotides at the cell surface (FIG. 3, Panel A).

A surprising and unexpected discovery was that the addition of poly(dT) linkers between the 20mer sequence and the membrane anchor region increased the adhesive capacity of labeled cells. A series of polynucleotides were synthesized that incorporated 20, 40, 60, or 80 thymine nucleotides between the 20mer sequences and the membrane anchor region and tested for their ability to direct adhesive interactions between labeled cells and complementary labeled surfaces. A sharp transition in adhesive capacity was observed between the polynucleotides incorporating 40 and 60 thymine nucleotides (FIG. 3, Panel A).

Utilizing the 80mer poly(dT) linker, the degree to which $C_{16}$ dialkylphosphoglyceride-modified polynucleotides could program the self-assembly of complementary labeled populations of Jurkat cells was tested. Near quantitative formation of chemically programmed cell-cell adhesions were observed after 10 minutes of mixing (FIG. 3, Panel B). Similar results were obtained with adherent MCF-10A, MEF, and HeLa cells.

Example 5: Assay for Cell Attachment and Dynamic Membrane Observations

Preparation of DNA Arrays:

5'-amino-modified DNA was prepared in a buffer of 450 mM NaCl, 50 mM dibasic sodium citrate, 50 mM dibasic sodium phosphate, 5% trehalose, and 1% fresh $NaCNBH_3$. DNA was patterned onto aldehyde-silanized glass (Schott) using either a micropipette for large-scale patterns or a BioForce Nano eNabler for small-scale patterns and incubated 12 hours in a humidified chamber. Slides were reduced with $NaBH_4$ and passivated with both SigmaCote (Sigma) and Pluronic F108 before use.

Cells incorporating lipid-DNA were allowed to settle onto patterned glass within a PDMS-based flow cell for 30 minutes. Only cells hybridized to the surface via DNA were retained when the surface was washed with PBS. Patterned cells were imaged at 37° C. on a Zeiss Axiovert 200M at 200× or 400×magnification using phase contrast settings.

Cells were incubated with 1 uM latrunculin A either 10 (after nocodazole treatment) or 40 minutes prior to timelapse imaging. Cells were incubated with 10 ng/mL phorbol 12-myristate 13-acetate (PMA) and 1.3 uM ionornycin 4 hours prior to lipid incorporation. Cells were incubated with 100 uM nocodazole, with or without addition of latruneulin, 10 minutes prior to imaging.

Image Analysis

Using ImageJ, cells were picked automatically from 20×fields of view and subsequently binarized. For each time point, scanning down the y-axis, the horizontal slice with the greatest width was identified. For each cell, the coefficient of variation was calculated for this set of widths, and this statistic was used to characterize each cell's membrane motility for binning. Error bars signify standard error.

Results

To image the membrane dynamics of non-adherent cells, $C_{16}$ dialkylphosphoglyceride-modified polynucleotide-modified cells were chemically immobilized on passivated glass surfaces by grids of 5 μm spots bearing complementary DNA sequences. It was hypothesized that chemical immobilization through small DNA patches would be minimally perturbing but still facilitate imaging and allow for the addition and removal of small molecule drugs.

Figure 4:
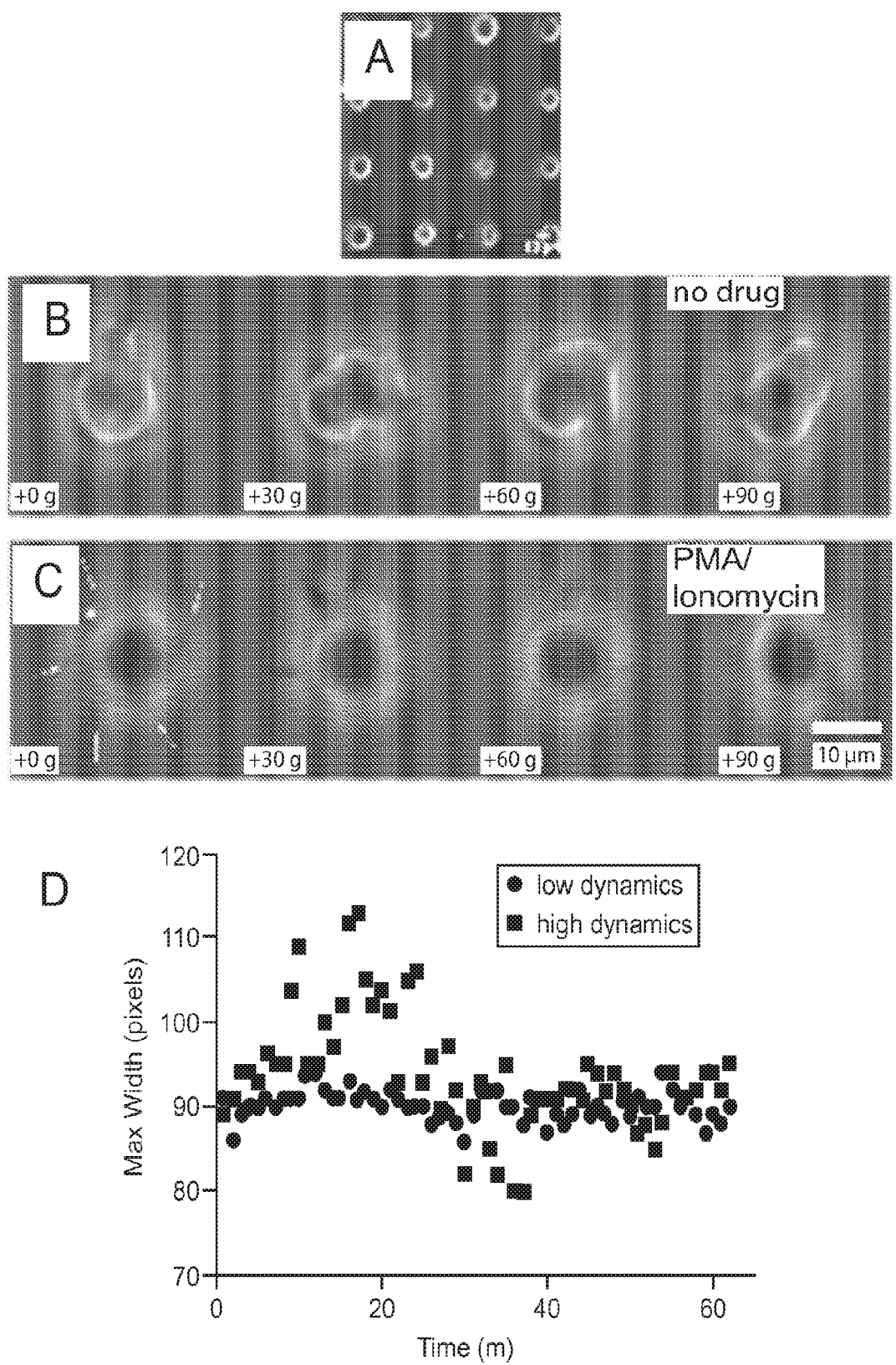
FIG. 4, Panels A-F depict imaging the membrane dynamics of T-lymphocytes. Panel A: A representative field of arrayed Jurkat cells. Panel B: Time-lapse images illustrating the dynamics of a single immobilized Jurkat Cell. Panel C: PMA/ionomycin treated Jurkat cells are more homogeneous with respect to cell shape but have increased membrane microspikes (arrows). Panel D: Trajectories of maximum cell width for representative cells of high and low membrane dynamics. Panel E: Population-level analysis of maximum width for cells treated with or without PMA/ionomycin. Panel F: Population-level analysis of microspike dynamics over 15 minutes for cells treated with or without PMA/ionomycin.
Figure 4:
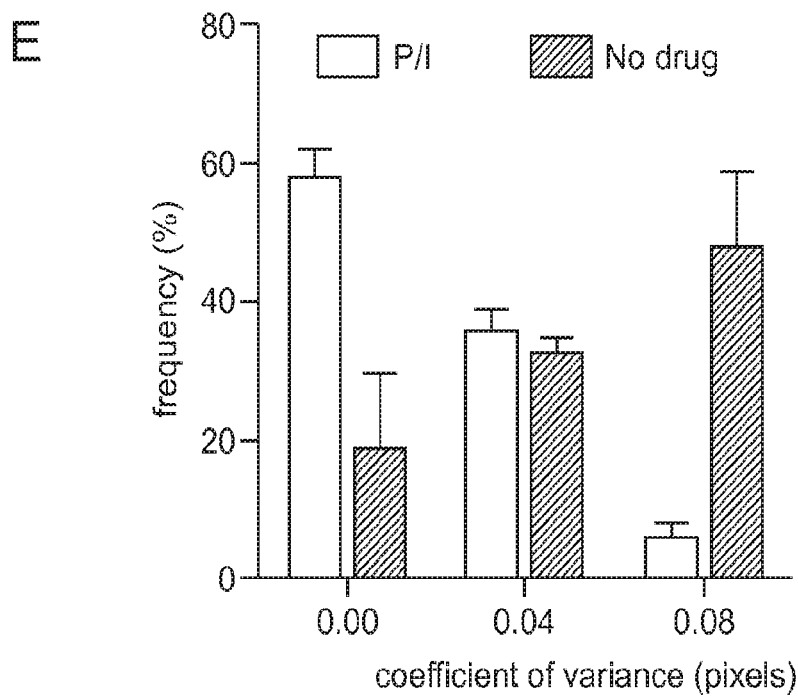
Figure 4:
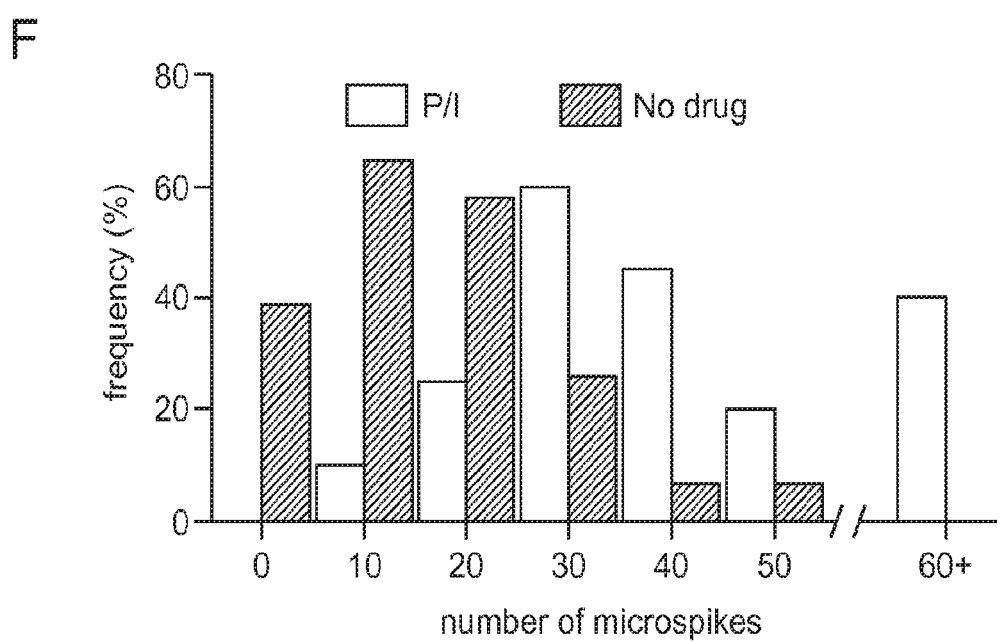
Figure 9:
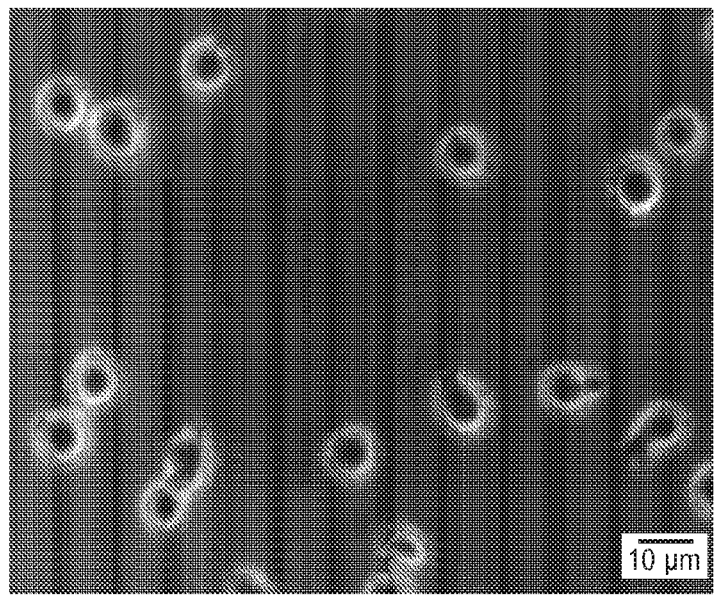
FIG. 9, Panels A-B show a still frame of unmodified (Panel A) and $C_{16}$ dialkylphosphoglyceride-modified DNA labeled (Panel B) cells on naked glass surfaces.
Figure 9:
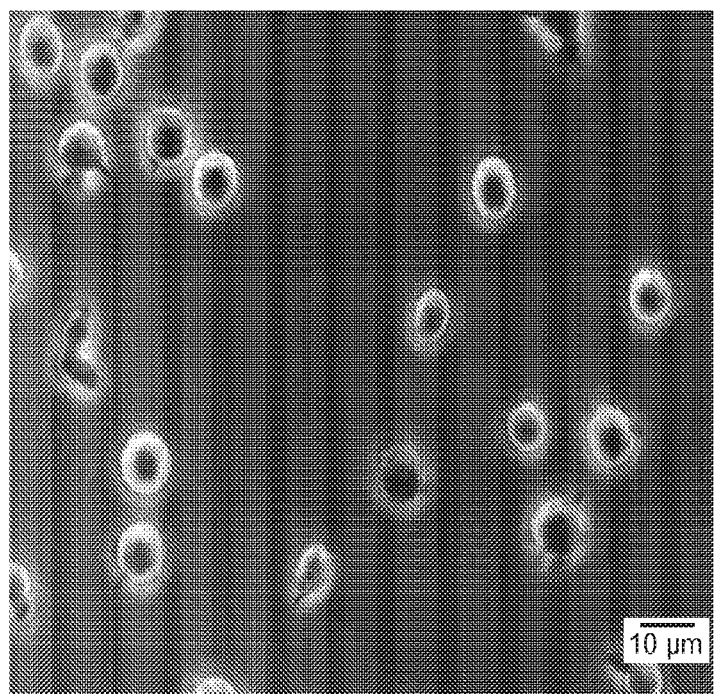
Figure 10:
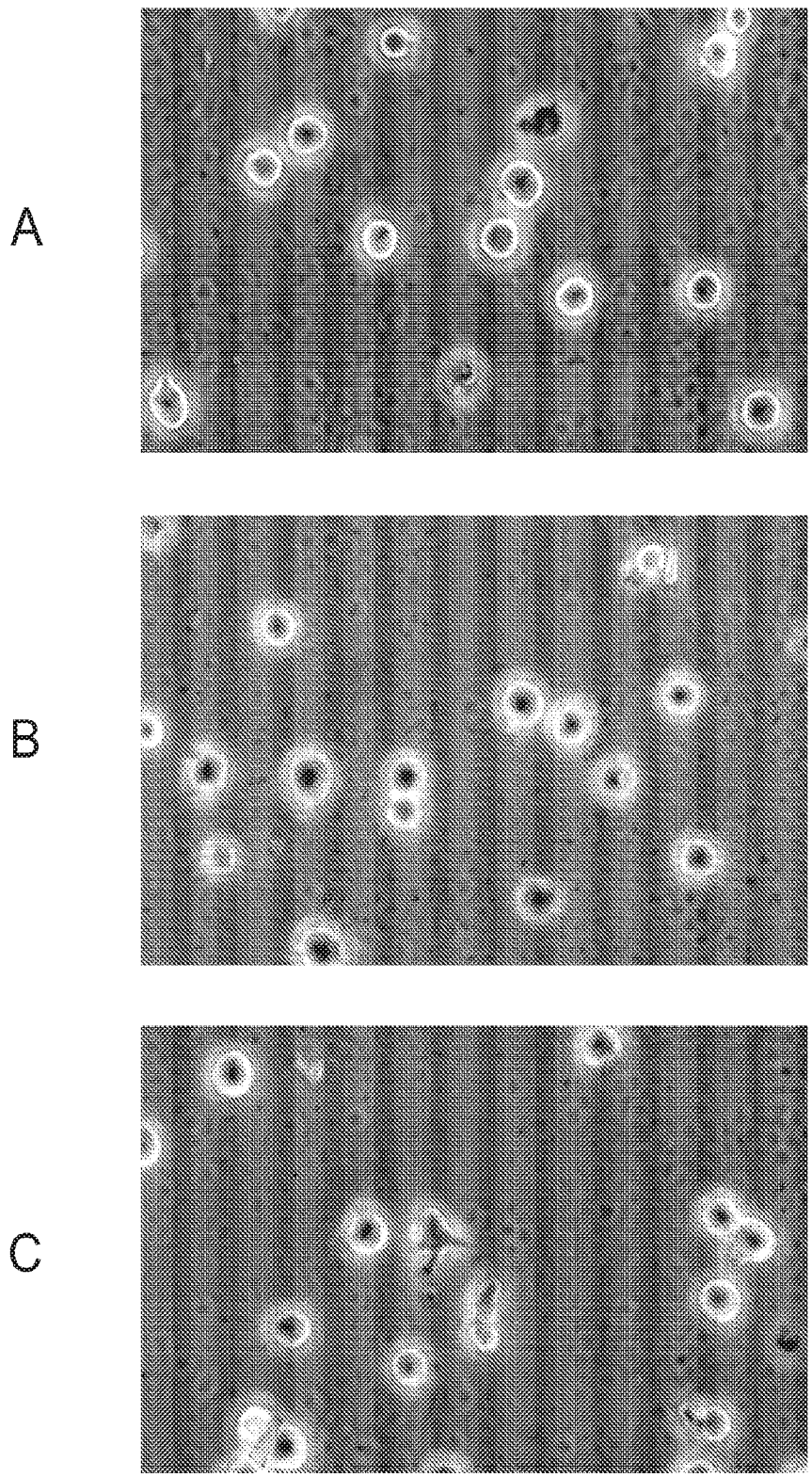
FIG. 10, Panels A-C show single frames of $C_{16}$ dialkylphosphoglyceride-modified DNA-labeled-Jurkat cells over bare glass (Panel A), polylysine coated glass (Panel B), and passivated glass (Panel C).
Figure 11:
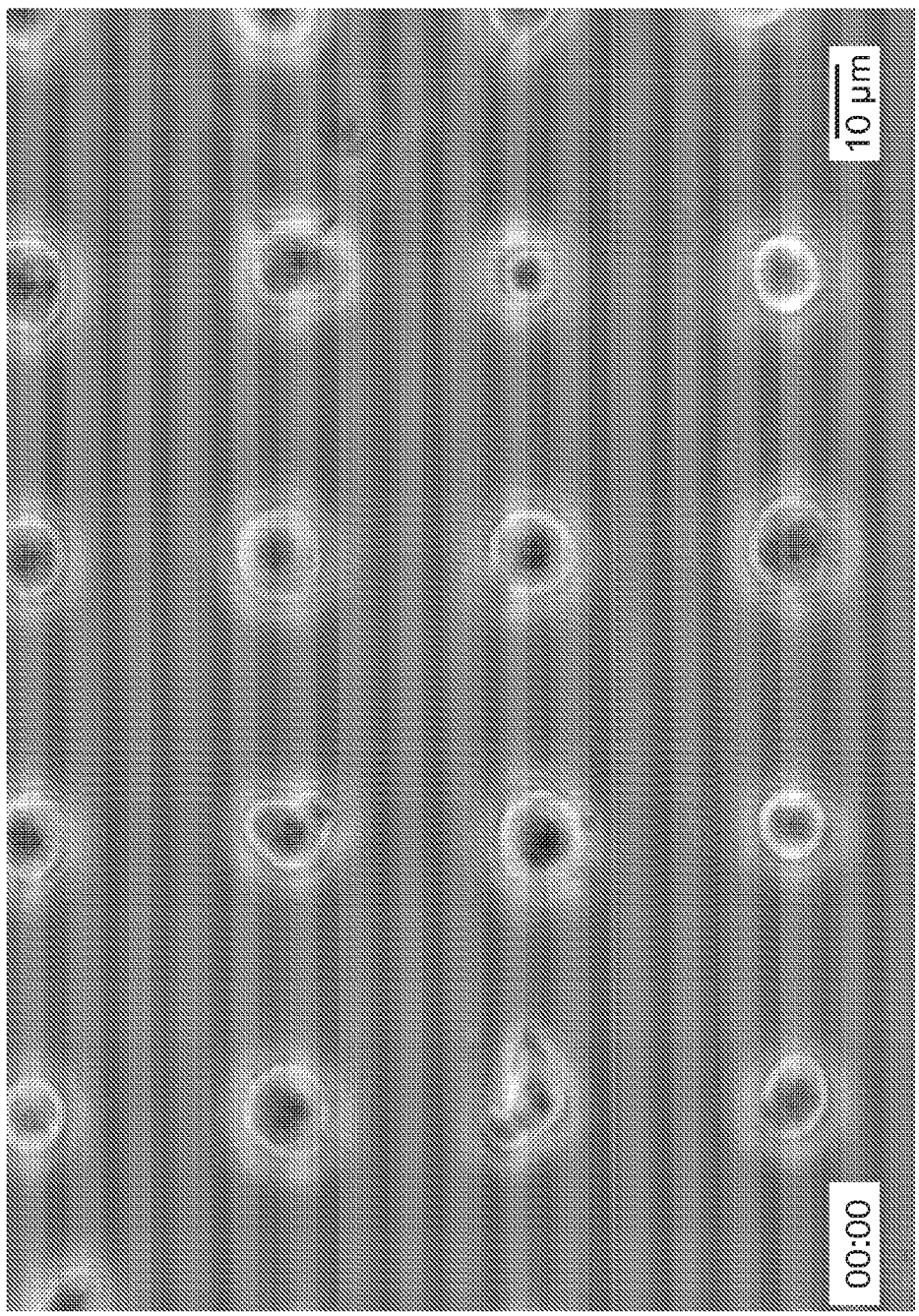
FIG. 11 shows a single frame from a 400×timelapse video of $C_{16}$ dialkylphosphoglyceride-modified DNA-labeled-Jurkat cells immobilized on a passivated surface with grid of 5-7 µm DNA spots.
Figure 12:
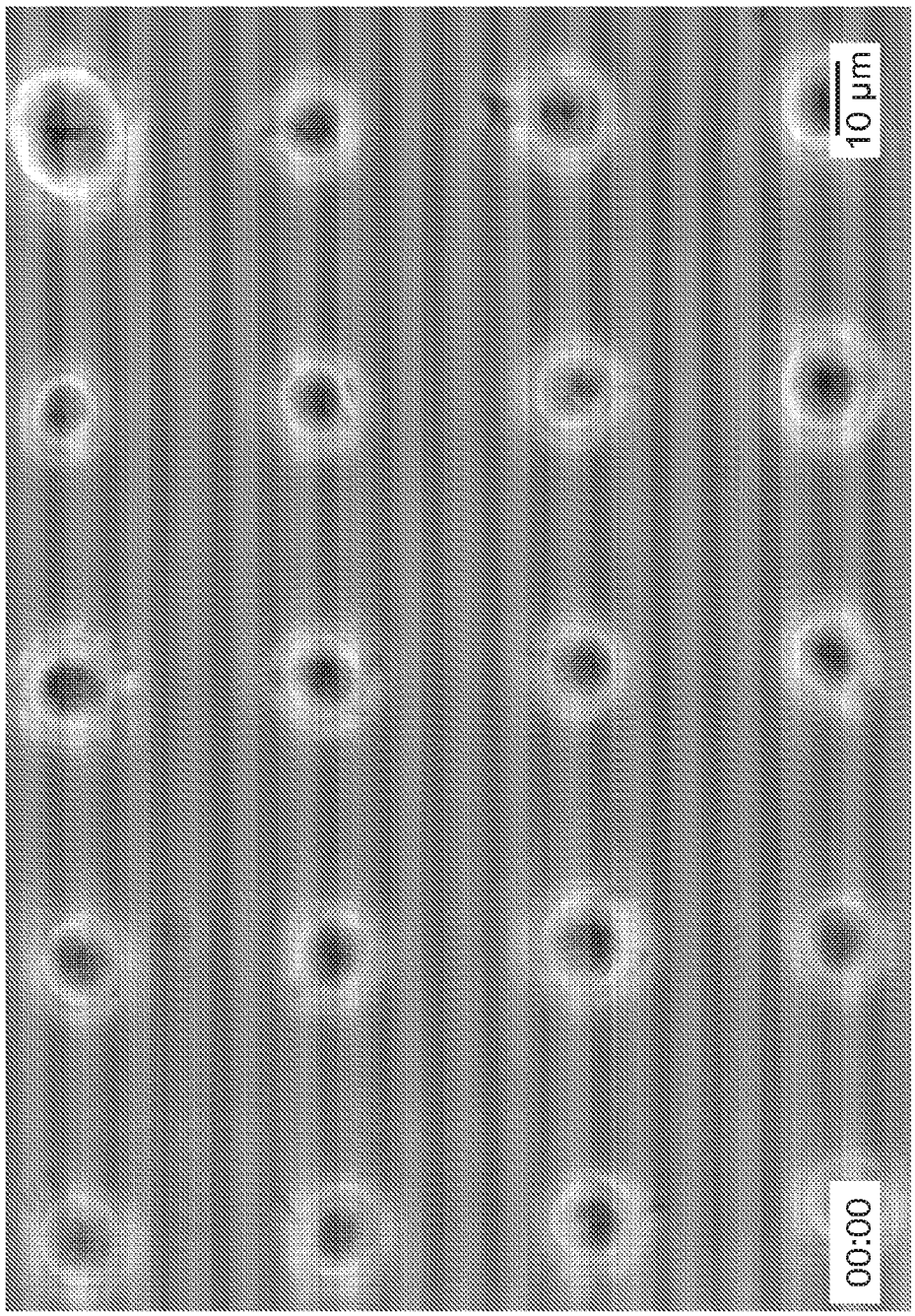
FIG. 12 shows a single frame from a 400×time-lapse video of PMA/ionomycin activated $C_{16}$ dialkylphosphoglyceride-modified DNA-labeled-Jurkat cells immobilized on a passivated surface with grid of 5-7 µm DNA spots.

First, it was first confirmed that the morphology of $C_{16}$ dialkylphosphoglyceride-modified polynucleotide-modified cells was similar to unmodified cells when imaged in suspension over glass (FIG. 9, Panels A-B). Small, 5-7 μm patches of DNA on passivated glass surfaces were prepared using a Bioforce NanoEnabler and the presence of DNA on the surface was confirmed by annealing a FITC-labeled complementary strand (FIG. 9, Panels A-B; FIG. 10, Panels A-C; and FIGS. 11-12). It was also confirmed that Jurkat cells were unable to interact with the passivated glass surface. Jurkat cells bearing $C_{16}$ dialkylphosphoglyceride-modified complementary sequences were immobilized on these patches by DNA hybridization (FIG. 4, Panel A). Time-lapse imaging revealed a heterogeneous population of cells with a subpopulation undergoing rapid changes in cell shape on the minute timescale (FIG. 4, Panels B, D, and E; FIG. 9, Panels A-B; FIG. 10, Panels A-C; and FIGS. 11-12). Interestingly, small molecule T-cell activators PMA and ionomycin (P/I) seemed to reduce the heterogeneity of the population (FIG. 4, Panel D). At higher magnification, many cells also extended membrane microspikes from the cell surface (FIG. 4, Panel C and FIG. 12). These appeared to be distinct from the gross morphological changes observed at lower magnification, as they were enhanced, rather than reduced, by P/I treatment (FIG. 4, Panel F). Treatment with nocodazole, a microtubule depolymerizer, completely blocked these microspikes. Treatment with latruncluin A, an actin depolymerizer, also blocked the formation of the microspikes, but also led to the rapid growth of long tubules from the cell surface that extended several cell diameters in length and would occasionally form stable linkages with neighboring cells. Subsequent addition of nocodazole led to retraction of the membrane tubules. However, tubules forming linkages with neighboring cells were protected from nocodazole treatment.

Example 6: Resazurin Cell Viability Assay

Cells were labeled with DNA and washed as described in the previous Examples. For each cell type, optimal cell density was determined for each well of a 96-well plate. Resazurin (10 μl) was added to culture for 24 hours before fluorescence was read with excitation and emission wavelengths at 530 nm and 590 nm, respectively, using Molecular Devices SpectraMax M5 on three consecutive days. The change in fluorescence intensity over time was used as a proxy for cell growth rates. Fluorescence was log transformed and plotted against time for lipid-modified and untreated cells. Slopes and intercepts of the growth rates for the two cell treatments were compared using ANCOVA (GraphPad Prism) to determine if doubling time was inhibited by DNA treatment.

Results

Figure 8:
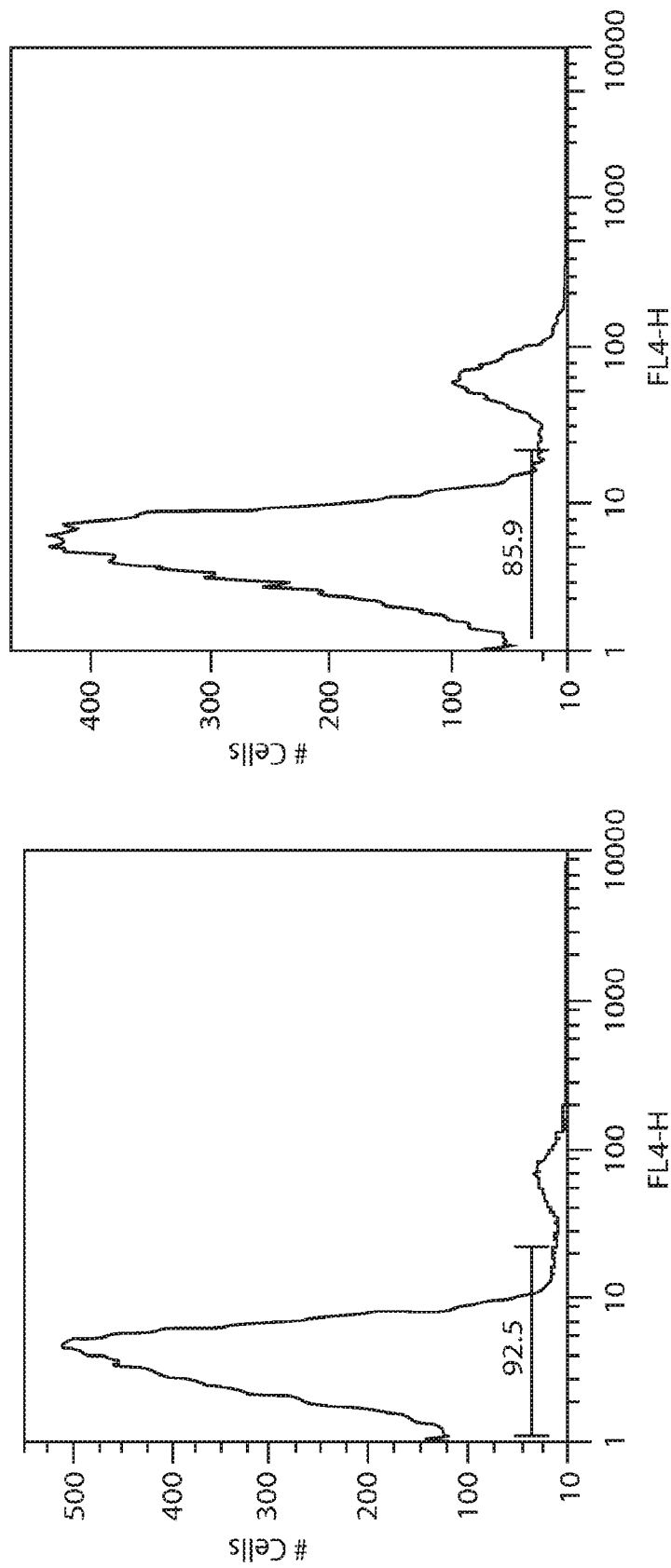
FIG. 8, Panels A-C depict viability and proliferation of membrane-anchored polynucleotide modified cells. Panel A: Flow cytometry viability analysis of unlabeled (left) and $C_{16}$ dialkylphosphoglyceride-modified DNA-labeled (right) populations of Jurkat cells. Live cell population is indicated by the gate at the bottom of the plot. Panel B: Representative growth curve for Jurkat cells. Panel C: Tabulated data from Panel B for all analyzed cell types.
Figure 8:
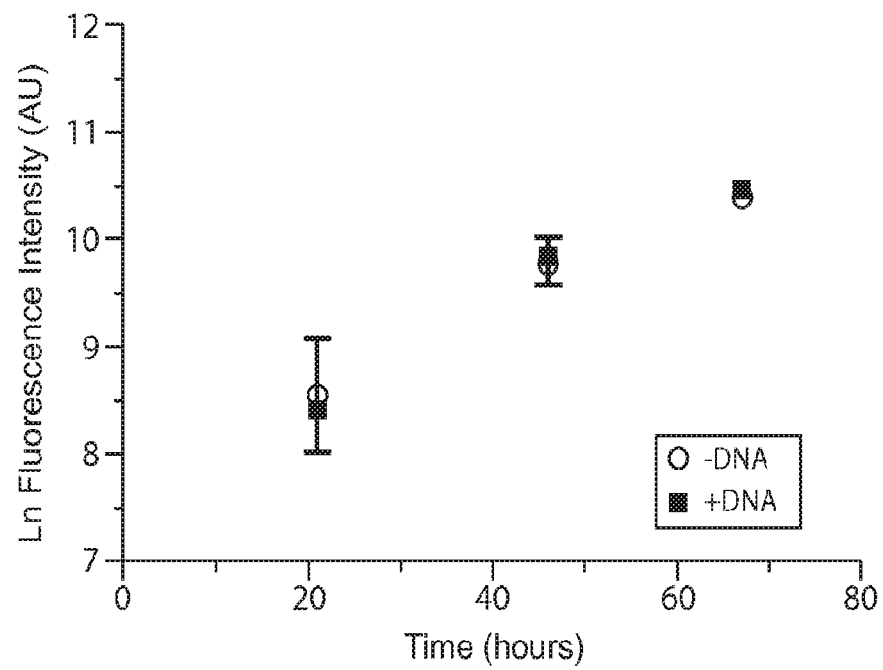

It was found that when labeling Jurkat cells with freshly prepared stocks of $C_{16}$ dialkylphosphoglyceride-modified 100mer polynucleotides, cell viability approached or exceeded 90%, similar to controls treated with PBS alone and to cells labeled by glycan engineering or direct conjugation to lysine side chains (FIG. 8, Panels A-C). Cell proliferation in labeled cell populations was also measured using the resazurin assay. Jurkat cells showed no differences in their rate of proliferation after being modified with of $C_{16}$ dialkylphosphoglyceride-modified polynucleotides. Similar results were obtained with MCF-10A, HeLa and MEF cells (FIG. 8, Panels A-C).

Example 7: DNA Labeling of Cells

Membrane-anchored DNA molecules: Jurkat cells were washed with ice cold calcium and magnesium free PBS three times, and ($10^6$) cells were resuspended in 48 μl of PBS. They were labeled by addition of 1 μl of 50 μM membrane-anchored DNA polynucleotides in distilled water of a 100 bp sequence, making a final DNA concentration of 5 μM. The membrane-anchored DNA nucleotides were synthesized as described in Example 2, and comprised structures of the general type as shown in FIG. 13, Panels A-B.

Figure 20:
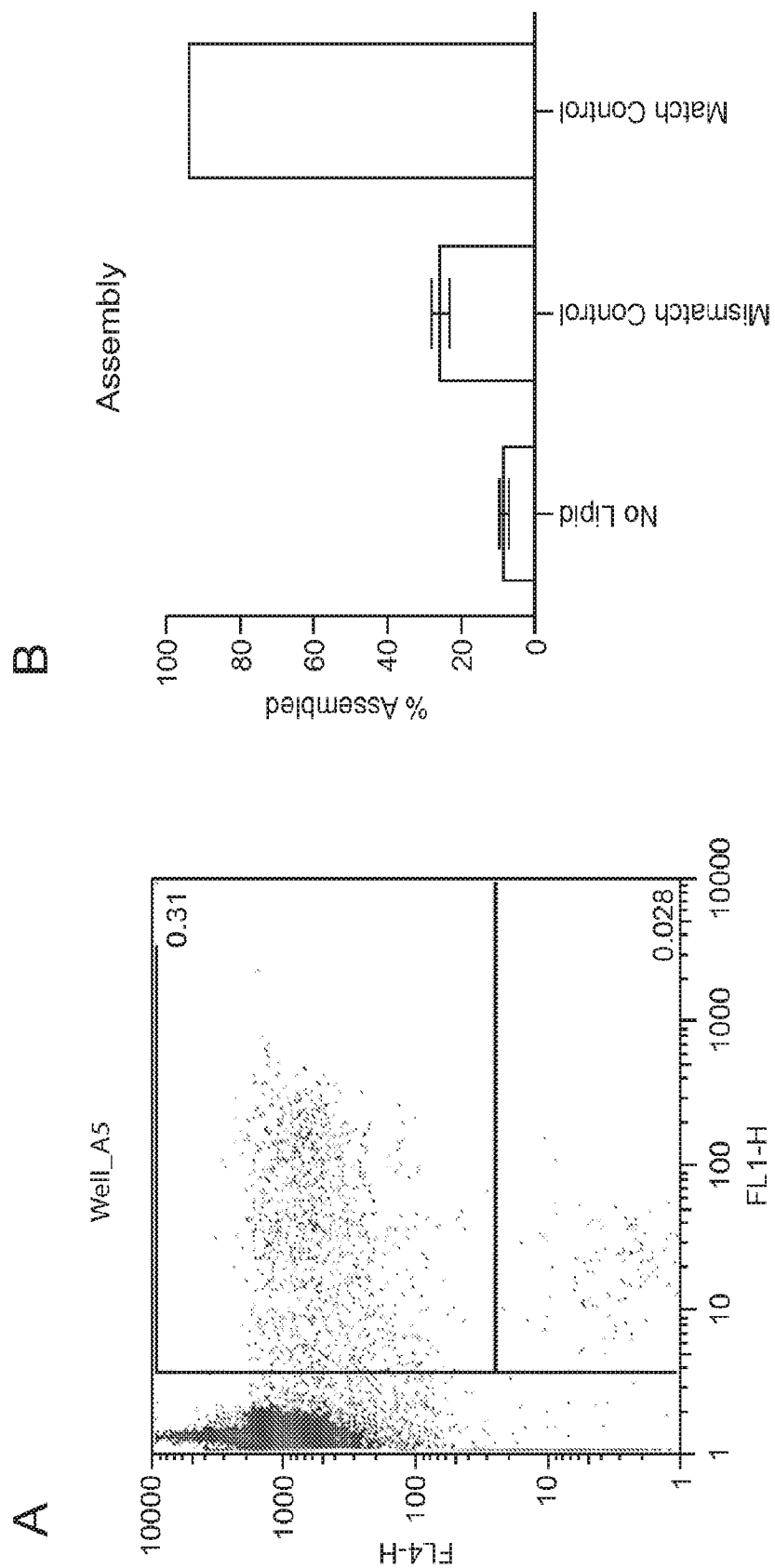
FIG. 20, Panels A-D show examples of cellular assembly using membrane anchored DNA polynucleotides according to certain embodiments of the instant disclosure. Cells were prepared at 1×10$^6$ cells/mL, gently shaken for 40 minutes on ice. Cells were labeled using membrane anchored DNA polynucleotides according to certain embodiments of the instant disclosure, wherein red cells were labeled with $(CAGT)_5$; green cells were labeled with $(ACTG)_5$. Cells were added together at a ratio of 50:1 Red:Green and visualized.
Figure 20:
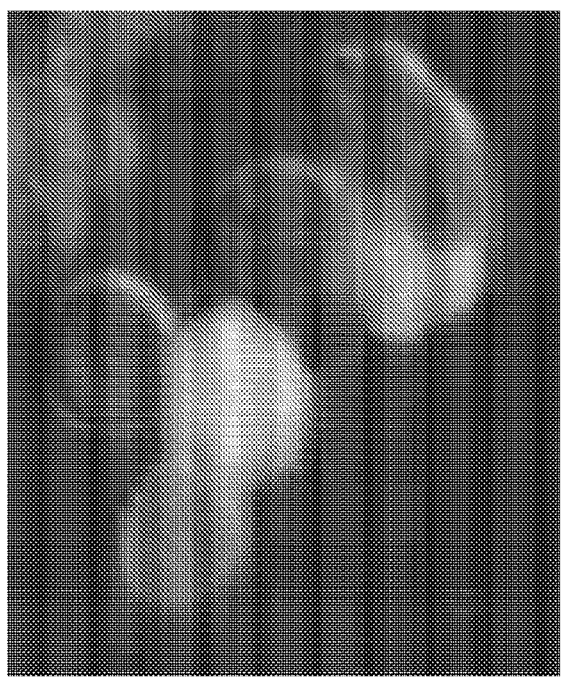
Figure 20:
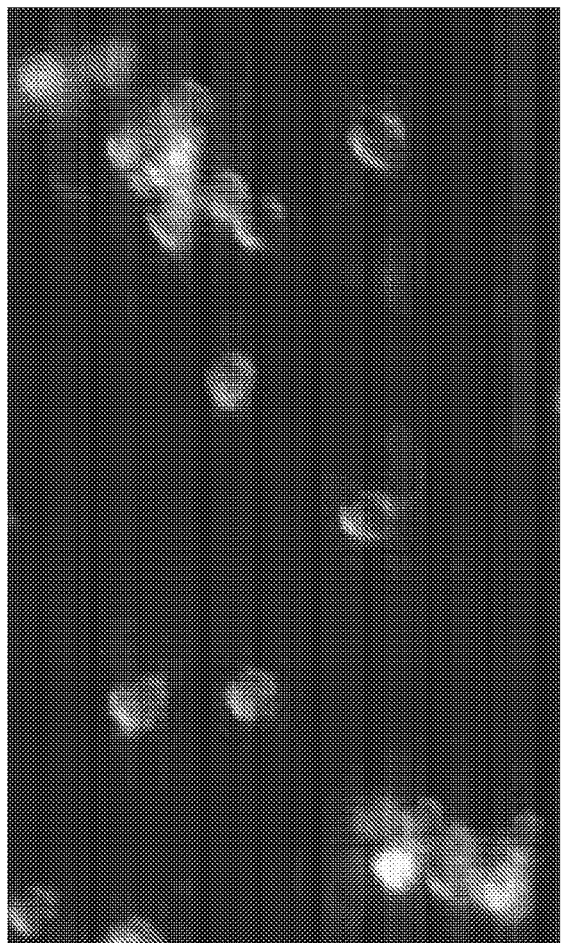

This was followed by gentle agitation by slow vortexing for 5 minutes at room temperature. Subsequently, 1 μl of 50 μM lipid-DNA of a 20 bp sequence (of a general type as is shown in FIG. 13, Panel B) followed by gentle agitation by slow vortexing for 5 minutes at room temperature. After DNA addition, all cells were washed in ice-cold PBS three times to remove residual lipid-DNA before incubating in 50 μl of 20mer complimentary 6-FAM modified polynucleotide (1 μg/ml, Operon) for 30 minutes at 4° C., protected from light. Cells were washed one time with ice-cold PBS before resuspending in LIVE/DEAD® Fixable Dead Cell Stain (Invitrogen) for 15 minutes at 4° C. Cells were washed one last time before flow cytometry analysis (FIG. 20, Panel A). All reported values are the average of 3 independent measurements. Median fluorescence increase (MFI) was calculated as the fold increase of fluorescence levels over unmodified cells. An illustration of this general scheme is depicted in FIG. 13, Panel C.

Example 8: Assay for Cell Attachment and Dynamic Membrane Observations

Preparation of DNA arrays: 5'-amino-modified DNA was prepared in a buffer of 450 mM NaCl, 50 mM dibasic sodium citrate, 50 mM dibasic sodium phosphate, and 1% NaCNBH$_3$. DNA was patterned onto aldehyde-silanized glass (Schott) using a micropipette and incubated 12 hours in a humidifier chamber. Slides were reduced with NaBH$_4$ and passivated with both SigmaCote (Sigma) and Plutonic F108 before use.

Cells incorporating lipid-DNA were allowed to settle onto patterned glass within a PDMS-based flow cell for 30 minutes at room temperature. Only cells hybridized to the surface via DNA were retained when the surface was washed with PBS. Patterned cells were imaged with a Zeiss Axiovert 200M at 40×magnification (FIG. 20, Panels B-D). Images were analyzed manually.

Example 9: Synthesis of a Membrane-Anchored DNA Polynucleotide Comprising a Long DNA Polynucleotide A membrane-anchored DNA polynucleotide was made by PCR, using New England Biosciences Phusion Master Mix. As the DNA template, a DLL1 gene of size 2.2 kb was used. The following modified primers were used:

```
                                      (SEQ ID NO: 44)
5'-Lipid-ATG GGC ACT CGG TGC GCG CTG-3'

(SEQ ID NO: 45)
5'-Biotin-GAC GCA CTC ATC CTT CTC CTC GG-3'
```

Figure 21:
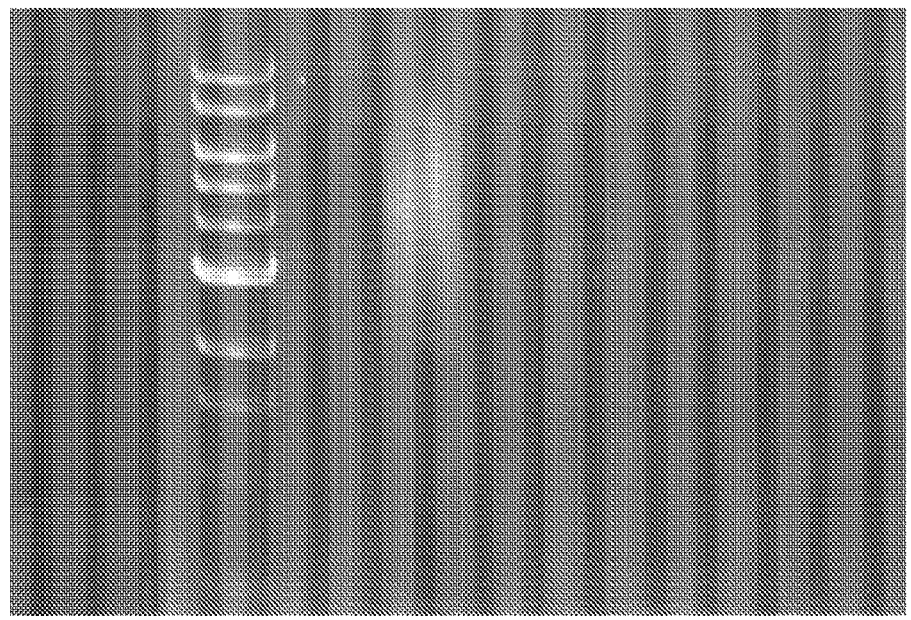
FIG. 21, Panels A-B show that membrane anchored polynucleotides can comprise a polynucleotide exceeding 2kb. Panel A depicts an agarose gel used to confirm the presence of a membrane-anchored DNA polynucleotide comprising a 2.2kb polynucleotide. Panel B depicts flow cytometry data showing incorporation of this membrane-anchored DNA polynucleotide into Jurkat cells.
Figure 21:
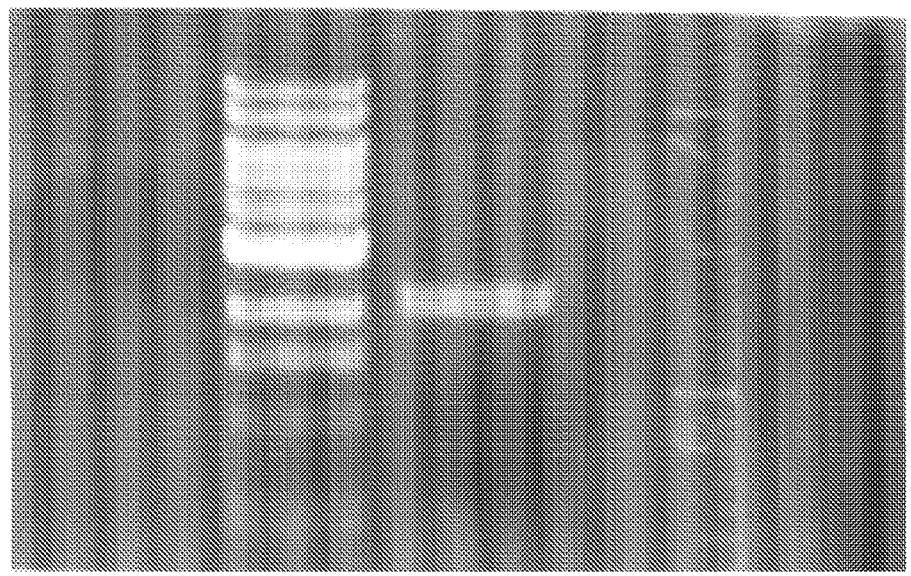
Figure 21:
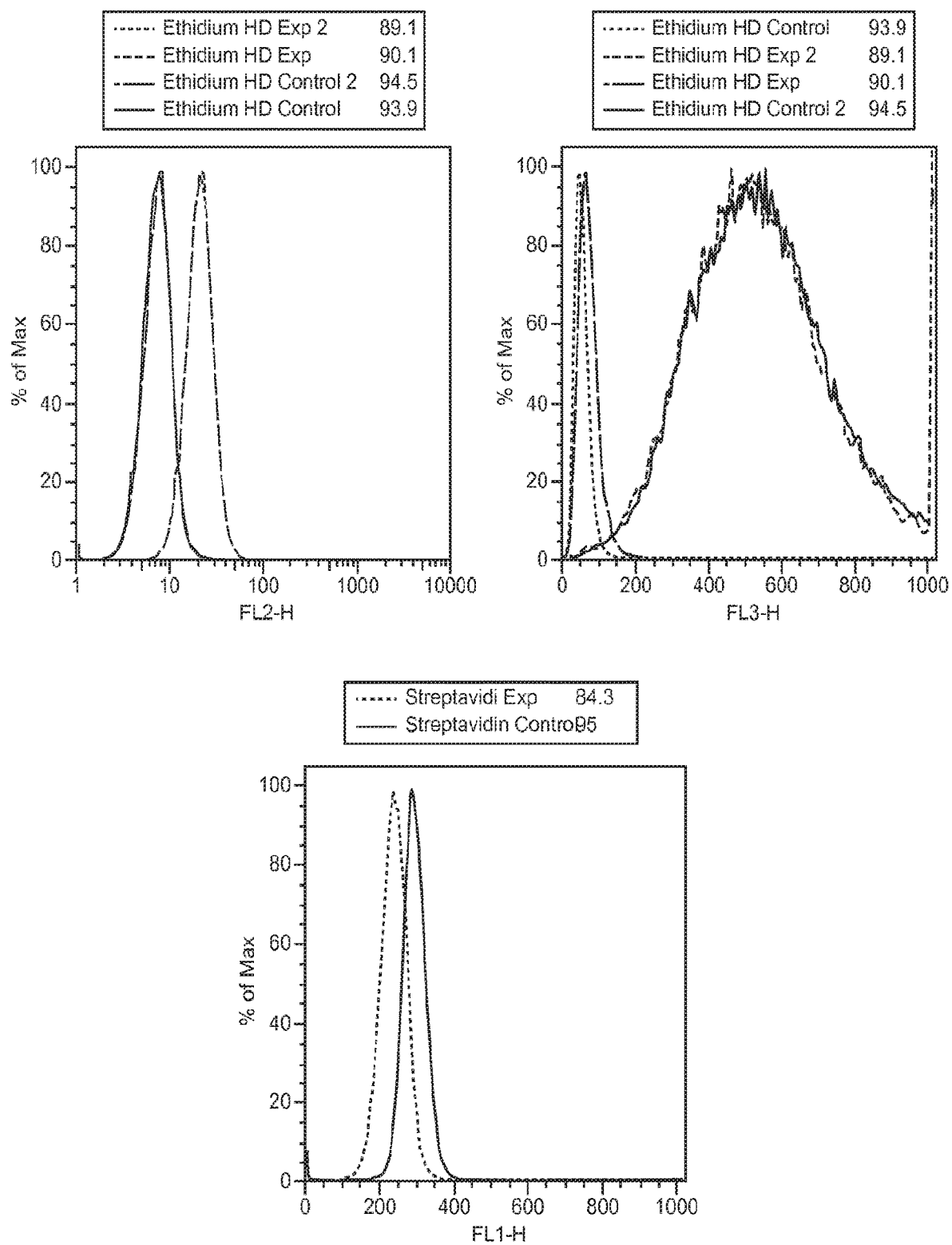

To verify the membrane-anchored DNA polynucleotide PCR product, a 1% agarose gel with ethidium bromide was used to visualize the size of the PCR product. The dialkylglyceride-modified DNA polynucleotide ran as a smear on the gel, presumably because the lipid tail led to self-assembly of the dsDNA strands into heterogeneous micellar or non-covalently interacting higher molecular structures. To collapse the smear down to a single band, digest with the EcoN1 restriction enzyme was completed to remove the lipid tail of the membrane-anchored DNA polynucleotide. There was a restriction site at the 5' end of the DNA. A 5 minute digest at 37° C. was completed. After the digest, a second agarose gel confirmed the membrane-anchored DNA polynucleotide PCR product (FIG. 21, Panel A).

As previously, the Jurkat cell line was used for cell labeling experiments. Before the start of the experiment, 2 cell viability measurements were made using the Invitrogen Countess machine prior to starting the experiment. The viability readings were 94% and 97%.

Briefly, 4 aliquots of 1 million Jurkats were washed with PBS 3×, then 2 aliquots of cells were suspended in 50 uL of PBS with 47.11 ug of the membrane-anchored DNA polynucleotide. The other 2 aliquots of cells were suspended in 50 uL PBS as a control. The cell suspension was left on a shaker for 5 minutes, then washed 3×with PBS. To test for membrane-anchored DNA polynucleotide incorporation into the cell membrane, FITC-Streptavidin and Ethidium Homodimer were used at 2 ug/mL and 2 uM respectively. To each solution, the Invitrogen LIVE/DEAD® Fixable Far Red Dead Cell Stain Kit was diluted as written in the manual. Two aliquots of 1 million Jurkats, one aliquot of lipid-conjugate DNA and one aliquot of non-labeled control cells, were incubated in 50 uL of the FITC-Streptavidin/ LIVE/DEAD® solution for 20 minutes at 4° C. in the dark. The other two aliquots of 1 million Jurkats, one aliquot of membrane-anchored DNA polynucleotide and one aliquot of non-labeled control cells, were incubated in 50 uL of the Ethidium Homodimer/LIVE/DEAD® for 20 minutes at 4° C. in the dark. After 20 minutes, each cell aliquot was washed 3×with PBS and flow cytometry was performed on the FACS Calibur.

The fluorescence of FITC-Streptavidin or Ethidium Homodimer was only taken into consideration for live cells. This was obtained by gating on the population of cells that did not incorporate the LIVE/DEAD® stain from invitrogen. FIG. 21, Panel B shows the flow cytometry data. FL-1 is the green emission channel. FL-2 and FL-3 is the red emission channel. The numbers next to the sample names in the key are the viability percentages based on gating on the FL-4 (far-red emission) channel.

Materials and Methods

The following are general materials and protocols used in Examples 10-14 below.

Oligonucleotide Sequences

Oligonucleotide sequences are as follows:

```
A:
                                      (SEQ ID NO: 46)
5'-linker SH-ACTGACTGACTGACTGACTG-3';

B:
                                      (SEQ ID NO: 47)
5'-linker-SH-CAGTCAGTCAGTCAGTCAGT-3';

Lipid DNA A:
                                      (SEQ ID NO: 48)
5'-dialkyl-(T)80-ACTGACTGACTGACTGACTG-3';

Lipid DNA B:
                                      (SEQ ID NO: 49)
5'-dialkyl-(T)80-CAGTCAGTCAGTCAGTCAGT-3'
```

General Materials and Reagents

Oligonucleotides were synthesized on an Expedite 8909 using standard phosphoramidite chemistry. Phosphoramidites were purchased from Glen Research and AZCO Biotech. Modified oligonucleotides were purified on an Agilent 1200 HPLC equipped with a semiprep Zorbax reversed phase C18 (oligos A and B) or semiprep Phenomenex C4 (Lipid DNA A and B) column and running a gradient of ACN in 0.1 M TEAA from 8% to 80%. Purified oligonucleotides were extensively lyophilized prior to use. NHS-modified DNA was prepared as described in Hsiao S C, et al. (2009) *Langmuir* 25, 6985-6991 and Selden N S, et al, (2012) *J. Am. Chem. Soc.* 134, 765-768; the disclosures of which are incorporated herein by reference.

Sorafenib was a gift from Kevan Shokat (UCSF0 and used at 10 µM. PIK-90 was purchased from Calbiochem and used at 2 µM. High activity DNase was purchased from Ambion. Ethidium homodimer-1 was purchased from Invitrogen and used at 1 µM.

Antibodies, Growth Factors, and Inhibitors

The following antibodies were used for western blot: E-cadherin (BD Biosciences), tubulin (Sigma-Aldrich), phospho-Erk and phospho-Akt (Cell Signaling Technology), pan-Ras (Calbiochem), goat anti-mouse-HRP, and goat anti-rabbit-HRP (Thermo Scientific). The following antibodies were used for immunofluorescent staining: GM130, β-catenin (BD Biosciences), Ki6-integrin, laminin-5 (Millipore), cleaved caspase-3 (Cell Signaling Technology), Ki-67 (Sigma-Aldrich), gp135 (a gift from Keith Mostov, UCSF), Alexa Fluor 488- and 568-conjugated goat anti-mouse, anti-rat, and anti-rabbit antibodies (Invitrogen). F-actin was stained with Alexa Fluor 488- or 568-conjugated phalloidin (Invitrogen). LY294002 and PD325901 (Calbiochem) were used at 20 µM and 200 nM, respectively. TURBO RNase (Invitrogen) was used at a concentration of 10 U/ml.

Cell Lines and Cell Culture

MDCK cells were provided by Keith Mostov (UCSF) and cultured as described by Martin-Belmonte, et al, (2007) *Cell*, 128, 323-334; the disclosure of which is incorporated herein by reference. MCF10A cells were provided by Jay Debnath (UCSF), and MCF10AneoT cells were obtained from the Karmanos Cancer Institute (Detroit). Both cell lines were cultured as in Dawson et al. (1996) *Am J. Pathol.* 148,313-319 and Debnath et al. (2003) *Methods* 30, 256-

268; the disclosures of which are incorporated herein by reference. 3D on-top cultures were performed as previously described using growth factor-reduced lrECM lots with protein concentrations between 9 and 11 mg/ml (Matrigel; BD Biosciences). Cell lines expressing H2B-RFP proteins were prepared by transduction with lentivirus derived from pHIV-H2B-mRFP (Addgene; plasmid 18982). H2B-eGFP was cloned from Addgene plasmid 11680 and ligated into pHIV to produce pHIV-eGFP. Lentivirus was produced at the UCSF Sandler Lentiviral Core.

Cell Surface Labeling and Programmed Assembly

Cell surface labeling was performed as described below in Examples 1-9. Cells were lifted by an incubation in 0.04% EDTA until cells rounded, followed by a 0.05% trypsin pulse. Trypsin was quenched by soybean trypsin inhibitor (Sigma-Aldrich). Cells were washed three times with base medium and then labeled with NHS-DNA for 30 min or with dialkylphosphoglyceride-DNA for 5 min at room temperature followed by three washes with base medium. DNA-labeled cells were filtered through a 40 µm mesh, counted, mixed at greater than 1-50 ratios in polypropylene tubes, centrifuged, and gently resuspended. Aggregates were purified directly into eight-chamber slides containing 3D assay media using a FACSAriaII or FACSAriaIII flow cytometer equipped with a 130 µm nozzle and a sheath pressure of 10 psi.

Microscopy

Time-lapse images of aggregates were acquired on a Zeiss 200M inverted fluorescence microscope equipped with an XCite argon light source and a Hamamatsu camera. Field positions were programmed into Slidebook 5.0 software, and images were acquired at 30 min intervals. Samples were maintained in a humidified chamber at 37° C. and 5% CO2. Phenotypes were scored in Slidebook 5.0 software after acquisition. Microtissues that merged with other microtissues or single cells were not scored due to confounding effects on cell motility.

Immunofluorescence Analysis and Image Acquisition 3D cultures were stained as previously described in Debnath et al., 2003. Confocal images were taken at the equatorial plane of the developing microtissues and were acquired on an inverted Zeiss LSM 51.0 NLO laser-scanning microscope (UCSF Laboratory for Cell Analysis). All imaged aggregates contained at least one CFP-labeled nucleus, although not necessarily in the plane of the confocal slice. Polarity, proliferation, and apoptosis counting were performed on a Nikon TiE inverted microscope equipped with a CSU-X1 confocal head. Channel intensities were adjusted linearly and equally across all images in each experiment using ImageJ and Adobe Photoshop software.

Quantification of Basal Extrusion and Multicellular Protrusion Phenotypes

Apoptotic cells were excluded from phenotype quantification, as judged by cell morphology (FIG. 27, Panels A-F) or uptake of ethidium homodimer-1 (FIG. 28, Panels C, G, and H). Extruding microtissues contained a single H2B-GFP-expressing cell pushed beyond the phase-bright boundary formed by the surrounding cells. Multicellular protrusions began with a single H2B-GFP-expressing cell that led the translation of the surrounding cells without becoming disconnected from the microtissue. H2B-GFP-expressing cells that broke away from tissues and moved alone were scored as protruding cells due to their altered morphology and motility.

Confocal Imaging of Phenotypes in Heterogeneous MCF10ARas/MCF10AWT Microtissues

Z-stacks of basal extrusion and multicellular protrusion phenotypes were imaged on a Zeiss Observer.Z1 microscope equipped with a CSU-X1 spinning disk confocal head using AxioVision software. Image intensities were adjusted linearly in FIJI.

Figure 22:
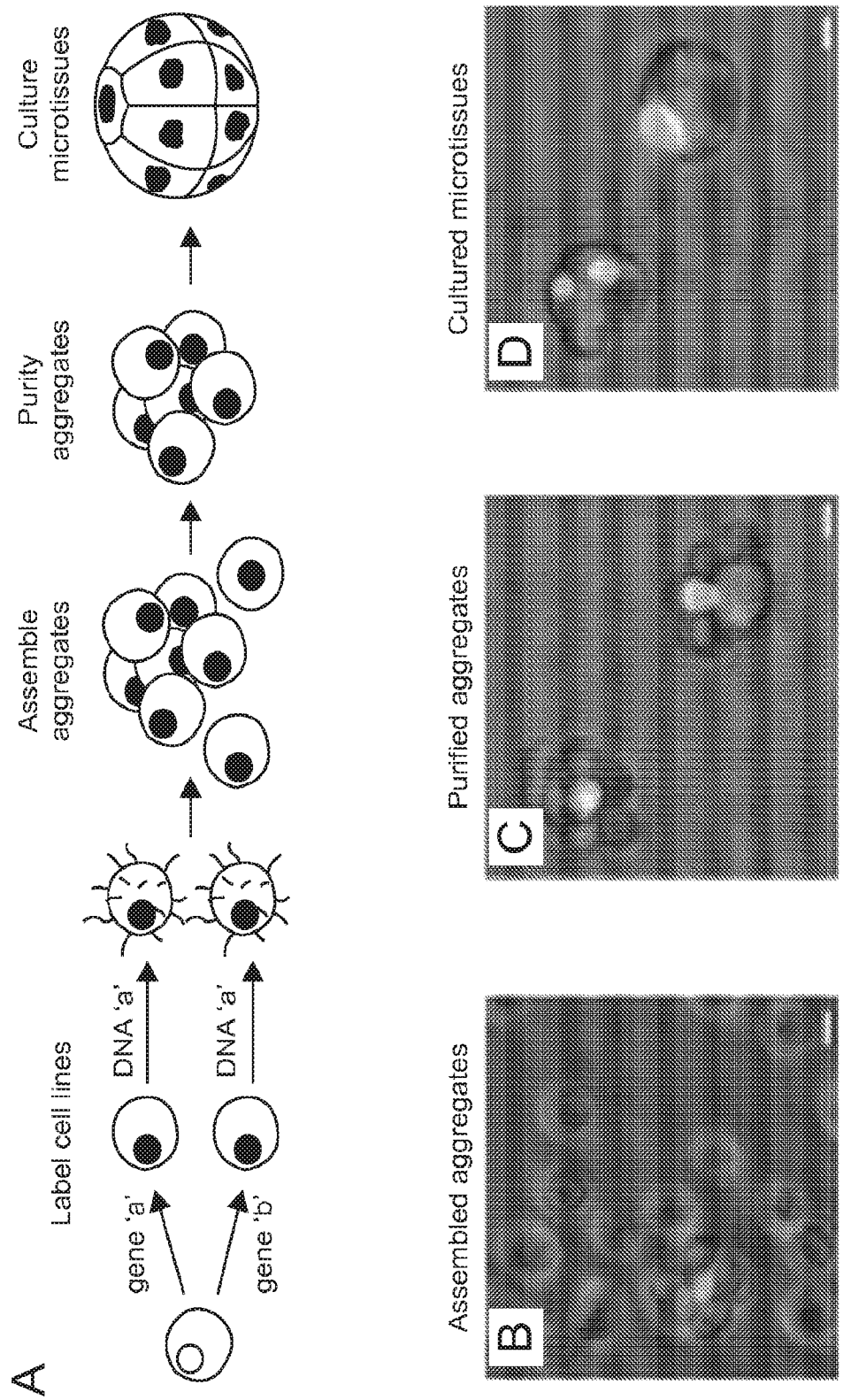
FIG. 22, Panels A-E depict programming the assembly of mosaic epithelial aggregates of defined size, composition, and initial cell-to-cell connectivity. Panel A: Scheme for the programmed assembly of mosaic epithelial microtissues. Panel B: Single H2B-GFP-expressing MCF10A cells assembled 1:50 with H2B-RFP-expressing MCF10A cells. Panel C: Aggregates after purification by FACS. Panel D: MCF10A aggregates as shown in Panel C condensed into rounded microtissues after 8.5 hr culture in lrECM. Panel E: Time series of MCF10A aggregate condensation over 48 hr, showing motion of fluorescently labeled nuclei during condensation of an aggregate (insets) into a microtissue. Scale bars=10 µm FIG. 23, Panels A-E depict DNA-mediated programmed assembly and 3D culture of epithelial cell aggregates, related to FIG. 22, Panels A-E. Panel A: Proliferation curves of MCF10A cells labeled with NHS-DNA compared with untreated cells as determined by resazurin cell viability assay. Panel B: Representative images of 1-to-1 assembly reactions made with red- and green-labeled MCF10A or MDCK cells. Cells were labeled with either mismatched or complementary NHS-DNA. Panel C: FACS plot differentiating single MCF10A cells containing either H2B-GFP or H2B-mCherry (left) and assembly reactions of MCF10A cells containing both red and green cells (right). Cells were mixed at a 1-to-50 ratio. Events falling into the top-right quadrant were purified as assemblies. Panel D: Representative image of sorted MDCK aggregates assembled with complementary lipid-DNA. Panel E: Circularity of assembled aggregates in lrECM was assessed from the phase dark border of aggregates over time. Normalized average circularity was plotted by assigning a value of 1 to the average circularity at 24 hr, and 0 to the average circularity at time zero. The average value of 176 observations is plotted as a function of time.
Figure 22:
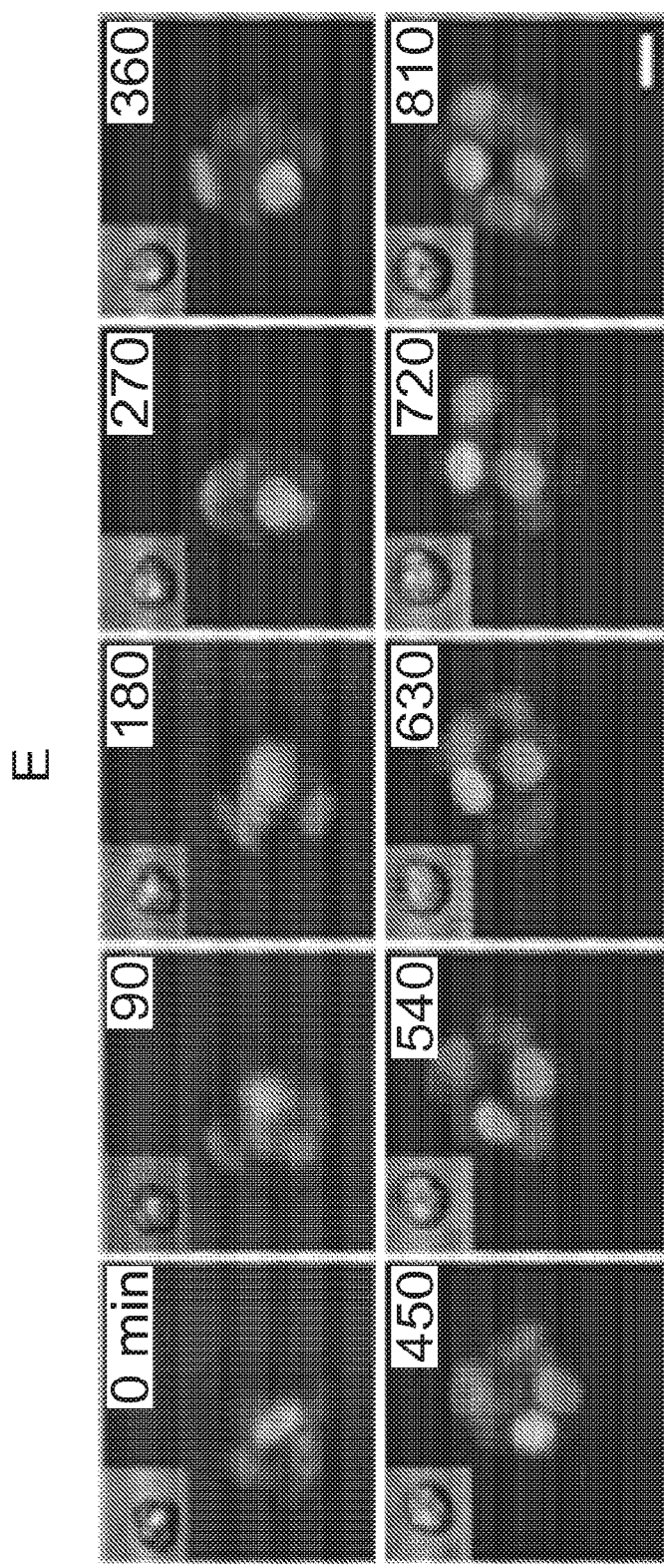

Example 10: Programmed Assembly Generates MCF10A Aggregates with Defined Size and Cellular Composition for 3D Culture To build mosaic 3D epithelial microtissues with defined composition, a programmed assembly strategy was applied. The broad applicability of programmed assembly was confirmed by combining populations of epithelial cells expressing different fluorescent proteins into controlled aggregates for 3D culture (FIG. 22, Panel A).

Figure 23:
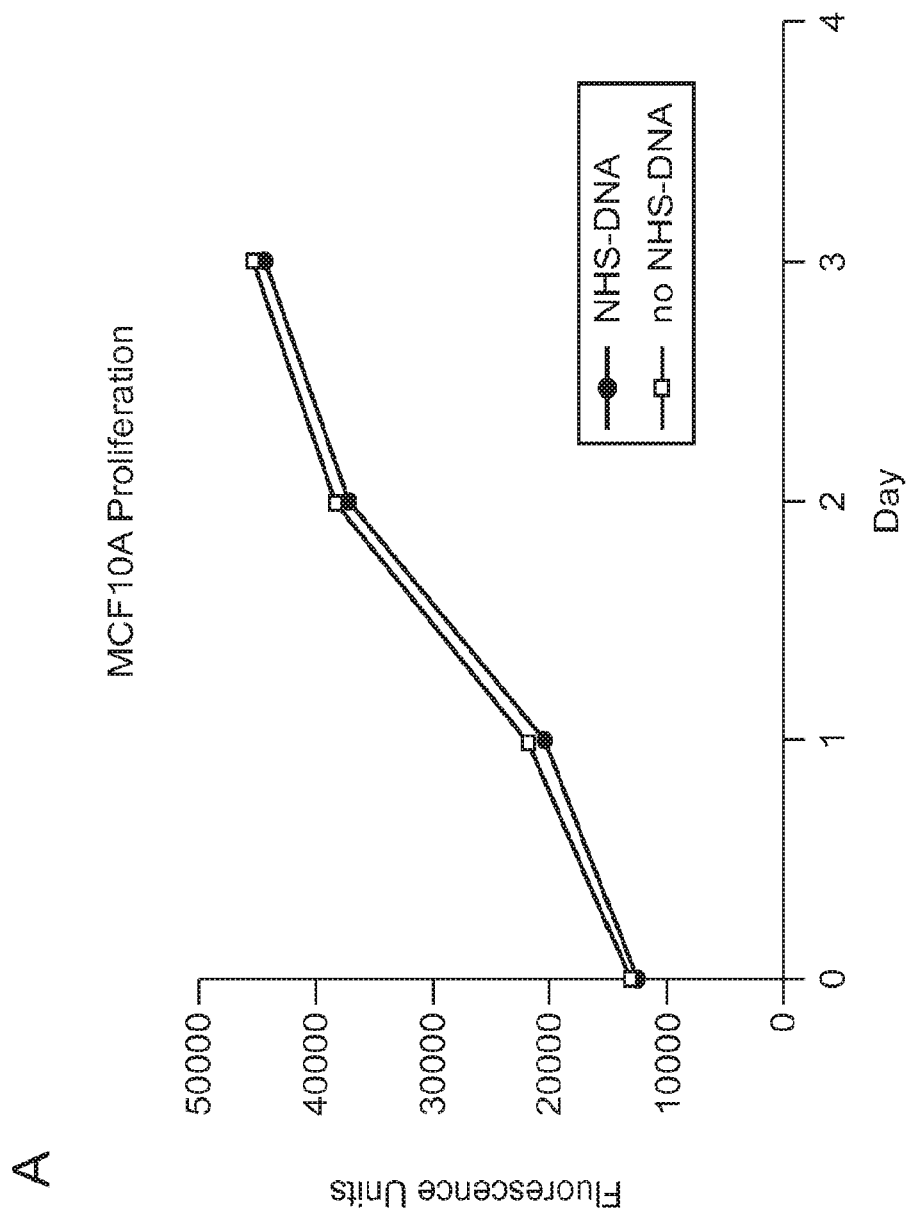
Figure 23:
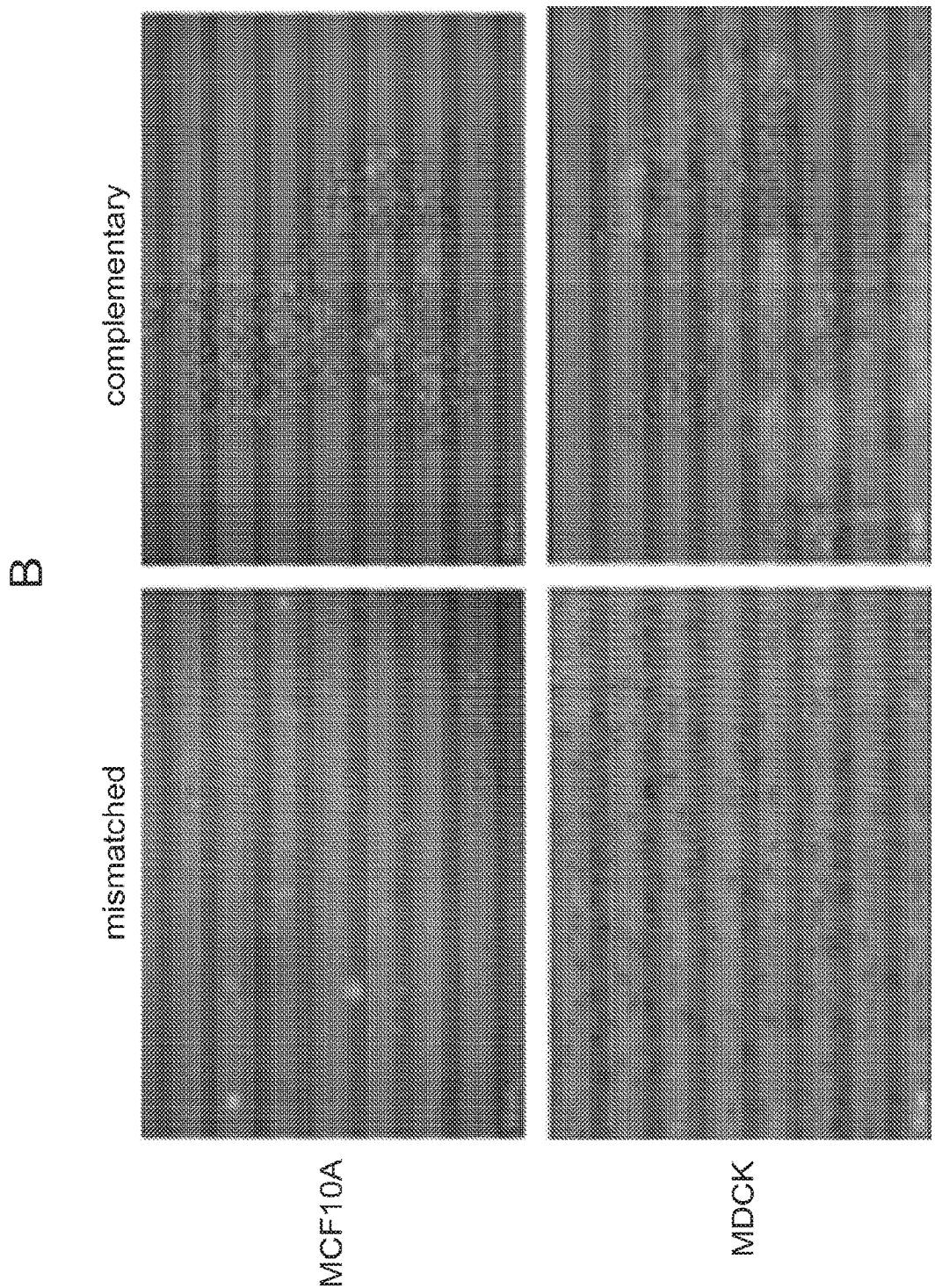
Figure 23:
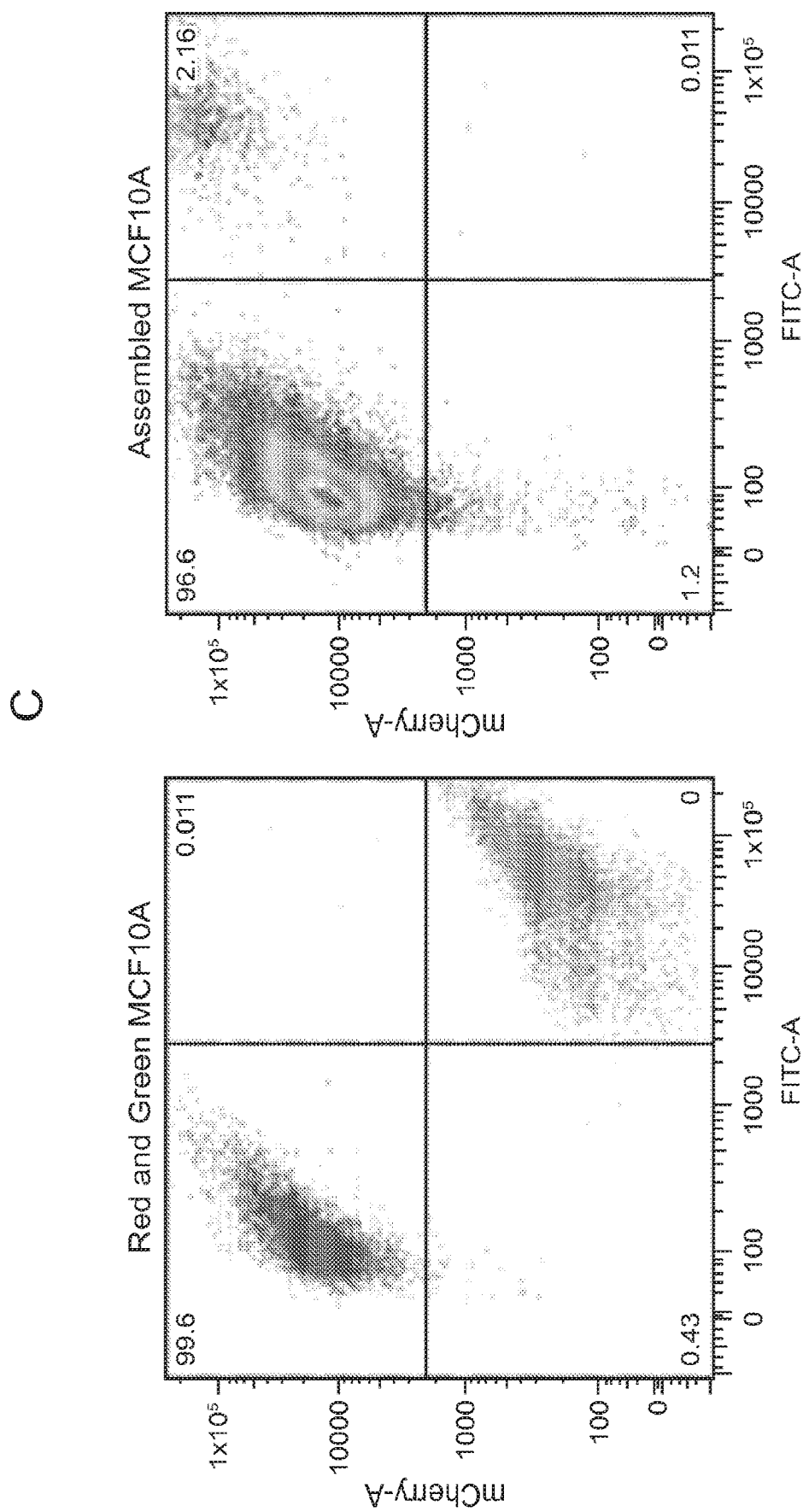
Figure 23:
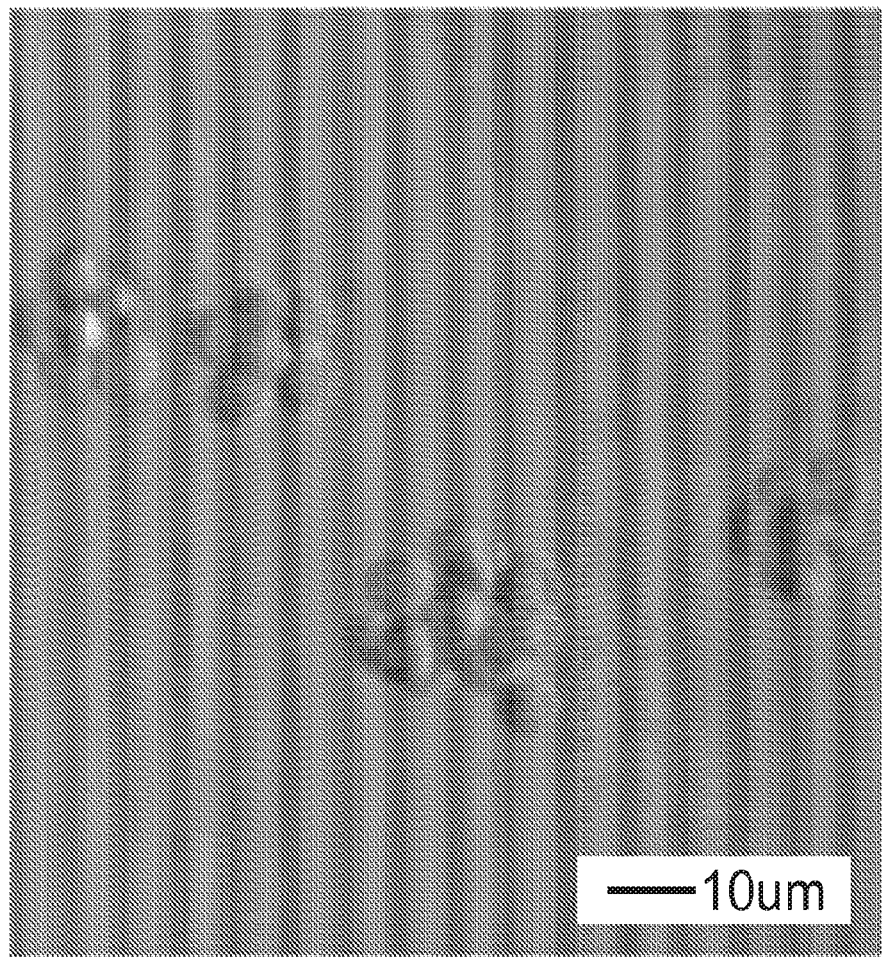
Figure 23:
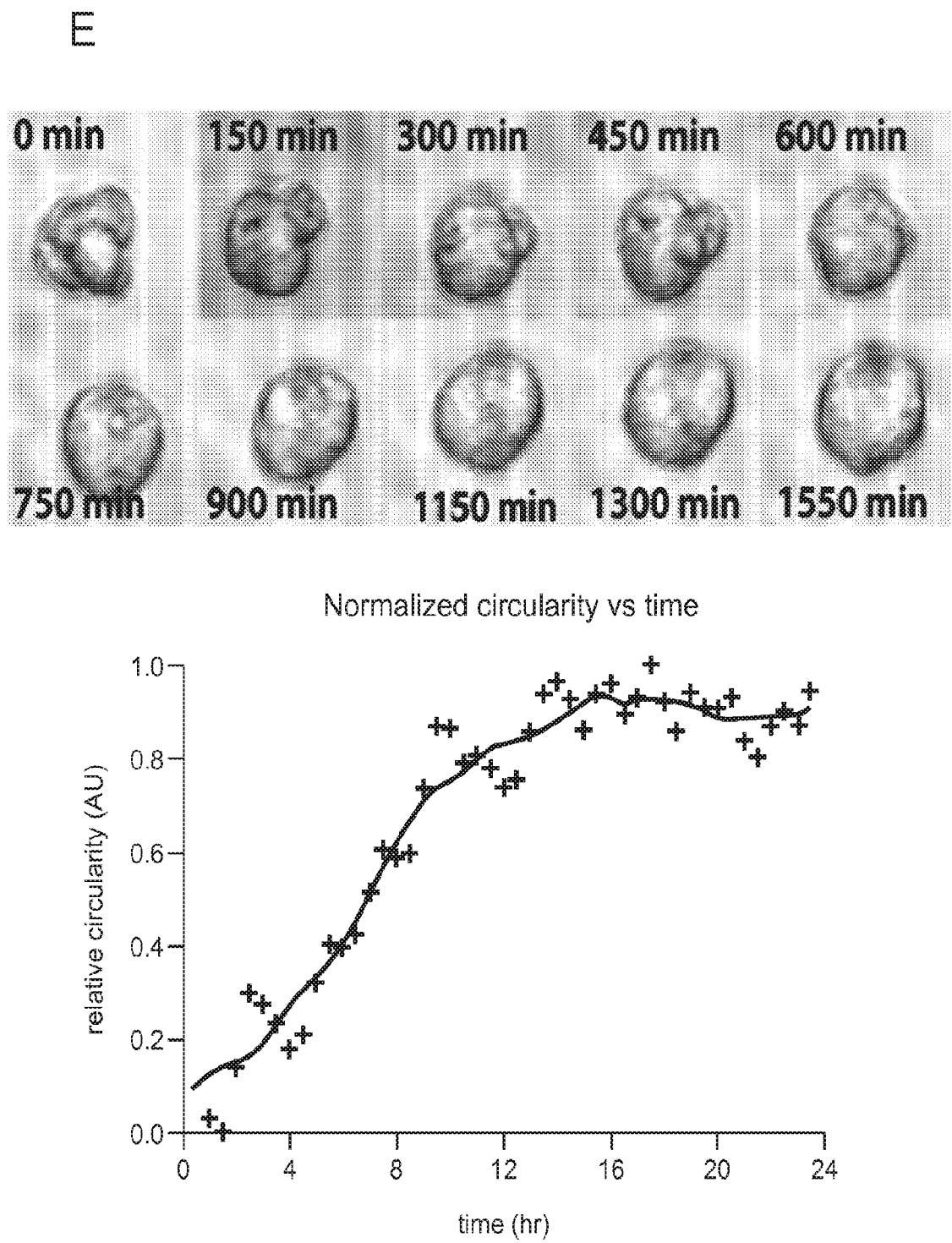

For the programmed assembly of cell aggregates mosaic for fluorescent protein expression, MCF10A cells expressing H2B-RFP or H2B-GFP were first prepared as single-cell suspensions by treatment of monolayer cultures with EDTA followed by a brief pulse with low-concentration trypsin. A fraction of MCF10A cell surface lysines were then chemically modified with 20-base oligonucleotides bearing a reactive NHS-ester functionality at their 5'ends (FIG. 22, Panel A). These DNA-conjugated cells were imparted with selective adhesive properties, yet retained the same viability and proliferative capacity as unmodified cells (FIG. 23, Panel A). Programmed assembly was initiated by mixing populations of green- and red-fluorescent MCF10A cells bearing complementary strands on their cell surfaces at a 1:50 ratio to prevent the red cells from reacting with more than one green cell. Fluorescence microscopy of the crude assembly reaction revealed a population of uniform cell aggregates composed of a single green cell surrounded by four to six red cells in addition to excess unassembled red cells (FIG. 22, Panel B). No aggregation was observed upon mixing of unlabeled cells or cells labeled with mismatched DNA strands (FIG. 23, Panel B). The Madin-Darby canine kidney (MDCK) epithelial cell line could similarly be assembled when labeled with lipid-modified oligonucleotides (FIG. 23, Panel B).

To quantify the efficiency of the self-assembly process, aggregates were analyzed by flow cytometry. Greater than 95% of the green cells assembled with red cells when bearing matched cell surface oligonucleotides, compared with only 5% in unlabeled or mismatched DNA-labeled cells (FIG. 23, Panel C). Fluorescence-activated cell sorting (FACS) was used to remove excess red cells and prepare enriched populations of mosaic MCF10A and MDCK aggregates for 3D culture (FIG. 22, Panel C and FIG. 23, Panel D). A total of 5,000-10,000 aggregates were routinely sorted directly onto lrECM-coated chamber slides where they rapidly condensed into spherical 3D microtissues with phase-dense boundaries over 6-12 hr (FIG. 22, Panel D and FIG. 23, Panel E). Time-lapse imaging of fluorescently labeled cell nuclei during this process revealed a transition from a disordered aggregate to a spherical microtissue with symmetrically arranged nuclei over a similar time frame (FIG. 22, Panel E). Morphogenesis of microtissues formed by the programmed assembly process involved considerable cell motility. These cell movements also became more concerted and continued at later time points (FIG. 22, Panel E).

Figure 24:
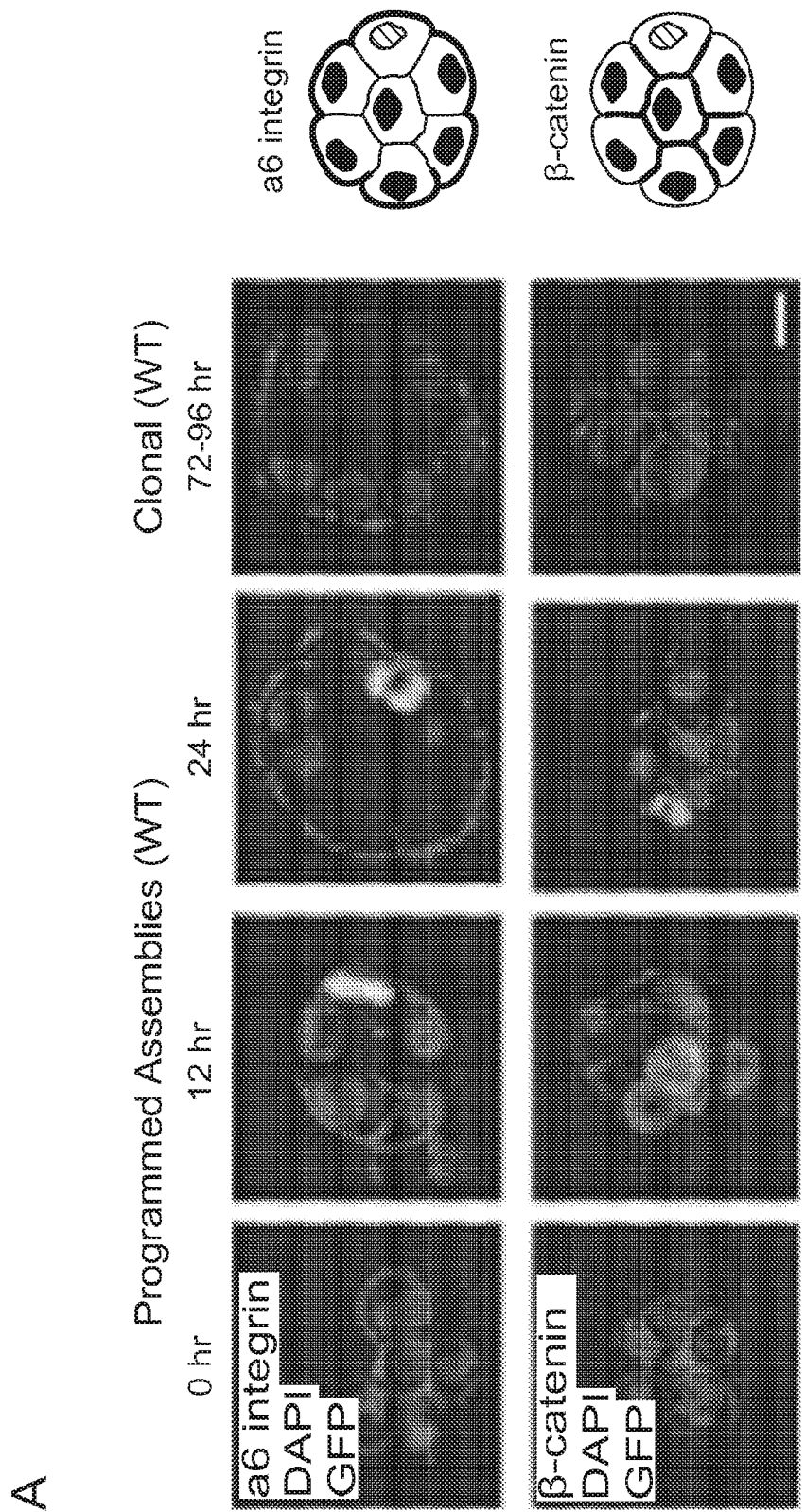
FIG. 24, Panels A-F depict onset of polarity, growth arrest, and lumen formation in MCF10A cell aggregates. Panel A: Representative confocal immunofluorescence images of MCF10A aggregates stained for α6-integrin and β-catenin after 0, 12, and 24 hr in 3D culture, and representative immunofluorescence images of similarly sized microtissues grown from single cells for comparison. A schematic illustrating the correct localization of α6-integrin and β-catenin for MCF10A microtissues undergoing morphogenesis is shown to the right. Panel B: Quantification of the onset of polarity in assembled aggregates of MCF10AWT cells. Values are means with error bars representing the SDs of the mean of 60 observations from at least two independent replicates. Panel C: Representative confocal immunofluorescence images of assembled MCF10A aggregates indicating correct localization of basement membrane component laminin-5 and cytoskeletal component F-actin after 24 hr in 3D culture. Panel D: Representative confocal immunofluorescence images of assembled MCF10A aggregates stained for cleaved caspase-3 and Ki-67 after 1, 4, and 16 days in culture (left). Schematic of MCF10A microtissue proliferation, growth arrest, and lumen formation (right). Panel E: Quantification of growth arrest and apoptotic lumen formation in microtissues grown from MCF10A aggregates. Data are expressed as the mean, and error bars represent the SD of the mean from at least two independent experiments (n=60). Panel F: MDCK aggregates and similarly sized cysts grown from single cells stained for basolateral marker β-catenin and apical marker gp135 after 6 or 7 days. Scale bars, 10 μm.
Figure 24:
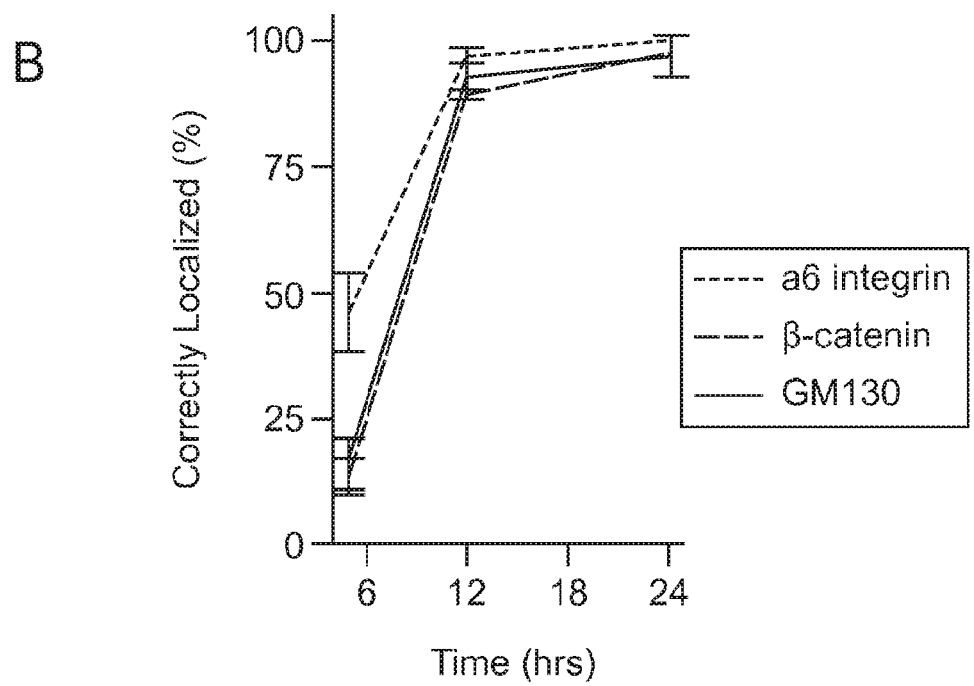
Figure 24:
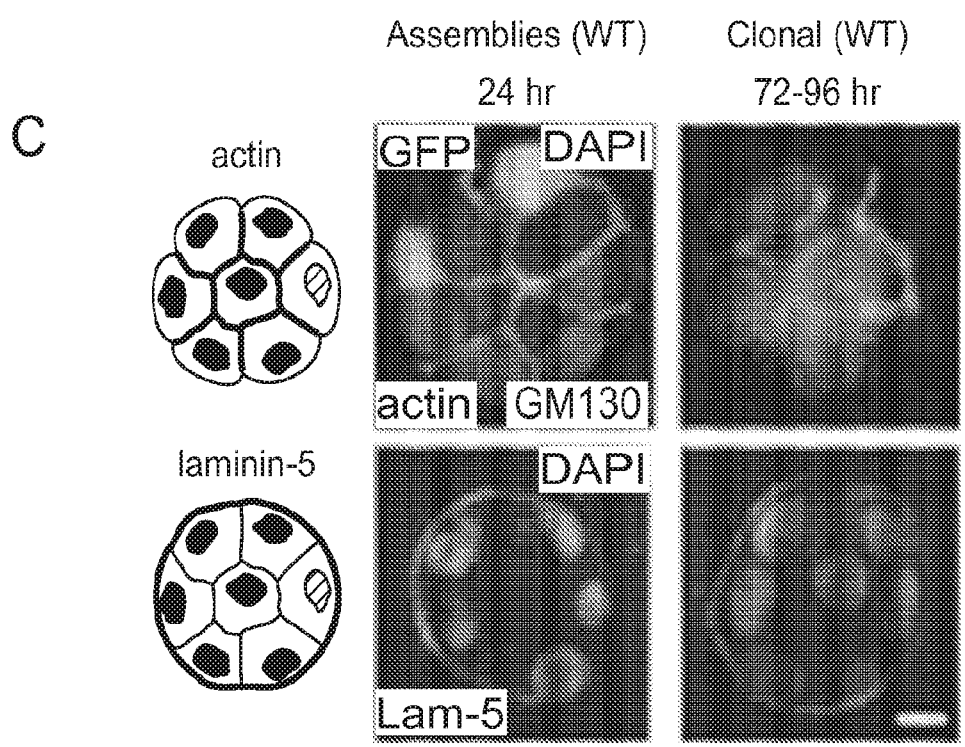
Figure 24:
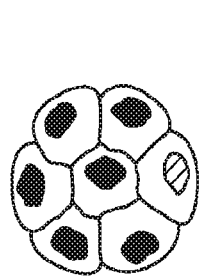
Figure 24:
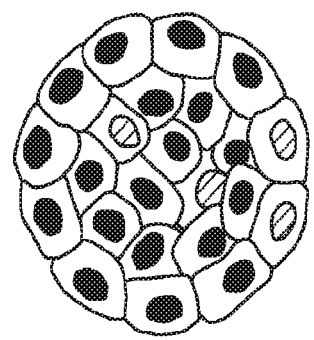
Figure 24:
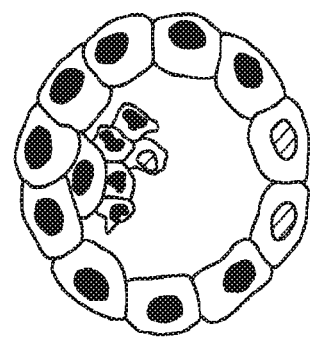
Figure 24:
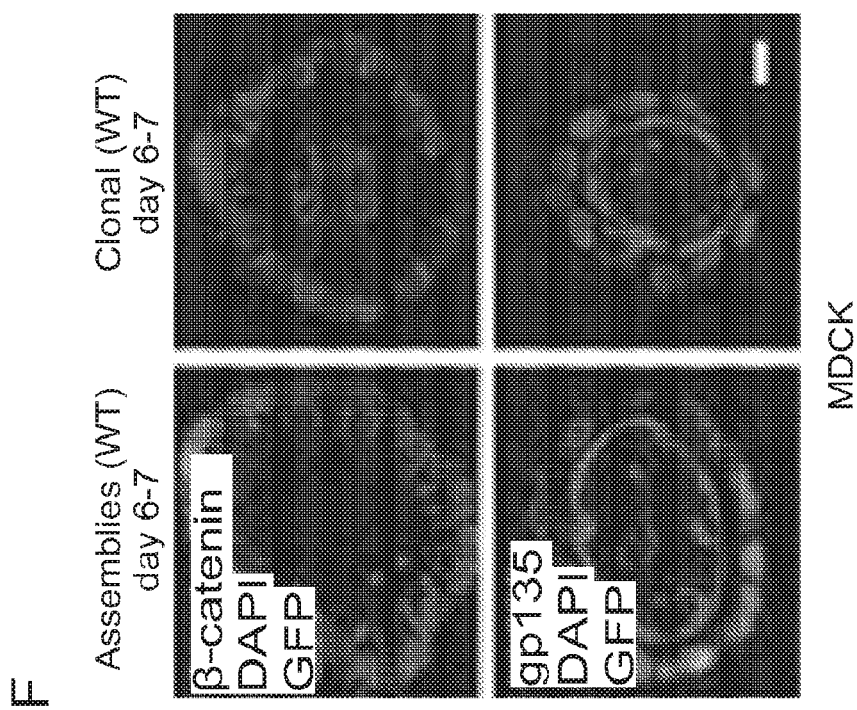
Figure 24:
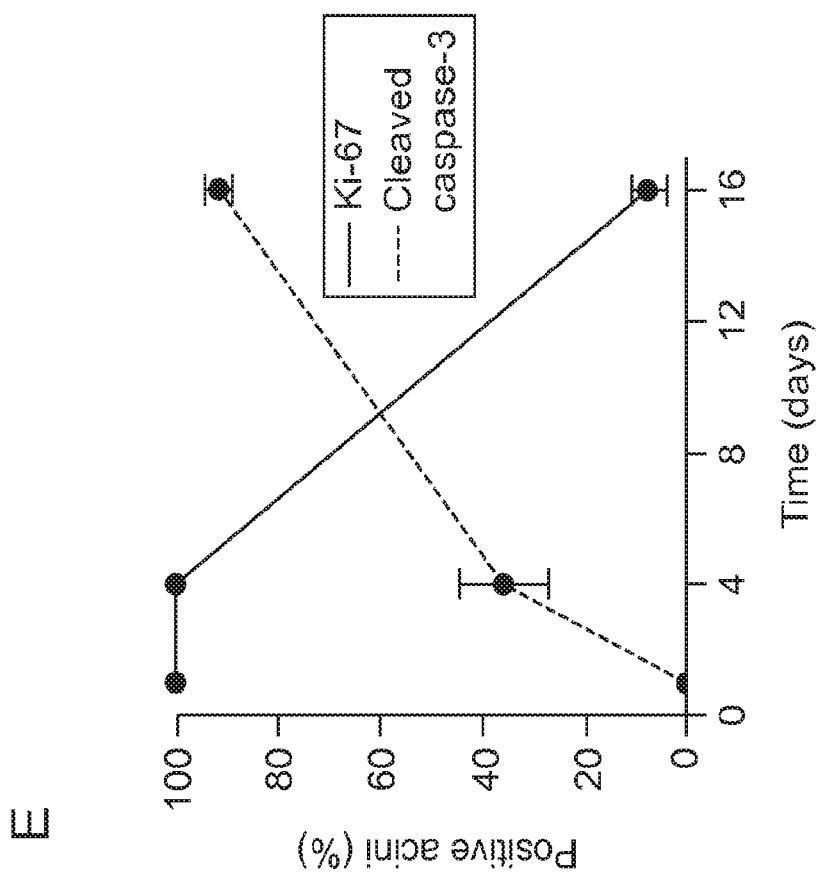
Figure 25:
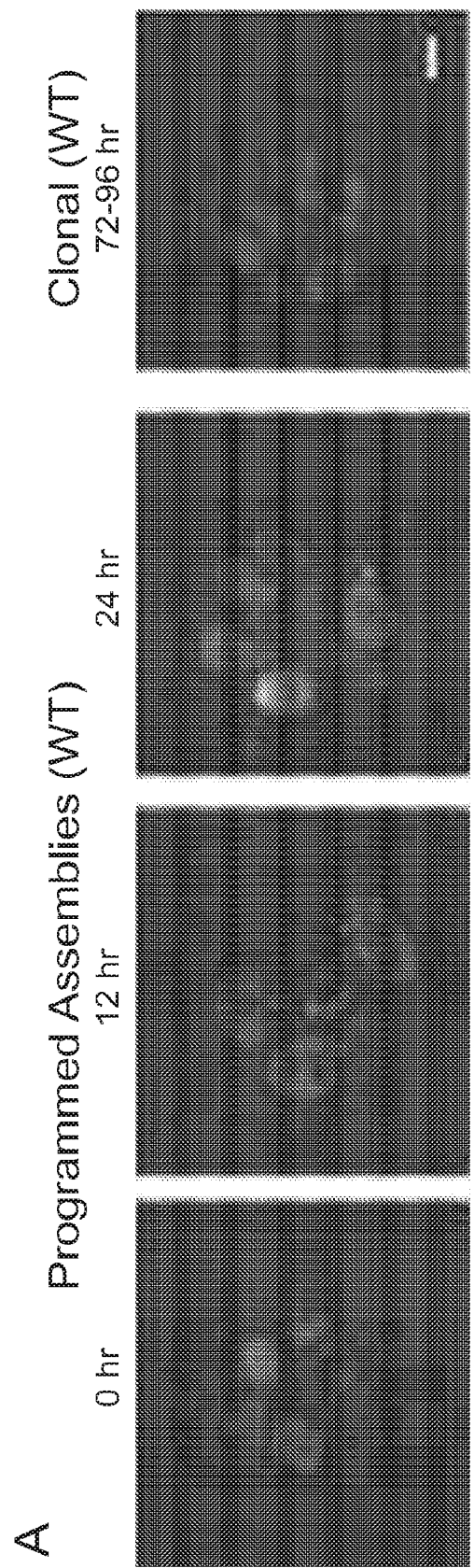
FIG. 25, Panels A-G depict polarity of homogeneous microtissues. Panel A: Representative confocal immunofluorescence images of MCF10AWT aggregates stained for GM130 (red) after 0, 12, and 24 hr in 3D culture, and representative immunofluorescence image of similarly sized microtissues grown from single cells for comparison. Panel B: Representative confocal immunofluorescence images of MCF10AWT aggregates stained for polarity markers after 8 days in 3D culture. Panel C: Representative confocal immunofluorescence images of MCF10AWT aggregates stained for polarity markers after 16+days in 3D culture. Panel D: Western blots for expression of Ras, phospho-Erk and E-cadherin for MCF10A cells transduced with pBabe-puro H-RasV12. Note that some samples for MCF10A and MCF10ARas are the same as from FIG. 26, Panels A-D. Panel E: Representative confocal immunofluorescence images of a MCF10ARas aggregate stained for basement membrane component laminin-5 after 24 hr in 3D culture. Panel F: Representative confocal immunofluorescence images of MCF10ARas aggregates stained for polarity markers after 16+days in 3D culture. Panel G: Quantification of phenotypes in MCF10A pBahe-puro H-RasV 12/MCF10AWT aggregates. Data are mean values of 3 replicate experiments, with error bars showing standard deviation of the mean. Scale bar=10 μm.
Figure 25:
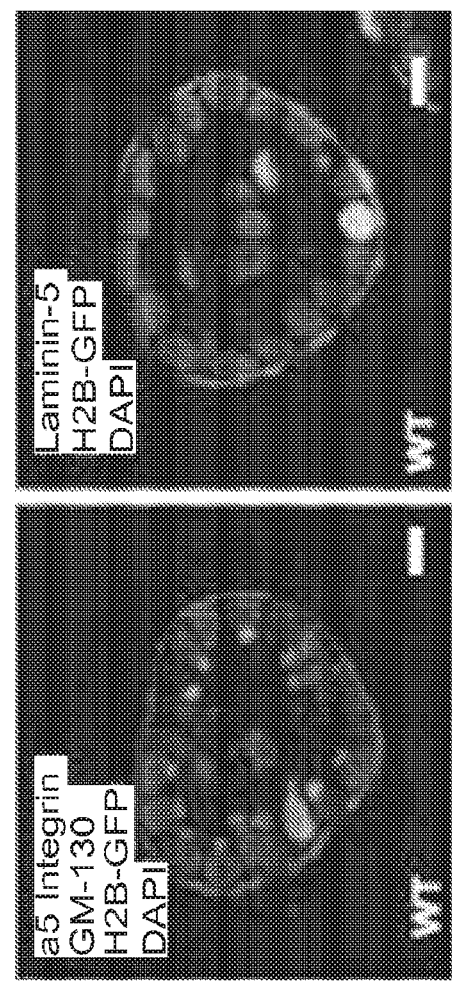
Figure 25:
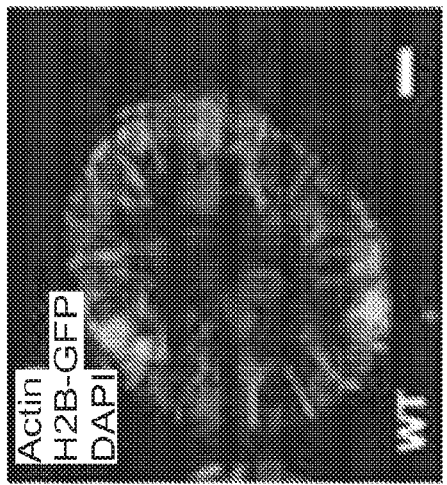
Figure 25:
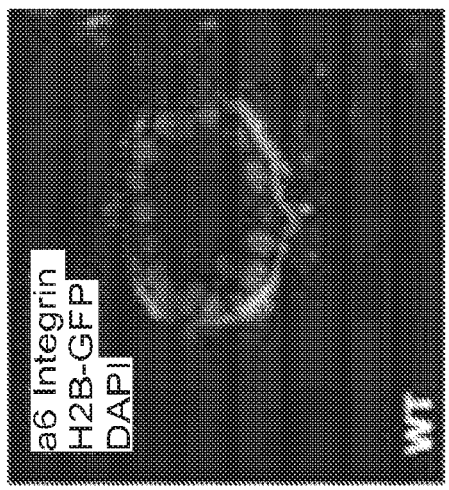
Figure 25:
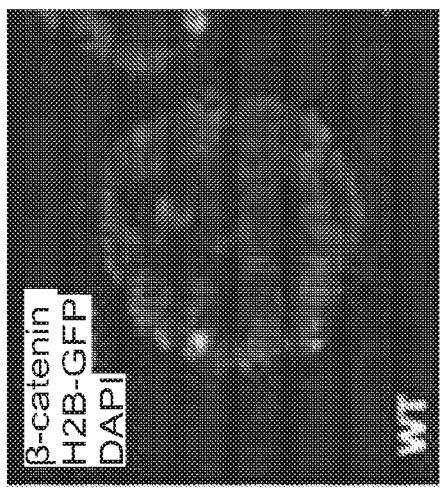
Figure 25:
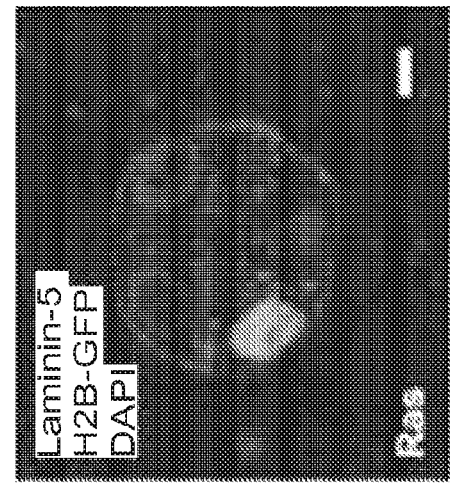
Figure 25:
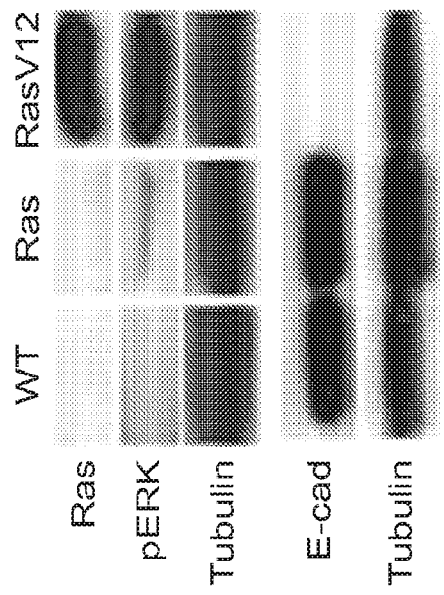
Figure 25:
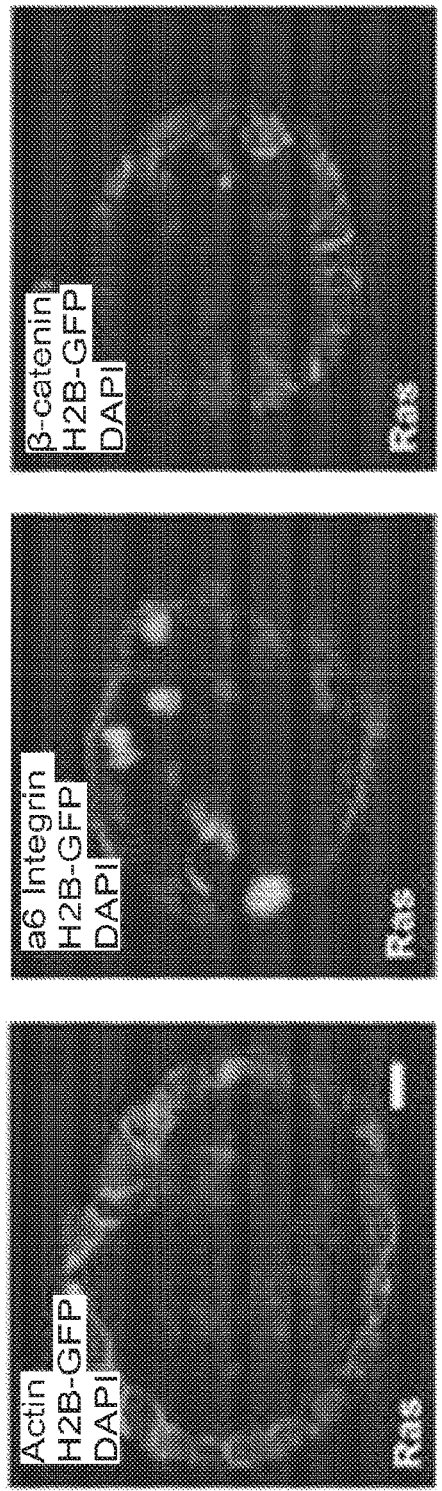
Figure 25:
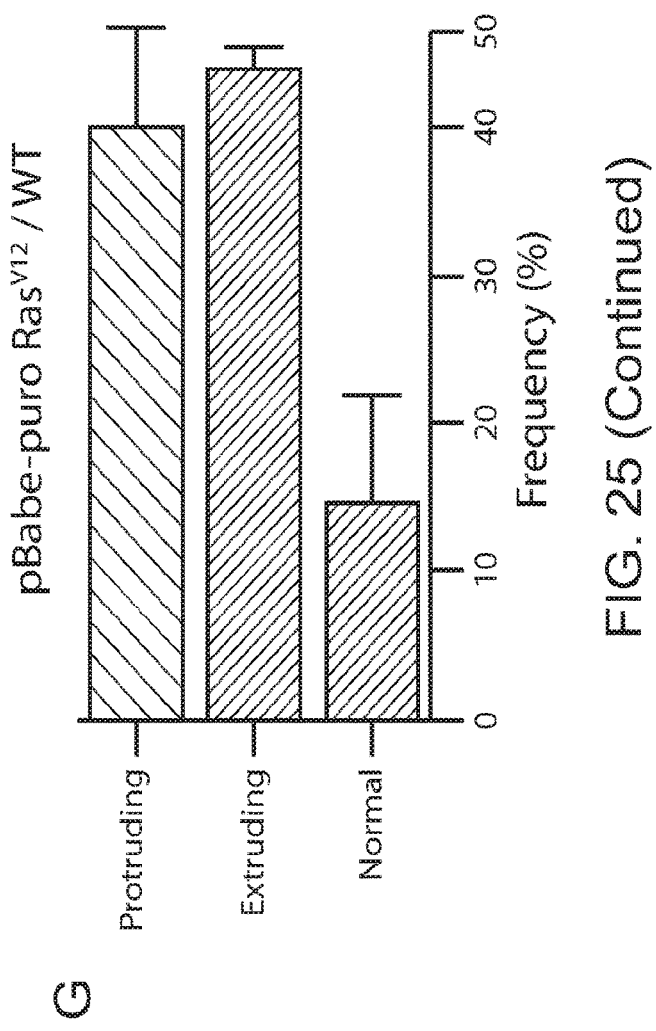

Example 11: Acquisition of Microtissue Polarity in Chemically Assembled MCF10A Cells Occurs within 12 Hr in 3D Culture The observation that multicellular aggregates are motile and rapidly condense suggested that the cells were polarizing and replacing their DNA-based chemical adhesions with native-like, protein-based adhesions. To determine whether aggregates were indeed polarizing during the first 24hr in culture, indirect immunofluorescent staining for protein localization was performed at regular intervals after programmed assembly and purification by FACS. Immediately after sorting of MCF10A aggregates, hemidesmosomal adhesion molecule α6-integrin and adherens junction protein β-catenin were localized to individual cell edges, whereas cis-Golgi protein GM130 was randomly oriented relative to cell nuclei (FIG. 24, Panel A and FIG. 25, Panel A). These results indicate that cells remained distinct entities immediately after programmed assembly despite their DNA-based chemical adhesions. By 12 hr after assembly these markers for cell polarity were enriched at appropriate subcellular locations (FIG. 24, Panels A-B). By 24 hr, protein localization was pronounced; β-catenin was enriched at cell-cell interfaces, α6-integrin was enriched at the basolateral surface of the microtissue, and GM130 was apically localized relative to cell nuclei (FIG. 24, Panels A-B, and FIG. 25, Panel A). Additional staining of microtissues 24 hr after assembly revealed basal deposition of laminin-5 and actin enrichment at the cell cortex (FIG. 24, Panel C). These staining patterns indicate that cell aggregates rapidly condense into polarized microtissues (FIG. 24, Panel A and FIG. 25, Panel A). Polarity was also maintained at later time points (FIG. 25, Panels B-C).

Up to 96 hr after assembly, the majority of assembled microtissues were uniformly positive for the proliferation marker Ki-67 (FIG. 24, Panels D-E). However, microtissues were largely negative for Ki-67 at later time points. Moreover, cells positive for cleaved caspase-3 in the clearing luminal space, which were largely absent at 24 hr, became evident as early as 96 hr and were present in nearly all acini by day 16 (FIG. 24, Panels D-E).

To test the applicability of this approach for generating other epithelial microtissues, the polarity and lumenogenesis of MDCK aggregates in 3D culture after programmed assembly was evaluated. MDCK cells undergo lumenogenesis by a different mechanism than MCF10A cells, providing an additional test for the compatibility of programmed assembly with diverse cellular processes during morphogenesis. MDCK aggregates grown for 6-7 days in lrECM were uniformly polarized as judged by staining for apical marker gp135 and β-catenin (FIG. 24, Panel F, left). Developing lumens were also observed. Additionally, the morphology of cysts was similar to the morphology of cysts of equivalent size grown from single cells (FIG. 24, Panel F, right). Combined, these data indicate that the hallmarks of epithelial morphogenesis—polarity, growth arrest, and lumen formation—are recapitulated when epithelial cell aggregates prepared by programmed assembly are grown in 3D lrECM culture.

Example 12: MCF10ARAs Cells Undergo Morphogenesis Similar to MCF10AWT Cells

Figure 26:
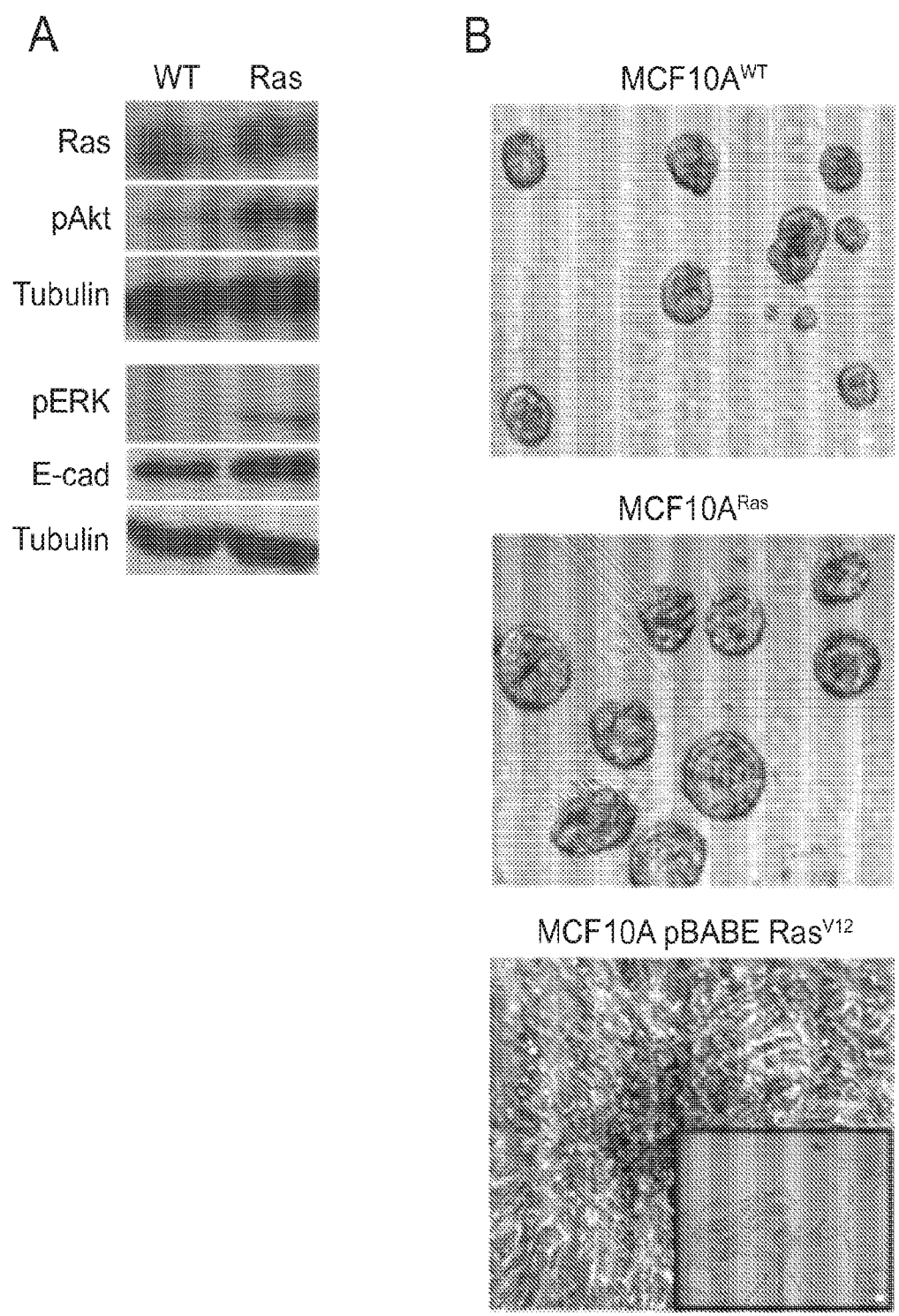
FIG. 26, Panels A-D show that assembled MCF10ARas cells undergo morphogenesis similar to MCF10A WT cells. Panel A: Western blots for Ras, phospho-Akt, phospho-Erk, and E-cadherin (E-cad) for MCF10AWT and MCF10ARas cells. Panel B: Phase-contrast images of MCF10AWT, MCF10ARas, and pBabe-puro RasV12-transduced MCF-10A cells cultured for 23 days in lrECM. Inset shows the pBabe-puro RasV12-transduced cells after 5 days of culture in lrECM. Panel C: Representative confocal immunofluorescence images of homogeneous MCF10ARas cell aggregates stained for polarity and adherens junction proteins after culture in lrECM for the indicated times. These images should be compared to representative immunofluorescence images of similarly sized microtissues grown from single cells (right) and MCF10AWT-staining patterns as shown in FIG. 24, Panel A and FIG. 25, Panel A. Panel D: Representative confocal immunofluorescent images of homogeneous MCF10ARas aggregates stained for cleaved caspase-3 and Ki-67 after 16 or more days in culture. Scale bars, 20 μm.
Figure 26:
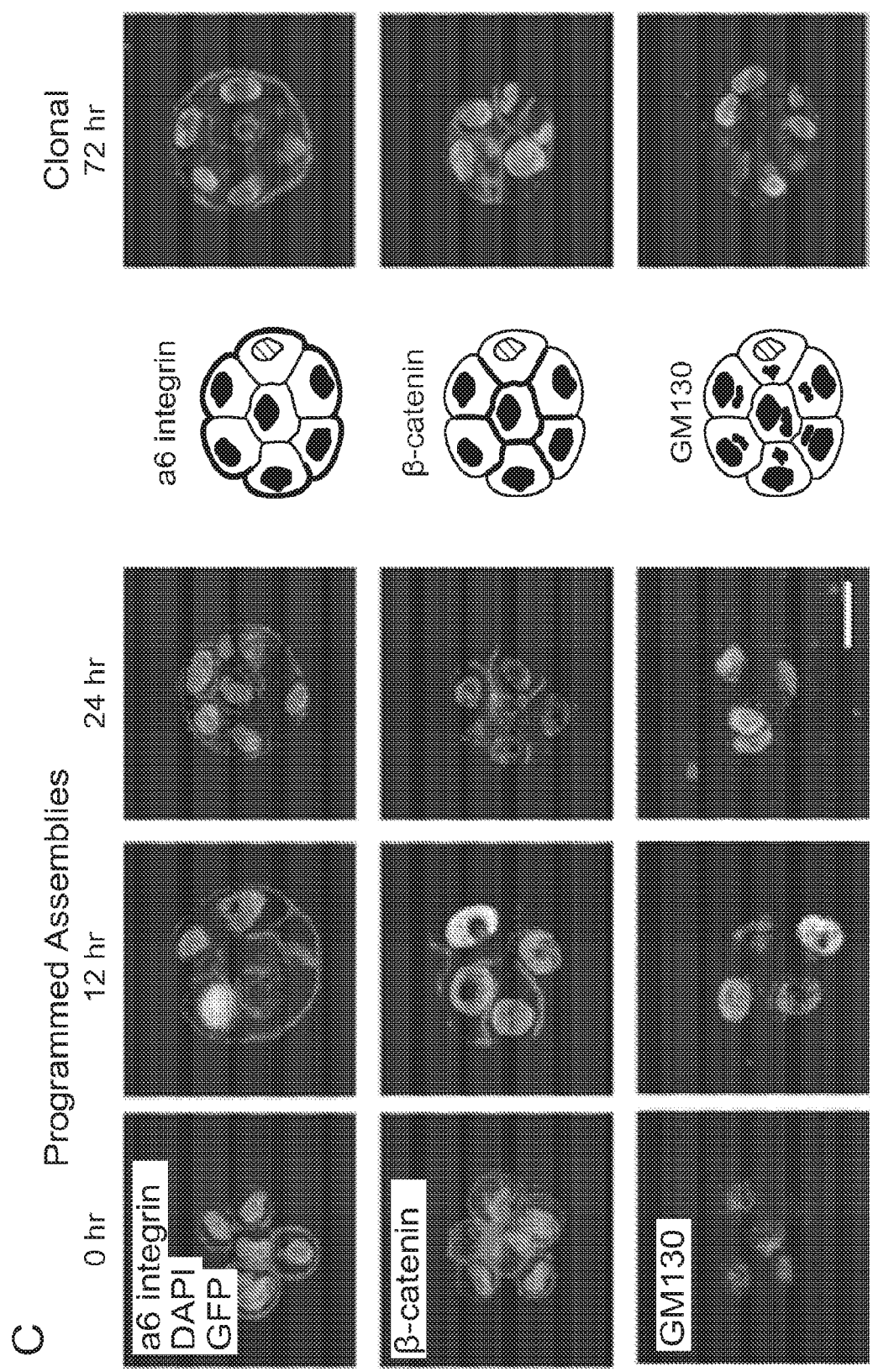
Figure 26:
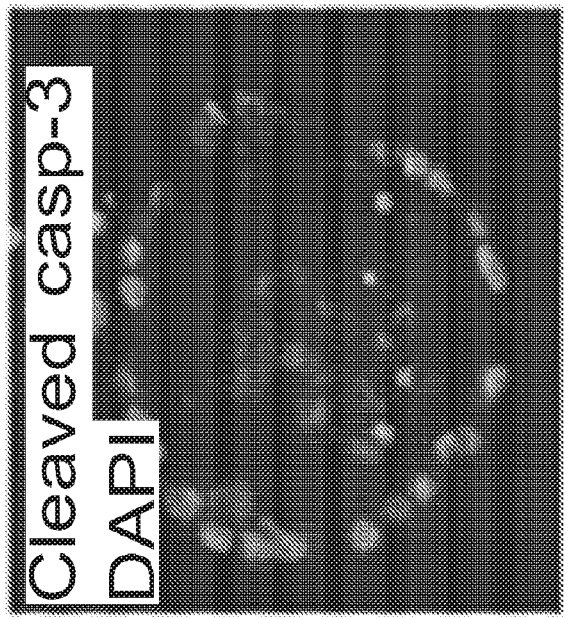
Figure 26:
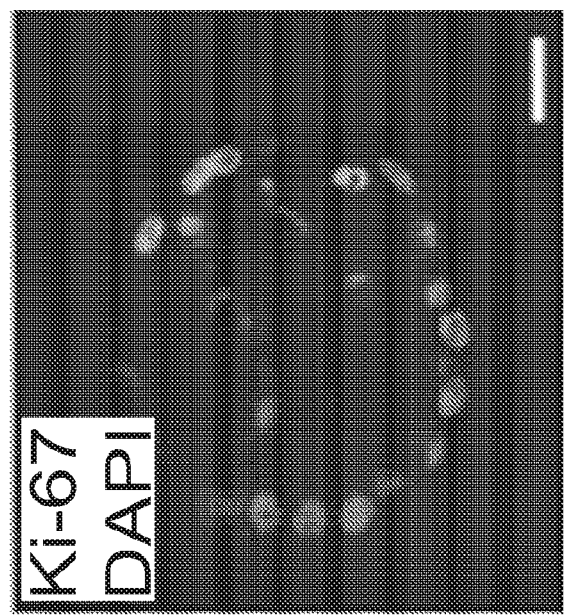

To understand how groups of cells undergoing morphogenesis respond to cell-to-cell variability in Ras activation within the same tissue, a MCF10A derivative cell with modestly elevated Ras activity but also with basic epithelial character and the ability to interact with neighboring WT cells was required. Ras pathway activation in an ideal MCF10A derivative should he elevated but consistent with levels observed in normal tissues. However, cells expressing H-RasV12 under the control of the strong Moloney murine leukemia virus LTR were found to have very high levels of Ras expression and Erk phosphorylation, lost E-cadherin expression and their epithelial morphology after a few passages, and formed highly invasive and disorganized structures in 3D culture (FIG. 25, Panel D, and FIG. 26, Panel B). Therefore, MCF10A cells overexpressing H-RasV 12 were a poor choice for modeling heterogeneous Ras activation during normal physiological processes.

In contrast the MCF-10AneoT cell line (referred to here as MCF10ARas for clarity) retained its epithelial characteristics despite chronic H-Ras activation. These cells were generated by stable transfection with a mutant Ras gene encoding the constitutively active H-RasV12 protein. Unlike acutely transduced cells, however, MCF10ARas cells were previously shown to express only a modest 4-fold increase in H-Ras and a 3- to 6-fold increase in phospho-Alt relative to MCF10AWT. These results were confirmed and a modest increase in phospho-Erk was observed (FIG. 26, Panel A). Additionally, MCF10ARas cells were found to express nearly WT levels of E-cadherin (FIG. 26, Panel A). Consistent with their modestly elevated H-Ras activity, MCF10ARas cells formed acini that were larger in size than MCF10AWT acini but still lumenized when grown from single cells for 23 days in 3D culture (FIG. 26, Panel B). Similar to MCF10AWT aggregates, assembled aggregates of MCF10ARas cells condensed into polarized microtissues over 24 hr (FIG. 25, Panel E and FIG. 26, Panel C). After 16 days in 3D culture, they formed acini that were largely negative for Ki-67 but contained cells positive for cleaved caspase-3 in the lumen (FIG. 25, Panel F and FIG. 26, Panel D). MCF10ARas cells were therefore used for building heterogeneous microtissues in subsequent experiments because they remained epithelial in character and displayed levels of Ras pathway activation consistent normal tissues.

Figure 27:
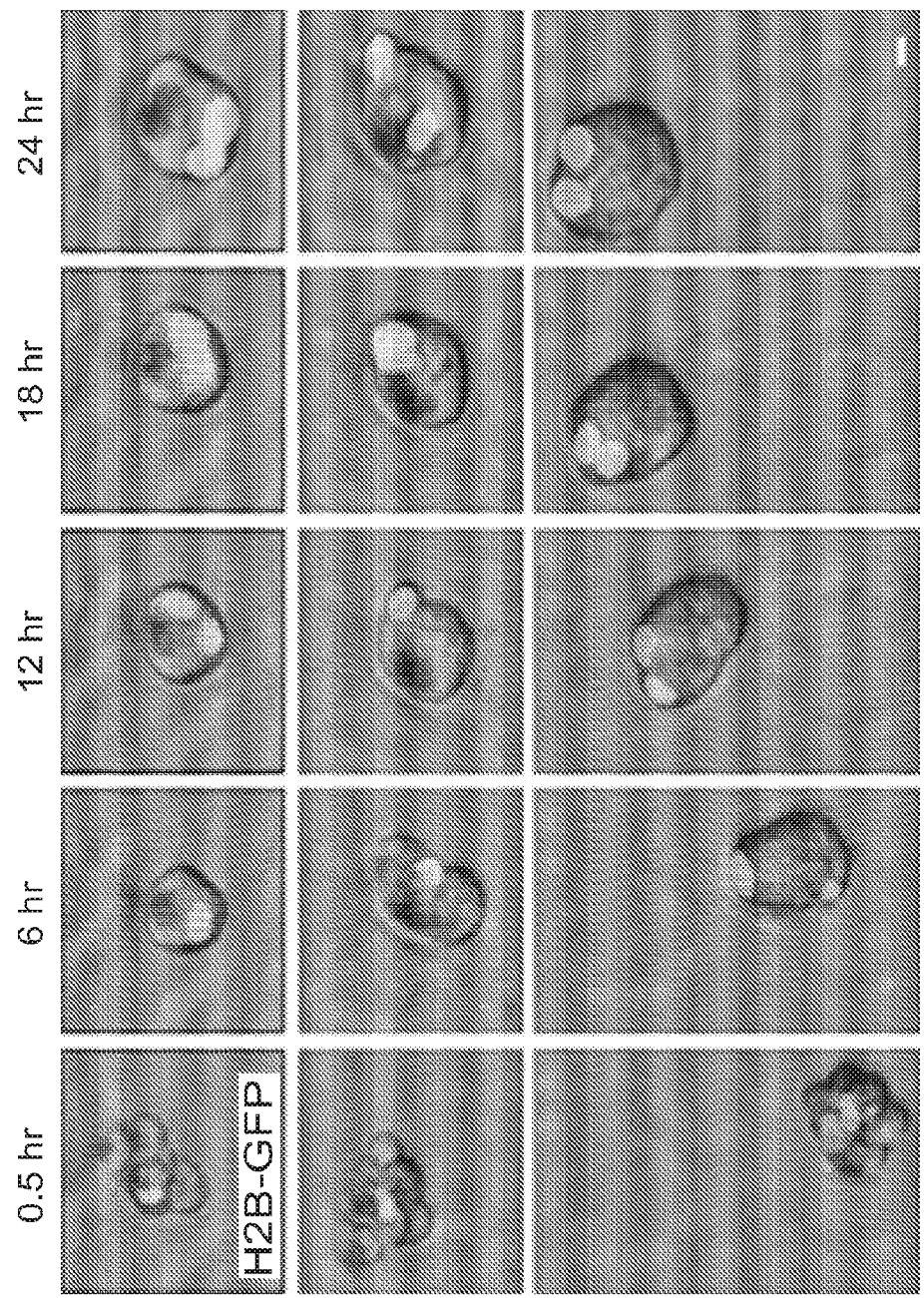
FIG. 27, Panels A-E show emergent behaviors in rnicrotissues heterogeneous for signaling downstream of H-Ras.
Figure 27:
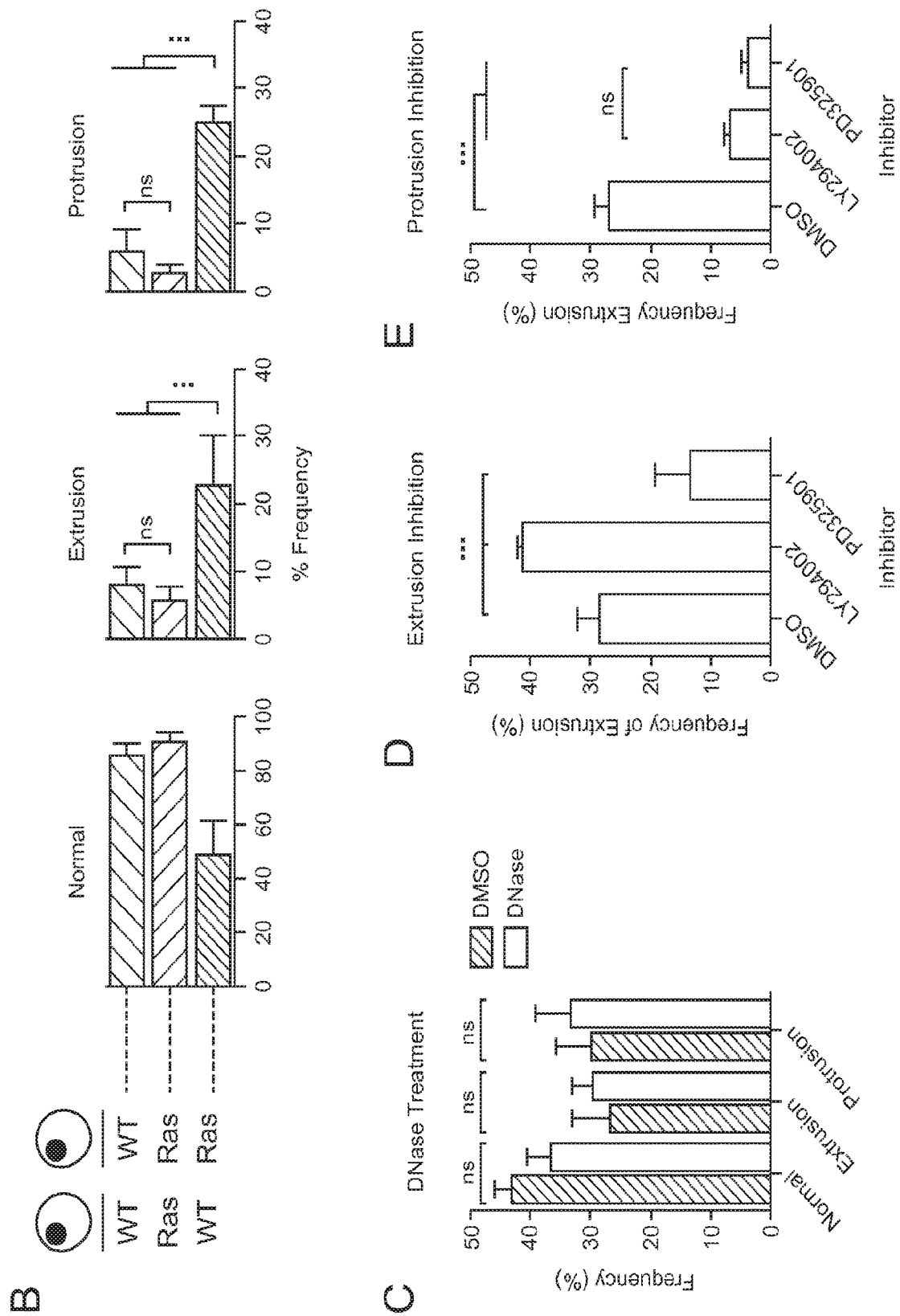

Example 13: Single MCF10ARas Cells Lead Motile Multicellular Protrusions or Basally Extrude from WT Microtissues Using programmed assembly, mosaic aggregates comprising a single MCF10ARas cell surrounded by WT cells were prepared. Although homogeneous aggregates of MCF10ARas cells were phenotypically similar to WT aggregates with respect to polarity and morphology over 24 hr, emergent phenotypes in heterogeneous microtissues were unexpectedly observed. In some cases, multicellular protrusions tipped by a single, motile MCF10ARas cell seemed to direct the motion of the surrounding WT microtissue across the lrECM over several hours (FIG. 27, Panel A). Multicellular protrusions occurred in 20%-30% of the mosaic microtissues.

In an additional 20%-30% of mosaic aggregates, cell extrusion was observed where the single MCF10ARas cell exited at the basal surface but remained loosely associated with the microtissue. Significantly, the multicellular protrusion and basal extrusion phenotypes were rarely observed for single MCF10ARas cells grown within homogeneous MCF10ARas microtissues (FIG. 27, Panel B). These behaviors were not due to adaptation to chronic Ras activation, as they were also observed in heterogeneous assemblies made with single MCF10A cells acutely expressing H-RasV12 (FIG. 25, Panel G). Additionally, in 4%-6% of the mosaic aggregates, the MCF10ARas cell was highly motile and broke away from the surrounding WT microtissue, occasionally traversing over 100 μm (FIG. 28, Panels A-B). Addition of high-activity DNase to the media immediately after sorting did not affect the frequency of extrusion and protrusions, indicating that DNA-based linkages between cells were not responsible for the observed phenotypes (FIG. 27, Panel C).

Further characterization of heterogeneous microtissues revealed that both protruding and extruded cells were viable as judged by exclusion of a cell-impermeant DNA stain (FIG. 28, Panel C). Protruding cells were often irregularly shaped with GM130 staining oriented away from the microtissue center (FIG. 28, Panels D and E) but with strong staining for β-catenin at cell-cell adhesions with neighboring WT cells (FIG. 28, Panel F). Basally extruded cells typically maintained a rounded morphology. An actin ring was not observed in adjacent cells or any unusual actin staining in extruded cells (FIG. 28, Panel D). However, once fully extruded, cells did not exhibit β-catenin staining on membranes adjacent to the WT microtissue (FIG. 28, Panel F). Because MCF10AWT and MCF10ARas cells expressed similar levels of E-cadherin (FIG. 27, Panel A) and were frequently observed to freely commingle, these behaviors could not be explained by differential E-cadherin expression alone. Moreover, heterogeneity, per se, was not responsible for the extrusion or multicellular protrusion phenotypes because single WT cells did not protrude or extrude from aggregates composed principally of MCF10ARas cells.

Ras activates multiple pathways in its GTP-bound form. PI3K and the MAPK signaling cascades have recently been implicated as important downstream effectors of analogous protrusive membrane activity and apical cell extrusions, respectively, during H-RasV12 overexpression in confluent 2D MDCK monolayers and model organisms. To determine whether these pathways were also necessary for basal cell extrusion and motile multicellular protrusions during heterogeneous MCF10A aggregate morphogenesis in lrECM, freshly assembled mosaic aggregates were treated with small-molecule inhibitors and the distribution of resulting phenotypes was quantified over 24 hr in culture. Treatment with PI3K inhibitor LY294002 or PIK-90 reduced the formation of multicellular protrusions while slightly increasing the frequency of basal extrusions compared to treatment with DMSO control (FIG. 27, Panels D-E, and FIG. 28, Panels G-H). In contrast, treatment of mosaic aggregates with the MEK inhibitor PD325901 or the Raf inhibitor Sorafenib blocked both multicellular protrusions and basal extrusions. The morphology of aggregates treated with inhibitors was indistinguishable from those treated with DMSO vehicle control (FIG. 28, Panels I-J). Therefore, MEK activation was required for basal extrusions, whereas both PI3K and MAPK signaling pathways were necessary for motile multicellular protrusions.

Example 14: Motility of MCF10Ras Cells in Homogeneous and Heterogeneous Microtissues is Quantitatively Different To further characterize the emergent behaviors resulting from cell-to-cell variability in Ras activity, the positions of individual MCF10AWT or MCF10ARas cells were tracked in microtissues over 24 hr. MCF10AWT and MCP10ARas cells did not differ significantly in maximum displacement from their initial positions when grown within homogeneous microtissues containing only cells of the same type (FIG. 29, Panels A-B). This is consistent with the qualitative observation that homogeneous microtissues have a normal morphology over this time period. In contrast the maximum displacement of single MCF10ARas cells in heterogeneous aggregates with surrounding WT cells was increased relative to the same cells in homogeneous MCF10ARas aggregates (FIG. 29, Panels A-B) without a significant increase in average speed (FIG. 29, Panel C). The increase in mean displacement of MCF10ARas cells when grown among MCF10AWT cells was almost entirely attributable to microtissues with the multicellular protrusion phenotype (FIG. 29, Panel D); when MCF10ARas cell tracks were segregated into normal, extruding, and protruding phenotypes, average displacements (±95% CI) of 26 (±3), 31 (±5), and 61 (±9) μm were found, respectively. Although the displacement of MCF10ARas cells in normal and extruding microtissues typically remained within the average diameter of heterogeneous microtissues (43.7±8.47 μm), the displacement of protruding cells generally exceeded the size of microtissues, sometimes significantly.

To quantify the extent to which single, protruding MCF10ARas cells affected the motility of the surrounding WT microtissue, the trajectories of the MCF10ARas cells were compared to the trajectories of the surrounding microtissue. Overall, the trajectories for single MCF10ARas cells and their WT neighbors were correlated for all three phenotypes (FIG. 30). Interestingly, the large displacements observed for single MCF10ARas cells participating in motile multicellular protrusions were also observed for their associated WT microtissues (FIG. 29, Panel E), indicating that the single MCF10ARas cell directs the motion of the entire microtissue. Moreover, subtracting the coordinates of the microtissue centroid from the coordinates of the protruding MCF10ARas cell generated residual trajectories (FIG. 29, Panel E) that were qualitatively similar to those of single cells in homogeneous MCF10ARas and WT microtissues (FIG. 29, Panel A). This analysis occasionally revealed residual trajectories with large total displacements, which always corresponded to the rare, hypermotile cells (FIG. 29, Panel E, dashed track).

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims. It is also to he understood that the terminology used herein is for the purpose of describing particular embodiments only, and is not intended to be limiting, since the scope of the present invention will be limited only by the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A system comprising:
(i) a first isolated cell comprising a membrane anchored polynucleotide duplex, the duplex comprising:
a first compound comprising:
a membrane anchoring region comprising a long alkyl chain of at least 12 carbon atoms inserted into a lipid bilayer of the first isolated cell; and
a polynucleotide having a membrane distal end and a membrane proximal end, wherein the polynucleotide is at least 70 nucleotides and comprises:
(1) a linker region comprising a contiguous stretch of at least 60 nucleotides, and
(2) a membrane distal adhesion region comprising at least 10 nucleotides and positioned distal to the linker region, wherein the linker region is not hybridizable to the membrane distal adhesion region;
wherein the polynucleotide is conjugated to the membrane anchoring region at the membrane proximal end; and
a second compound comprising:
a membrane anchoring region comprising a long alkyl chain of at least 12 carbon atoms inserted into the lipid bilayer of the isolated cell and conjugated to a polynucleotide that is shorter than the polynucleotide of the first compound and comprises a contiguous stretch of at least 10 nucleotides that is hybridized to the polynucleotide of the first compound to a region outside of the membrane distal adhesion region; and
(ii) a second isolated cell comprising a third compound, the third compound comprising:
a membrane anchoring region comprising a long alkyl chain of at least 12 carbon atoms inserted into a lipid bilayer of the second isolated cell;
a polynucleotide having a membrane distal end and a membrane proximal end, wherein said polynucleotide is at least 70 nucleotides and comprises:
(1) a linker region comprising a contiguous stretch of at least 60 nucleotides, and
(2) a membrane distal adhesion region comprising at least 10 nucleotides and positioned distal to the linker region, wherein the linker region is not hybridizable to the membrane distal adhesion region;

wherein the polynucleotide of the third compound is conjugated to the membrane anchoring region at the membrane proximal end of the third compound;
wherein the membrane distal adhesion region of the first compound and the membrane distal adhesion region of the third compound are hybridizable such that hybridization of the membrane distal adhesion region of the first compound and the membrane distal adhesion region of the third compound results in assembly of the first cell and the second cell with each other.

2. The system of claim 1, wherein the polynucleotide of the first compound is a DNA polynucleotide, and the membrane proximal end is a 5' end of the polynucleotide.

3. The system of claim 1, wherein the membrane anchoring region of the first and second compounds of the composition comprises a monoalkyl chain comprising 16 to 18 carbon atoms.

4. The system of claim 3, wherein the membrane anchoring region of the first and second compounds of the composition comprises a monoalkylamide.

5. The system of claim 1, wherein the membrane anchoring region of the first and second compounds comprises a dialkylphosphoglyceride.

6. The system of claim 5, wherein the dialkylphosphoglyceride is a $C_{16}$dialkylphosphoglyceride.

7. The system of claim 6, wherein the membrane distal adhesion region of the first compound comprises $(CAGT)_5$ or $(ACTG)_5$.

8. The system of claim 7, wherein the polynucleotide of the first compound comprises 80 to 100 nucleotides.

9. The system of claim 8, wherein the linker region of the first compound comprises a contiguous stretch of at least 60 thymine or adenine nucleotides.

10. The system of claim 1, wherein the linker region of the first and third compounds comprises 60 to 200 nucleotides.

11. The system of claim 1, wherein the linker region of the first and third compounds comprises 60 to 100 nucleotides.

12. The system of claim 1, wherein the linker region of the first and third compounds comprises 60 to 80 nucleotides.

13. The system of claim 1, wherein the linker region of the first and third compounds comprises a contiguous stretch of 60 to 500 thymine nucleotides.

14. The system of claim 1, wherein the linker region of the first and third compounds comprises a contiguous stretch 60 to 100 thymine nucleotides.

15. The system of claim 1, wherein the linker region of the first and third compounds comprises a contiguous stretch of 60 to 80 thymine nucleotides.

16. The system of claim 1, wherein the membrane anchoring region of the first and second compounds comprises a substituted aliphatic chain.

17. The system of claim 1, wherein there are no nucleotides separating the linker region from the membrane proximal end of the polynucleotide of the first compound and the second compound.

18. The system of claim 1, further comprising a fluorophore conjugated to the membrane distal end of the polynucleotide of the first compound.

19. The system of claim 1, further comprising a pharmaceutical composition.

20. The system of claim 1, wherein the membrane anchoring region of the first compound comprises dialkylphosphoglyceride comprising alkyl chains of 12-22 carbon atoms or a monoalkyl amide comprising a monoalkyl chain of 16 to 18 carbon atoms.

21. The system of claim 1, wherein the membrane anchoring region of the second compound comprises dialkylphosphoglyceride comprising alkyl chains of 12-22 carbon atoms or a monoalkyl amide comprising a monoalkyl chain of 16 to 18 carbon atoms.

22. The system of claim 1, wherein the contiguous stretch of at least 10 nucleotides of the second compound is hybridized to the linker region of the first compound.

23. The system of claim 1, wherein the polynucleotide of the first compound comprises a membrane proximal adhesion region between the linker and the membrane distal adhesion region and wherein the contiguous stretch of at least 10 nucleotides of the second compound is hybridized to the membrane proximal adhesion region of the first compound.

* * * * *

UNITED STATES PATENT AND TRADEMARK OFFICE
CERTIFICATE OF CORRECTION

PATENT NO. : 11,072,629 B2
APPLICATION NO. : 15/482591
DATED : July 27, 2021
INVENTOR(S) : Zev Jordan Gartner et al.

It is certified that error appears in the above-identified patent and that said Letters Patent is hereby corrected as shown below:

In the Specification

In Column 1, Line 55, "he" should read --be--
In Column 2, Line 29, "he" should read --be--
In Column 7, Line 66, "rnicro-tissues" should read --microtissues--
In Column 8, Line 47, "H2R-GFP-" should read --H2B-GFP--
In Column 8, Line 60, "MC10ARas-" should read --MCF10Aras--
In Column 10, Line 18, "he" should read --be--
In Column 10, Line 37, "he" should read --be--
In Column 10, Line 49, "he" should read --be--
In Column 21, Line 4, "1.40" should read --140--
In Column 22, Line 52, "dialkyiphosphoglyceride." should read --dialkylphosphoglyceride--
In Column 24, Line 8, "he" should read --be--
In Column 26, Line 9, "2.0" should read --20--
In Column 28, Line 34, "antiparkinsonisrn" should read --antiparkinsonism--
In Column 29, Line 14, "palmitoyloleoylphosphandylserine" should read
--palmitoyloleoylphosphatidylserine--
In Column 29, Line 18, "paimitelaidoyloleoylphosphatidylserine," should read
--palmitelaidoyloleoylphosphatidylserine,--
In Column 29, Line 20, "pahnitelaidoyloleoylphosphatidylglycerol" should read
--palmitelaidoyloleoylphosphatidylglycerol--
In Column 29, Line 36, "(lysophosphatidyiglycerol)" should read --(lysophosphatidylglycerol)--
In Column 33, Line 25, "H$_2$O/acetortitrile" should read --H2O/acetonitrile--
In Column 35, Line 45, "(100nM)" should read --(100 mM)--
In Column 36, Line 66, "(1 g/ml, Operon)" should read --(1ug/ml, Operon)--
In Column 38, Line 13, "Plutonic" should read --Pluronic--
In Column 39, Line 2, "ionornycin" should read --ionomycin--
In Column 39, Line 4, "latruneulin" should read --latrunculin--
In Column 40, Line 62, "Plutonic" should read --Pluronic--
In Column 42, Line 57, "RNase" should read --DNase--

Signed and Sealed this
Thirty-first Day of August, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 11,072,629 B2

In Column 43, Line 44, "51.0" should read --510--
In Column 43, Line 46, "CFP-labeled" should read --GFP-labeled--
In Column 46, Line 3, "he" should read --be--
In Column 46, Line 21, "phospho-Alt" should read --phospho-Akt--
In Column 46, Line 39, insert --with-- after "consistent"
In Column 47, Line 63, "MCP10ARas" should read --MCF10Aras--
In Column 48, Line 46, "he" should read --be--

```
                           SEQUENCE LISTING

<160> NUMBER OF SEQ ID NOS: 51

<210> SEQ ID NO 1
<211> LENGTH: 20
<212> TYPE: DNA
<213> ORGANISM: Artificial sequence
<220> FEATURE:
<223> OTHER INFORMATION: synthetic nucleic acid

<400> SEQUENCE: 1
gtaacgatcc agctgtcact                                               20

<210> SEQ ID NO 2
<211> LENGTH: 15
<212> TYPE: DNA
<213> ORGANISM: Artificial sequence
<220> FEATURE:
<223> OTHER INFORMATION: synthetic nucleic acid

<400> SEQUENCE: 2
gatccagctg tcact                                                    15

<210> SEQ ID NO 3
<211> LENGTH: 10
<212> TYPE: DNA
<213> ORGANISM: Artificial sequence
<220> FEATURE:
<223> OTHER INFORMATION: synthetic nucleic acid

<400> SEQUENCE: 3
agctgtcact                                                          10

<210> SEQ ID NO 4
<211> LENGTH: 20
<212> TYPE: DNA
<213> ORGANISM: Artificial sequence
<220> FEATURE:
<223> OTHER INFORMATION: synthetic nucleic acid

<400> SEQUENCE: 4
agtgacagct ggatcgttac                                               20

<210> SEQ ID NO 5
<211> LENGTH: 15
<212> TYPE: DNA
<213> ORGANISM: Artificial sequence
<220> FEATURE:
<223> OTHER INFORMATION: synthetic nucleic acid

<400> SEQUENCE: 5
agtgacagct ggatc                                                    15

<210> SEQ ID NO 6
<211> LENGTH: 10
<212> TYPE: DNA
<213> ORGANISM: Artificial sequence
<220> FEATURE:
<223> OTHER INFORMATION: synthetic nucleic acid

<400> SEQUENCE: 6
agtgacagct                                                          10
```

<210> SEQ ID NO 7
<211> LENGTH: 140
<212> TYPE: DNA
<213> ORGANISM: Artificial sequence
<220> FEATURE:
<223> OTHER INFORMATION: synthetic nucleic acid
<220> FEATURE:
<221> NAME/KEY: misc_feature
<222> LOCATION: (21)..(120)
<223> OTHER INFORMATION: "t" at any of these locations can be present or absent. Therefore, the feature of this location (nucleotide positions 21-120) can include a total of anywhere from 0-100 "t" bases.

<400> SEQUENCE: 7

```
gtaacgatcc agctgtcact tttttttttt tttttttttt tttttttttt tttttttttt      60
tttttttttt tttttttttt tttttttttt tttttttttt tttttttttt tttttttttt     120
cagtcagtca gtcagtcagt                                                 140
```

<210> SEQ ID NO 8
<211> LENGTH: 135
<212> TYPE: DNA
<213> ORGANISM: Artificial sequence
<220> FEATURE:
<223> OTHER INFORMATION: synthetic nucleic acid
<220> FEATURE:
<221> NAME/KEY: misc_feature
<222> LOCATION: (16)..(115)
<223> OTHER INFORMATION: "t" at any of these locations can be present or absent. Therefore, the feature of this location (nucleotide positions 16-115) can include a total of anywhere from 0-100 "t" bases.

<400> SEQUENCE: 8

```
gatccagctg tcactttttt tttttttttt tttttttttt tttttttttt tttttttttt      60
tttttttttt tttttttttt tttttttttt tttttttttt tttttttttt tttttcagtc     120
agtcagtcag tcagt                                                      135
```

<210> SEQ ID NO 9
<211> LENGTH: 130
<212> TYPE: DNA
<213> ORGANISM: Artificial sequence
<220> FEATURE:
<223> OTHER INFORMATION: synthetic nucleic acid
<220> FEATURE:
<221> NAME/KEY: misc_feature
<222> LOCATION: (11)..(110)
<223> OTHER INFORMATION: "t" at any of these locations can be present or absent. Therefore, the feature of this location (nucleotide positions 11-110) can include a total of anywhere from 0-100 "t" bases.

<400> SEQUENCE: 9

```
agctgtcact tttttttttt tttttttttt tttttttttt tttttttttt tttttttttt      60
tttttttttt tttttttttt tttttttttt tttttttttt tttttttttt cagtcagtca     120
gtcagtcagt                                                            130
```

<210> SEQ ID NO 10
<211> LENGTH: 80
<212> TYPE: DNA
<213> ORGANISM: Artificial sequence
<220> FEATURE:
<223> OTHER INFORMATION: synthetic nucleic acid

<400> SEQUENCE: 10
tttttttttt tttttttttt tttttttttt tttttttttt tttttttttt tttttttttt        60
actgactgac tgactgactg        80

<210> SEQ ID NO 11
<211> LENGTH: 20
<212> TYPE: DNA
<213> ORGANISM: Artificial sequence
<220> FEATURE:
<223> OTHER INFORMATION: synthetic nucleic acid

<400> SEQUENCE: 11
agtgacagct ggatcgttac        20

<210> SEQ ID NO 12
<211> LENGTH: 15
<212> TYPE: DNA
<213> ORGANISM: Artificial sequence
<220> FEATURE:
<223> OTHER INFORMATION: synthetic nucleic acid

<400> SEQUENCE: 12
agtgacagct ggatc        15

<210> SEQ ID NO 13
<211> LENGTH: 10
<212> TYPE: DNA
<213> ORGANISM: Artificial sequence
<220> FEATURE:
<223> OTHER INFORMATION: synthetic nucleic acid

<400> SEQUENCE: 13
agtgacagct        10

<210> SEQ ID NO 14
<211> LENGTH: 120
<212> TYPE: DNA
<213> ORGANISM: Artificial sequence
<220> FEATURE:
<223> OTHER INFORMATION: synthetic nucleic acid
<220> FEATURE:
<221> NAME/KEY: misc_feature
<222> LOCATION: (1)..(100)
<223> OTHER INFORMATION: "t" at any of these locations can be present or
      absent. Therefore, the feature of this location (nucleotide
      positions 1-100) can include a total of anywhere from 0-100 "t"
      bases.

<400> SEQUENCE: 14
tttttttttt tttttttttt tttttttttt tttttttttt tttttttttt tttttttttt        60
tttttttttt tttttttttt tttttttttt tttttttttt cagtcagtca gtcagtcagt       120

<210> SEQ ID NO 15
<211> LENGTH: 120
<212> TYPE: DNA
<213> ORGANISM: Artificial sequence
<220> FEATURE:
<223> OTHER INFORMATION: synthetic nucleic acid
<220> FEATURE:
<221> NAME/KEY: misc_feature
<222> LOCATION: (1)..(100)
<223> OTHER INFORMATION: "t" at any of these locations can be present or
      absent. Therefore, the feature of this location (nucleotide
      positions 1-100) can include a total of anywhere from 0-100 "t"
      bases.

<400> SEQUENCE: 15
tttttttttt tttttttttt tttttttttt tttttttttt tttttttttt tttttttttt        60
tttttttttt tttttttttt tttttttttt tttttttttt actgactgac tgactgactg    120

<210> SEQ ID NO 16
<211> LENGTH: 20
<212> TYPE: DNA
<213> ORGANISM: Artificial sequence
<220> FEATURE:
<223> OTHER INFORMATION: synthetic nucleic acid

<400> SEQUENCE: 16
cagtcagtca gtcagtcagt                                                 20

<210> SEQ ID NO 17
<211> LENGTH: 100
<212> TYPE: DNA
<213> ORGANISM: Artificial sequence
<220> FEATURE:
<223> OTHER INFORMATION: synthetic nucleic acid
<220> FEATURE:
<221> NAME/KEY: misc_feature
<222> LOCATION: (1)..(80)
<223> OTHER INFORMATION: "t" can be present or absent at these locations
      such that the feature of this location (nucleotide positions 1-80)
      can include a total of 0, 20, 40, 60, or 80 "t" bases.
<220> FEATURE:
<221> NAME/KEY: misc_feature
<222> LOCATION: (1)..(1)
<223> OTHER INFORMATION: The first nucleotide is conjugated to a C16
      dialkylphosphoglyceride

<400> SEQUENCE: 17
tttttttttt tttttttttt tttttttttt tttttttttt tttttttttt tttttttttt    60
tttttttttt tttttttttt cagtcagtca gtcagtcagt                          100

<210> SEQ ID NO 18
<211> LENGTH: 100
<212> TYPE: DNA
<213> ORGANISM: Artificial sequence
<220> FEATURE:
<223> OTHER INFORMATION: synthetic nucleic acid
<220> FEATURE:
<221> NAME/KEY: misc_feature
<222> LOCATION: (1)..(80)
<223> OTHER INFORMATION: "t" can be present or absent at these locations
      such that the feature of this location (nucleotide positions 1-80)
      can include a total of 0, 20, 40, 60, or 80 "t" bases.
<220> FEATURE:
<221> NAME/KEY: misc_feature
<222> LOCATION: (1)..(1)
<223> OTHER INFORMATION: The first nucleotide is conjugated to a C16
      dialkylphosphoglyceride

<400> SEQUENCE: 18
tttttttttt tttttttttt tttttttttt tttttttttt tttttttttt tttttttttt    60
tttttttttt tttttttttt actgactgac tgactgactg                          100

<210> SEQ ID NO 19
<211> LENGTH: 20
<212> TYPE: DNA
<213> ORGANISM: Artificial sequence
<220> FEATURE:
<223> OTHER INFORMATION: synthetic nucleic acid
<220> FEATURE:
<221> NAME/KEY: misc_feature
<222> LOCATION: (1)..(1)
<223> OTHER INFORMATION: The first nucleotide is conjugated to
      Difluorocyclooctyne (DIFO), N-hydroxysuccinimide (NHS), a C18
      dialkylphosphoglyceride, or a C16/18 monoalkylamide

<400> SEQUENCE: 19
cagtcagtca gtcagtcagt          20

<210> SEQ ID NO 20
<211> LENGTH: 20
<212> TYPE: DNA
<213> ORGANISM: Artificial sequence
<220> FEATURE:
<223> OTHER INFORMATION: synthetic nucleic acid
<220> FEATURE:
<221> NAME/KEY: misc_feature
<222> LOCATION: (1)..(1)
<223> OTHER INFORMATION: The first nucleotide is conjugated to
      Difluorocyclooctyne (DIFO), N-hydroxysuccinimide (NHS), a C18
      dialkylphosphoglyceride, or a C16/18 monoalkylamide

<400> SEQUENCE: 20
actgactgac tgactgactg          20

<210> SEQ ID NO 21
<211> LENGTH: 20
<212> TYPE: DNA
<213> ORGANISM: Artificial sequence
<220> FEATURE:
<223> OTHER INFORMATION: synthetic nucleic acid
<220> FEATURE:
<221> NAME/KEY: misc_feature
<222> LOCATION: (1)..(1)
<223> OTHER INFORMATION: The first nucleotide is conjugated to FAM

<400> SEQUENCE: 21
cagtcagtca gtcagtcagt          20

<210> SEQ ID NO 22
<211> LENGTH: 20
<212> TYPE: DNA
<213> ORGANISM: Artificial sequence
<220> FEATURE:
<223> OTHER INFORMATION: synthetic nucleic acid
<220> FEATURE:
<221> NAME/KEY: misc_feature
<222> LOCATION: (1)..(1)
<223> OTHER INFORMATION: The first nucleotide is conjugated to FAM

<400> SEQUENCE: 22
actgactgac tgactgactg          20

<210> SEQ ID NO 23
<211> LENGTH: 100
<212> TYPE: DNA
<213> ORGANISM: Artificial sequence
<220> FEATURE:
<223> OTHER INFORMATION: synthetic nucleic acid
<220> FEATURE:
<221> NAME/KEY: misc_feature
<222> LOCATION: (1)..(1)
<223> OTHER INFORMATION: The first nucleotide is conjugated to a C16
      dialkylphosphoglyceride

<400> SEQUENCE: 23
tttttttttt tttttttttt tttttttttt tttttttttt tttttttttt tttttttttt          60
tttttttttt tttttttttt cagtcagtca gtcagtcagt          100

<210> SEQ ID NO 24
<211> LENGTH: 100
<212> TYPE: DNA
<213> ORGANISM: Artificial sequence
<220> FEATURE:

<223> OTHER INFORMATION: synthetic nucleic acid
<220> FEATURE:
<221> NAME/KEY: misc_feature
<222> LOCATION: (1)..(1)
<223> OTHER INFORMATION: The first nucleotide is conjugated to a C16
      dialkylphosphoglyceride

<400> SEQUENCE: 24
tttttttttt tttttttttt tttttttttt tttttttttt tttttttttt tttttttttt    60
tttttttttt tttttttttt actgactgac tgactgactg                          100

<210> SEQ ID NO 25
<211> LENGTH: 100
<212> TYPE: DNA
<213> ORGANISM: Artificial sequence
<220> FEATURE:
<223> OTHER INFORMATION: synthetic nucleic acid
<220> FEATURE:
<221> NAME/KEY: misc_feature
<222> LOCATION: (1)..(1)
<223> OTHER INFORMATION: The first nucleotide is conjugated to a C16
      dialkylphosphoglyceride

<400> SEQUENCE: 25
tttttttttt tttttttttt tttttttttt tttttttttt tttttttttt tttttttttt    60
tttttttttt tttttttttt gtaacgatcc agctgtcact                          100

<210> SEQ ID NO 26
<211> LENGTH: 100
<212> TYPE: DNA
<213> ORGANISM: Artificial sequence
<220> FEATURE:
<223> OTHER INFORMATION: synthetic nucleic acid
<220> FEATURE:
<221> NAME/KEY: misc_feature
<222> LOCATION: (1)..(1)
<223> OTHER INFORMATION: The first nucleotide is conjugated to a C16
      dialkylphosphoglyceride

<400> SEQUENCE: 26
tttttttttt tttttttttt tttttttttt tttttttttt tttttttttt tttttttttt    60
tttttttttt tttttttttt agtgacagct ggatcgttac                          100

<210> SEQ ID NO 27
<211> LENGTH: 100
<212> TYPE: DNA
<213> ORGANISM: Artificial sequence
<220> FEATURE:
<223> OTHER INFORMATION: synthetic nucleic acid
<220> FEATURE:
<221> NAME/KEY: misc_feature
<222> LOCATION: (1)..(1)
<223> OTHER INFORMATION: The first nucleotide is conjugated to a C16
      dialkylphosphoglyceride

<400> SEQUENCE: 27
tttttttttt tttttttttt tttttttttt tttttttttt tttttttttt tttttttttt    60
tttttttttt tttttttttt tcatacgact cactctaggg                          100

<210> SEQ ID NO 28
<211> LENGTH: 100
<212> TYPE: DNA
<213> ORGANISM: Artificial sequence
<220> FEATURE:
<223> OTHER INFORMATION: synthetic nucleic acid
<220> FEATURE:
<221> NAME/KEY: misc_feature
<222> LOCATION: (1)..(1)
<223> OTHER INFORMATION: The first nucleotide is conjugated to a C16
      dialkylphosphoglyceride

<400> SEQUENCE: 28
tttttttttt tttttttttt tttttttttt tttttttttt tttttttttt tttttttttt    60
tttttttttt tttttttttt ccctagagtg agtcgtatga                          100

<210> SEQ ID NO 29
<211> LENGTH: 100
<212> TYPE: DNA
<213> ORGANISM: Artificial sequence
<220> FEATURE:
<223> OTHER INFORMATION: synthetic nucleic acid
<220> FEATURE:
<221> NAME/KEY: misc_feature
<222> LOCATION: (1)..(1)
<223> OTHER INFORMATION: The first nucleotide is conjugated to a C16
      dialkylphosphoglyceride

<400> SEQUENCE: 29
tttttttttt tttttttttt tttttttttt tttttttttt tttttttttt tttttttttt    60
tttttttttt tttttttttt actgactgac tgactgactg                          100

<210> SEQ ID NO 30
<211> LENGTH: 100
<212> TYPE: DNA
<213> ORGANISM: Artificial sequence
<220> FEATURE:
<223> OTHER INFORMATION: synthetic nucleic acid
<220> FEATURE:
<221> NAME/KEY: misc_feature
<222> LOCATION: (1)..(1)
<223> OTHER INFORMATION: The first nucleotide is conjugated to a C16
      dialkylphosphoglyceride

<400> SEQUENCE: 30
tttttttttt tttttttttt tttttttttt tttttttttt tttttttttt tttttttttt    60
tttttttttt tttttttttt cagtcagtca gtcagtcagt                          100

<210> SEQ ID NO 31
<211> LENGTH: 100
<212> TYPE: DNA
<213> ORGANISM: Artificial sequence
<220> FEATURE:
<223> OTHER INFORMATION: synthetic nucleic acid
<220> FEATURE:
<221> NAME/KEY: misc_feature
<222> LOCATION: (1)..(1)
<223> OTHER INFORMATION: The first nucleotide is conjugated to a C16
      dialkylphosphoglyceride

<400> SEQUENCE: 31
tttttttttt tttttttttt tttttttttt tttttttttt tttttttttt tttttttttt    60
tttttttttt tttttttttt actgatggta atctgcacct                          100

<210> SEQ ID NO 32
<211> LENGTH: 100
<212> TYPE: DNA
<213> ORGANISM: Artificial sequence
<220> FEATURE:
<223> OTHER INFORMATION: synthetic nucleic acid
<220> FEATURE:
<221> NAME/KEY: misc_feature
<222> LOCATION: (1)..(1)
<223> OTHER INFORMATION: The first nucleotide is conjugated to a C16
      dialkylphosphoglyceride

<400> SEQUENCE: 32
tttttttttt tttttttttt tttttttttt tttttttttt tttttttttt tttttttttt        60
tttttttttt tttttttttt aggtgcagat taccatcagt                              100

<210> SEQ ID NO 33
<211> LENGTH: 100
<212> TYPE: DNA
<213> ORGANISM: Artificial sequence
<220> FEATURE:
<223> OTHER INFORMATION: synthetic nucleic acid
<220> FEATURE:
<221> NAME/KEY: misc_feature
<222> LOCATION: (1)..(1)
<223> OTHER INFORMATION: The first nucleotide is conjugated to a C16
      dialkylphosphoglyceride

<400> SEQUENCE: 33
tttttttttt tttttttttt tttttttttt ttttttttc cctcattcaa taccctatcg         60
tttttttttt tttttttttt cagtcagtca gtcagtcagt                              100

<210> SEQ ID NO 34
<211> LENGTH: 100
<212> TYPE: DNA
<213> ORGANISM: Artificial sequence
<220> FEATURE:
<223> OTHER INFORMATION: synthetic nucleic acid
<220> FEATURE:
<221> NAME/KEY: misc_feature
<222> LOCATION: (1)..(1)
<223> OTHER INFORMATION: The first nucleotide is conjugated to a C16
      dialkylphosphoglyceride

<400> SEQUENCE: 34
tttttttttt tttttttttt tttttttttt tttttttttt ccctagagtg agtcgtatga        60
tttttttttt tttttttttt cagtcagtca gtcagtcagt                              100

<210> SEQ ID NO 35
<211> LENGTH: 120
<212> TYPE: DNA
<213> ORGANISM: Artificial sequence
<220> FEATURE:
<223> OTHER INFORMATION: synthetic nucleic acid
<220> FEATURE:
<221> NAME/KEY: misc_feature
<222> LOCATION: (1)..(1)
<223> OTHER INFORMATION: The first nucleotide is conjugated to a C16/18
      monoalkylamide
<220> FEATURE:
<221> NAME/KEY: misc_feature
<222> LOCATION: (21)..(100)
<223> OTHER INFORMATION: "t" can be present or absent at these locations
      such that the feature of this location (nucleotide positions
      21-100) can include a total of 0, 40, 60, or 80 "t" bases.

<400> SEQUENCE: 35
gtaacgatcc agctgtcact tttttttttt tttttttttt tttttttttt tttttttttt        60
tttttttttt tttttttttt tttttttttt tttttttttt cagtcagtca gtcagtcagt       120

<210> SEQ ID NO 36
<211> LENGTH: 95
<212> TYPE: DNA
<213> ORGANISM: Artificial sequence
<220> FEATURE:
<223> OTHER INFORMATION: synthetic nucleic acid
<220> FEATURE:
<221> NAME/KEY: misc_feature

```
<222> LOCATION: (1)..(1)
<223> OTHER INFORMATION: The first nucleotide is conjugated to a C18
      monoalkylamide

<400> SEQUENCE: 36
gatccagctg tcacttttt tttttttttt tttttttttt tttttttttt            60
tttttttttt ttttcagtc agtcagtcag tcagt                            95

<210> SEQ ID NO 37
<211> LENGTH: 90
<212> TYPE: DNA
<213> ORGANISM: Artificial sequence
<220> FEATURE:
<223> OTHER INFORMATION: synthetic nucleic acid
<220> FEATURE:
<221> NAME/KEY: misc_feature
<222> LOCATION: (1)..(1)
<223> OTHER INFORMATION: The first nucleotide is conjugated to a C18
      monoalkylamide

<400> SEQUENCE: 37
agctgtcact tttttttttt tttttttttt tttttttttt tttttttttt           60
tttttttttt cagtcagtca gtcagtcagt                                 90

<210> SEQ ID NO 38
<211> LENGTH: 80
<212> TYPE: DNA
<213> ORGANISM: Artificial sequence
<220> FEATURE:
<223> OTHER INFORMATION: synthetic nucleic acid
<220> FEATURE:
<221> NAME/KEY: misc_feature
<222> LOCATION: (1)..(1)
<223> OTHER INFORMATION: The first nucleotide is conjugated to a C18
      monoalkylamide

<400> SEQUENCE: 38
tttttttttt tttttttttt tttttttttt tttttttttt tttttttttt           60
actgactgac tgactgactg                                            80

<210> SEQ ID NO 39
<211> LENGTH: 20
<212> TYPE: DNA
<213> ORGANISM: Artificial sequence
<220> FEATURE:
<223> OTHER INFORMATION: synthetic nucleic acid
<220> FEATURE:
<221> NAME/KEY: misc_feature
<222> LOCATION: (20)..(20)
<223> OTHER INFORMATION: The last nucleotide is conjugated to a C16
      monoalkylamide

<400> SEQUENCE: 39
agtgacagct ggatcgttac                                            20

<210> SEQ ID NO 40
<211> LENGTH: 15
<212> TYPE: DNA
<213> ORGANISM: Artificial sequence
<220> FEATURE:
<223> OTHER INFORMATION: synthetic nucleic acid
<220> FEATURE:
<221> NAME/KEY: misc_feature
<222> LOCATION: (15)..(15)
<223> OTHER INFORMATION: The last nucleotide is conjugated to a C16
      monoalkylamide

<400> SEQUENCE: 40
```
agtgacagct ggatc                                              15

<210> SEQ ID NO 41
<211> LENGTH: 10
<212> TYPE: DNA
<213> ORGANISM: Artificial sequence
<220> FEATURE:
<223> OTHER INFORMATION: synthetic nucleic acid
<220> FEATURE:
<221> NAME/KEY: misc_feature
<222> LOCATION: (10)..(10)
<223> OTHER INFORMATION: The last nucleotide is conjugated to a C16
      monoalkylamide

<400> SEQUENCE: 41
agtgacagct                                                    10

<210> SEQ ID NO 42
<211> LENGTH: 20
<212> TYPE: DNA
<213> ORGANISM: Artificial sequence
<220> FEATURE:
<223> OTHER INFORMATION: synthetic nucleic acid
<220> FEATURE:
<221> NAME/KEY: misc_feature
<222> LOCATION: (1)..(1)
<223> OTHER INFORMATION: The first nucleotide is conjugated to FAM

<400> SEQUENCE: 42
cagtcagtca gtcagtcagt                                         20

<210> SEQ ID NO 43
<211> LENGTH: 20
<212> TYPE: DNA
<213> ORGANISM: Artificial sequence
<220> FEATURE:
<223> OTHER INFORMATION: synthetic nucleic acid
<220> FEATURE:
<221> NAME/KEY: misc_feature
<222> LOCATION: (1)..(1)
<223> OTHER INFORMATION: The first nucleotide is conjugated to FAM

<400> SEQUENCE: 43
actgactgac tgactgactg                                         20

<210> SEQ ID NO 44
<211> LENGTH: 21
<212> TYPE: DNA
<213> ORGANISM: Artificial sequence
<220> FEATURE:
<223> OTHER INFORMATION: synthetic nucleic acid
<220> FEATURE:
<221> NAME/KEY: misc_feature
<222> LOCATION: (1)..(1)
<223> OTHER INFORMATION: The first nucleotide is conjugated to a lipid

<400> SEQUENCE: 44
atgggcactc ggtgcgcgct g                                       21

<210> SEQ ID NO 45
<211> LENGTH: 23
<212> TYPE: DNA
<213> ORGANISM: Artificial sequence
<220> FEATURE:
<223> OTHER INFORMATION: synthetic nucleic acid
<220> FEATURE:
<221> NAME/KEY: misc_feature
<222> LOCATION: (1)..(1)
<223> OTHER INFORMATION: The first nucleotide is conjugated to biotin -continued

<400> SEQUENCE: 45
gacgcactca tccttctcct cgg                                          23

<210> SEQ ID NO 46
<211> LENGTH: 20
<212> TYPE: DNA
<213> ORGANISM: Artificial sequence
<220> FEATURE:
<223> OTHER INFORMATION: synthetic nucleic acid
<220> FEATURE:
<221> NAME/KEY: misc_feature
<222> LOCATION: (1)..(1)
<223> OTHER INFORMATION: The first nucleotide is conjugated to a linker
      via an SH group

<400> SEQUENCE: 46
actgactgac tgactgactg                                              20

<210> SEQ ID NO 47
<211> LENGTH: 20
<212> TYPE: DNA
<213> ORGANISM: Artificial sequence
<220> FEATURE:
<223> OTHER INFORMATION: synthetic nucleic acid
<220> FEATURE:
<221> NAME/KEY: misc_feature
<222> LOCATION: (1)..(1)
<223> OTHER INFORMATION: The first nucleotide is conjugated to a linker
      via an SH group

<400> SEQUENCE: 47
cagtcagtca gtcagtcagt                                              20

<210> SEQ ID NO 48
<211> LENGTH: 100
<212> TYPE: DNA
<213> ORGANISM: Artificial sequence
<220> FEATURE:
<223> OTHER INFORMATION: synthetic nucleic acid
<220> FEATURE:
<221> NAME/KEY: misc_feature
<222> LOCATION: (1)..(1)
<223> OTHER INFORMATION: The first nucleotide is conjugated to dialkyl

<400> SEQUENCE: 48
tttttttttt tttttttttt tttttttttt tttttttttt tttttttttt tttttttttt    60
tttttttttt tttttttttt actgactgac tgactgactg                         100

<210> SEQ ID NO 49
<211> LENGTH: 100
<212> TYPE: DNA
<213> ORGANISM: Artificial sequence
<220> FEATURE:
<223> OTHER INFORMATION: synthetic nucleic acid
<220> FEATURE:
<221> NAME/KEY: misc_feature
<222> LOCATION: (1)..(1)
<223> OTHER INFORMATION: The first nucleotide is conjugated to dialkyl

<400> SEQUENCE: 49
tttttttttt tttttttttt tttttttttt tttttttttt tttttttttt tttttttttt    60
tttttttttt tttttttttt cagtcagtca gtcagtcagt                         100

<210> SEQ ID NO 50
<211> LENGTH: 16
<212> TYPE: DNA

```
<213> ORGANISM: Artificial Sequence
<220> FEATURE:
<223> OTHER INFORMATION: Synthetic nucleic acid

<400> SEQUENCE: 50
cagtcagtca gtcagt                                              16

<210> SEQ ID NO 51
<211> LENGTH: 16
<212> TYPE: DNA
<213> ORGANISM: Artificial Sequence
<220> FEATURE:
<223> OTHER INFORMATION: Synthetic nucleic acid

<400> SEQUENCE: 51
actgactgac tgactg                                              16
```